(12) United States Patent
Pettersson et al.

(10) Patent No.: US 9,751,877 B2
(45) Date of Patent: *Sep. 5, 2017

(54) SUBSTITUTED PYRIDO[1,2-A]PYRAZINES FOR THE TREATMENT OF NEURODEGENERATIVE AND NEUROLOGICAL DISORDERS

(71) Applicant: Pfizer Inc., New York, NY (US)

(72) Inventors: Martin Youngjin Pettersson, Littleton, MA (US); Douglas Scott Johnson, Concord, MA (US); Chakrapani Subramanyam, South Glastonbury, CT (US); Christopher John O'Donnell, Mystic, CT (US); Christopher William am Ende, Mystic, CT (US); Michael Eric Green, Boston, MA (US); Nandini Chaturbhai Patel, Waban, MA (US); Cory Michael Stiff, Salem, CT (US); Tuan Phong Tran, Ledyard, CT (US); Gregory Wayne Kauffman, East Greenwich, RI (US); Antonia Friederike Stepan, Brookline, MA (US); Patrick Robert Verhoest, Newton, MA (US)

(73) Assignee: PFIZER INC., New York, NY (US)

(*) Notice: Subject to any disclaimer, the term of this patent is extended or adjusted under 35 U.S.C. 154(b) by 64 days.

This patent is subject to a terminal disclaimer.

(21) Appl. No.: 14/877,118

(22) Filed: Oct. 7, 2015

(65) Prior Publication Data

US 2016/0024088 A1  Jan. 28, 2016

Related U.S. Application Data

(60) Continuation of application No. 14/543,020, filed on Nov. 17, 2014, now Pat. No. 9,193,726, which is a division of application No. 14/031,163, filed on Sep. 19, 2013, now Pat. No. 8,916,564.

(60) Provisional application No. 61/703,969, filed on Sep. 21, 2012.

(51) Int. Cl.
*A61K 31/4985* (2006.01)
*C07D 471/04* (2006.01)

(52) U.S. Cl.
CPC .................. *C07D 471/04* (2013.01)

(58) Field of Classification Search
CPC .......... A61K 31/4985; C07D 471/04
USPC ........ 514/249; 544/349; 548/335.1; 549/429
See application file for complete search history.

(56) References Cited

U.S. PATENT DOCUMENTS 5,616,585 A   4/1997   Bright
5,700,810 A   12/1997  Natsugari et al.
6,489,315 B1  12/2002  Natsugari et al.
7,238,721 B2  7/2007   Chen et al.
7,253,180 B2  8/2007   Chen et al.
7,253,195 B2  8/2007   Chen et al.
7,342,118 B2  3/2008   Brodney et al.
7,517,532 B2  4/2009   Wai et al.
7,638,629 B2  12/2009  Hannam et al.
7,741,315 B2  6/2010   Vacca et al.
7,812,040 B2  10/2010  Wager
7,897,632 B2  3/2011   Kimura et al.
7,902,195 B2  3/2011   Hughes et al.
7,923,450 B2  4/2011   Baumann et al.
8,097,621 B2  1/2012   Bell et al.
8,697,673 B2  4/2014   Pettersson et al.
8,916,564 B2  12/2014  Pettersson et al.
2002/0132817 A1  9/2002   Natsugari et al.
2003/0195205 A1  10/2003  DeNinno et al.
2004/0220186 A1  11/2004  Bell et al.
2006/0106035 A1  5/2006   Hendrix et al.
2006/0111372 A1  5/2006   Hendrix et al.
2007/0031416 A1  2/2007   Shoji et al.
2007/0117798 A1  5/2007   Kimura et al.
2007/0117839 A1  5/2007   Kimura et al.
2007/0155731 A1  7/2007   Butora et al.

(Continued)

FOREIGN PATENT DOCUMENTS

EP  1145714   10/2001
GB  1419789   12/1975

(Continued)

OTHER PUBLICATIONS

Caldwell, J.P., et al., "Iminoheterocycles as •-secretasemodulators", Bioorganic & Medicinal Chemistry Letters, Sep. 15, 2010, pp. 5380-5384; 20(18).

(Continued)

*Primary Examiner* — Douglas M Willis
(74) *Attorney, Agent, or Firm* — J. Michael Dixon

(57) ABSTRACT

Compounds and pharmaceutically acceptable salts of the compounds are disclosed, wherein the compounds have the structure of Formula I

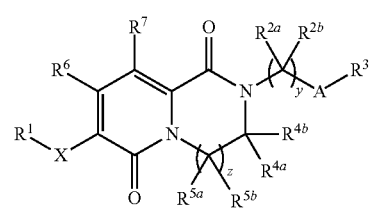

as defined in the specification. Corresponding pharmaceutical compositions, methods of treatment, methods of synthesis, and intermediates are also disclosed.

8 Claims, No Drawings

(56) References Cited

U.S. PATENT DOCUMENTS

| | | |
|---|---|---|
| 2007/0197581 A1 | 8/2007 | Asberom et al. |
| 2008/0009490 A1 | 1/2008 | Williams et al. |
| 2008/0076738 A1 | 3/2008 | Cai et al. |
| 2008/0194591 A1 | 8/2008 | Entwistle et al. |
| 2008/0207900 A1 | 8/2008 | Kimura et al. |
| 2008/0280948 A1 | 11/2008 | Baumann et al. |
| 2009/0062529 A1 | 3/2009 | Kimura et al. |
| 2009/0163482 A1 | 6/2009 | McHardy et al. |
| 2009/0215759 A1 | 8/2009 | Baumann et al. |
| 2009/0306054 A1 | 12/2009 | Cai et al. |
| 2010/0016373 A1 | 1/2010 | Khilevich et al. |
| 2010/0041680 A1 | 2/2010 | Rivkin |
| 2010/0093731 A1 | 4/2010 | Goetschi et al. |
| 2010/0105904 A1 | 4/2010 | Kimura et al. |
| 2010/0120874 A1 | 5/2010 | Baumann et al. |
| 2010/0130495 A1 | 5/2010 | Forsblom et al. |
| 2010/0137320 A1 | 6/2010 | Huang et al. |
| 2010/0204230 A1 | 8/2010 | Blurton et al. |
| 2010/0222320 A1 | 9/2010 | Fischer et al. |
| 2010/0247514 A1 | 9/2010 | Zhu et al. |
| 2010/0255005 A1 | 10/2010 | Zhu et al. |
| 2010/0256128 A1 | 10/2010 | Zhu et al. |
| 2010/0297128 A1 | 11/2010 | Huang et al. |
| 2010/0298359 A1 | 11/2010 | Huang et al. |
| 2010/0298372 A1 | 11/2010 | Huang et al. |
| 2010/0298381 A1 | 11/2010 | Zhu et al. |
| 2011/0009392 A1 | 1/2011 | Zhu et al. |
| 2011/0009619 A1 | 1/2011 | Kimura et al. |
| 2011/0015175 A1 | 1/2011 | Marcin et al. |
| 2011/0027264 A1 | 2/2011 | Huang et al. |
| 2011/0053918 A1 | 3/2011 | Zhu et al. |
| 2011/0070297 A1 | 3/2011 | Cao et al. |
| 2011/0082153 A1 | 4/2011 | Aslanian et al. |
| 2011/0118234 A1 | 5/2011 | Biswas et al. |
| 2011/0166132 A1 | 7/2011 | Hitchcock et al. |
| 2011/0172427 A1 | 7/2011 | Nakamura et al. |
| 2011/0207733 A1 | 8/2011 | Rivkin et al. |
| 2011/0237580 A1 | 9/2011 | Gijsen et al. |
| 2011/0251172 A1 | 10/2011 | Rivkin et al. |
| 2011/0257156 A1 | 10/2011 | Zhu et al. |
| 2011/0263529 A1 | 10/2011 | Xu et al. |
| 2011/0275822 A1 | 11/2011 | Minamisono et al. |
| 2011/0281881 A1 | 11/2011 | Gijsen et al. |
| 2011/0294784 A1 | 12/2011 | Asberom et al. |
| 2011/0313001 A1 | 12/2011 | Fischer et al. |
| 2012/0022044 A1 | 1/2012 | Fischer et al. |
| 2012/0022090 A1 | 1/2012 | Gijsen et al. |
| 2012/0053165 A1 | 3/2012 | Allen et al. |
| 2012/0252758 A1 | 10/2012 | Pettersson et al. |
| 2014/0045790 A1 | 2/2014 | Pettersson et al. |
| 2014/0088111 A1 | 3/2014 | Pettersson et al. |
| 2015/0274721 A1 | 10/2015 | Pettersson et al. |

FOREIGN PATENT DOCUMENTS

| | | |
|---|---|---|
| WO | 9944955 | 10/1999 |
| WO | 2004024078 | 3/2004 |
| WO | 2006126081 | 11/2006 |
| WO | 2006126082 | 11/2006 |
| WO | 2006126083 | 11/2006 |
| WO | 2007063385 | 6/2007 |
| WO | 2007088450 | 8/2007 |
| WO | 2007088462 | 8/2007 |
| WO | 2007099423 | 9/2007 |
| WO | 2007138431 | 12/2007 |
| WO | 2008137102 | 11/2008 |
| WO | 2009050227 | 4/2009 |
| WO | 2009061699 | 5/2009 |
| WO | 2010075204 | 7/2010 |
| WO | 2010098332 | 9/2010 |
| WO | 2010098488 | 9/2010 |
| WO | 2010098495 | 9/2010 |
| WO | 2010098496 | 9/2010 |
| WO | 2011048525 | 4/2011 |
| WO | 2012131539 | 10/2012 |
| WO | 2013171712 A1 | 11/2013 |
| WO | 2014047372 A1 | 3/2014 |
| WO | 2014096212 | 6/2014 |
| WO | WO 2014111457 | 7/2014 |
| WO | 2015049616 | 4/2015 |

OTHER PUBLICATIONS

Eiden, F., et al., "1-Pyrono-und 1-Pyridono-[3,4-b]chinoxaline. 33. Mitt. über Untersuchungen an 4-Pyronen", Archiv der Pharmazie, 1972, pp. 2-9; 305(1).

Eiden, F., et al., Pyrono-Chinoxaline AUS 3-Hydroxy-4-Pyronen1), Tetrahedron Letters, 1968, pp. 2903-2904, 9(24).

Garbaccio, R.M., et al., "Discovery of Oxazolobenzimidazoles as Positive Allosteric Modulators for the mGluR2 Receptors", ACS Medicinal Chemistry Letters, 2010, pp. 406-410; 1(8).

Gillman, K., et al., "Discovery and Evaluation of BMS-708163, a Potent Selective and Orally Bioavailable γ-Secretase Inhibitor", ACS Medicinal Chemistry Letters, Mar. 22, 2010, pp. 120-124; 1(3).

Goel, A., et al., "Amberlyst 15-Catalyzed Efficient synthesis of 5-Acetyl-4-hydroxy-coumarone and 5-Acetyl-6-hydroxy-coumarone: Crucial Precursors for Several Naturally Occurring Furanoflavones1", Synlett, 2004, pp. 1990-1994; vol. 11.

Grunewald, G.L., et al., "Binding Requirements of Phenolic Phenylethylamines in the Benzonorbornene skeleton at the Active site of Phenylethanolamine N-Methyltransferase1a,b", Journal Medical Chemistry, Sep. 1986, pp. 1972-1982; 29(10).

Haleblian, et al., "Characterization of Habits and Crystalline Modification of Solids and Their Pharmaceutical Applications", Journal of Pharmaceutical Science, Aug. 1975, pp. 1269-1288; 64(8).

Hashimoto, T., et al., "A Novel Gamma-secretase Modulator-Pharmacology Part", Journal of Alzheimer's & Dementia, Jul. 2010, Supplemental, pp. S242 (PI-236); 6(4).

Huang, X, et al., "The Discovery of Pyridone and Pyridazone Heterocycles as •-SecretaseModulators", ACS Medicinal Chemistry Letters, 2010, pp. 184-187; 1(4).

Hughes, J.D., et al., "Physiochemical drug properties associated with in vivo toxicological outcomes", Bioorganic & Medicinal Chemistry Letters, Sep. 1, 2008, pp. 4872-4875; 18(17).

Inamoto, K., et al., "Palladium-Catalyzed Synthesis of 2-Substituted Benzothiazoles via a C—H Functionalization/Intramolecular C—S Bond Formation Process", Organic Letters, 2008, pp. 5147-5150; 10(22).

Kato, D., et al.,"Microbial Deracemization of α-Substituted Carboxylic Acids: Substrate Specificity and Mechanistic Investigation", Journal Organic Chemistry, Sep. 19, 2003, pp. 7234-7242; 68(19).

Kawahara, N., et al., "A simple synthesis of dimethyl 2-pyridone-4, 5-dicarboxylate derivatives", Journal of Heterocyclic Chemistry, 1989, pp. 847-852; 26(3).

Kawahara, N., et al., "Synthesis and Thermal Cyclization Reactions of Methyl Isocrotonate Derivatives", Chemical & Pharmaceutical Bulletin, Feb. 1987, pp. 457-467; 35(2).

Kounnas, Maria Z., et al., "Modulation of •-Secretase Reduces β-Amyloid Deposition in a Transgenic Mouse Model of Alzheimer's Disease", Neuron, Sep. 9, 2010, pp. 769-780; 67(5).

Lee, J.C., et al., "Facile Synthesis of Oxazoles Starting from Ketones", Synthetic Communications 2003, pp. 1611-1614; 33(9).

Lin, Y., et al., "New Synthesis of Isoxazoles and Isothiazoles. A Convenient Synthesis of Thioenaminones from Enaminones", Journal of Organic Chemistry, Nov. 1980, pp. 4857-4860; 45(24).

Liu, J., et al., "Synthesis and Photophysical Properties of New Fluorinated Benzo[c]xanthene Dyes as Intracellular pH Indicators", Bioorganic & Medicinal Chemistry Letters, 2001, pp. 2903-2905; 11(22).

Liu, W., et al., "Total synthesis of Isoprekinamycin: Structural Evidence for Enhanced Diazonium Ion Character and Growth Inhibitory Activity toward Cancer Cells", Organic Letters, 2007, pp. 2915-2918; 9(15).

Morphy, Richard, "The Influence of Target Family and Functional Activity on the Physicochemical Properties of Pre-Clinical Compounds", Journal of Medicinal Chemistry, 2006, pp. 2969-2978; 49(10).

(56) References Cited

OTHER PUBLICATIONS

Narender, N., et al., "Highly Efficient, Para-selective Oxychlorination of Aromatic Compound Using Potassium Chloride and Oxone", Synthetic Communication 2002, pp. 279-286; 32(2).
Oliveira, M.M., et al., "Synthesis and photochromic behavior under flash photolysis and continuous irradiation of novel 2H-chromenes derived from hydroxydibenzothiophenes", Tetrahedron, Feb. 25, 2002, pp. 1709-1718; 58(9).
Olsen, R., et al., "Secretase Inhibitors and Modulators for the Treatment of Alzheimer's Disease", Annual Report in Medicinal Chemistry, 2007, pp. 27-47; vol. 42.
Platonov, D., et al., "Synthesis of substituted 2-alkyl-5-hydroxy-1-oxo-1,2-dihydroisoquinolines and their new condensed structures", Mendeleev Communications, 2010, pp. 83-85; vol. 20.
Rivkin, A. et al., "Piperazinyl Pyrimidine Derivatives as Potent •SecretaseModulators", Bioorganic & Medicinal Chemistry Letters, Feb. 1, 2010, pp. 1269-1271; 20(3).
Rivkin, X., et al., "Purine Derivatives as Potent •SecretaseModulators", Bioorganic & Medicinal Chemistry Letters, Apr. 1, 2010, pp. 2279-2282; 20(7).
Sanz, R., et al., "Regioselective Synthesis of 4- and 7-Alkoxyindoles from 2,3-Dihalophenols: Application to the Preparation of Indole Inhibitors of Phospholipase A2"Journal Organic Chemistry, Jun. 6, 2007, pp. 5113-5118; 72(14).
Shen, L., et al., "Synthesis and structure-activity relationships of thiadiazole-derivatives as potent and orally active peroxisome proliferator-activated receptors a/• dual agonists", Bioorganic Medicinal Chemistry, Mar. 15, 2008, pp. 3321-3341; 16(6).
Shtarev, A.B., et al., "Partially Bridge-Fluorinated Dimethyl Bicyclo[1.1.1.]pentane-1,3-dicarboxylates: Preparation and NMR Spectra", Journal American Chemical Society, 2001, pp. 3484-3492; 123(15).
Shultz, D.A., et al., "Design, Synthesis, and Properties of Conformationally Fixed Semiquinone Monoradical Species", Journal Organic Chemistry, Nov. 24, 2006, pp. 9104-9113; 71(24).
Tsunoda, T., et al., "1,1'-(Azodicarbonyl)dipiperidine-Tributylphosphines, A New Reagent System for Mitsunobu Reaction", Tetrahedron Letters, Mar. 5, 1993, pp. 1639-1642; 34(10).
Van Camp, J.A., et al., "Preparation of 4-aryl-2-trifluoromethylbenzonitrile derivatives as androgen receptor antagonists for topical suppression of sebum production", Bioorganic & Medicinal Chemistry Letters, 2007, pp. 5529-5532; 17(20).
Wager, T.T., et al., "Defining Desirable Central Nervous System Drug Space through the Alignment of Molecular Properties, in Vitro ADME, and Safety Attributes", ACS Chemical Neuroscience, 2010, pp. 420-434; 1(6).
Wai, J.S., et al., "Dihydroxypryridopyrazine-1,6-dione HIV-1 integrase inhibitors", Bioorganic & Medicinal Chemistry Letters, 2007, pp. 5595-5599; 17(20).
Zhang, J., et al., "TiCl4-Catalyzed Friedel-Crafts Reaction of Trifluoroacetaldehyde Ethyl Hemiacetal (TFAE)", Synthetic Communications, 2011, pp. 3045-3052; 41(20).
Zhu, Zhanoning, et al., "Discovery of Cyclic Acylguanidines as Highly Potent and Selective β-Site Amyloid Cleaving Enzyme (BACE) Inhibitors: Part 1—Inhibitor Design and Validation", Journal of Medicinal Chemistry Letters, 2010, pp. 951-965; 53(3).
Zoellinger, M., et al., "Skeleton Diversity by Cyclopropanation of Tricyclic Acylenamines", Journal of Chemical Sciences, 2009, pp. 617-623; 64(b).
Kawahara, N., et al., "A Synthesis of Pyrido[1,2-a]Quinoxalines and Pryrido[1,2-a]-Pyrazines1)", Heterocycles, 1983, pp. 1721-1725; 20(9).
International application No. PCT/IB2012/051348, filed Mar. 21, 2012, Search Report mailed May 11, 2012, 4 pages.
International application No. PCT/IB2012/051348, filed Mar. 21, 2012, Written Opinion of International Searching Authority, mailed May 11, 2912, 7 pages.
International application No. PCT/IB2013/058347, filed Sep. 6, 2013, Search Report and Written Opinion, mailed Jan. 15, 2014, 10 pages.
Pettersson, M. et al., Design of Pyridopyrazine-1,6-dione γ-Secretase Modulators that Align Potency, MDR Efflux Ratio, and Metabolic Stability, ACS Medicinal Chemistry Letters, 2015, 6(5), pp. 596-601.
Pettersson, M. et al., Discovery of indole-derived pyridopyrazine-1,6-dione c-secretase modulators that target presenilin, Bioorganic & Medicinal Chemistry Letters, Feb. 15, 2015;25(4):908-13.
Tran, T. P. et al., Synthesis of Pyridopyrazine-1,6-diones from 6-Hydroxypicolinic Acids via a One-Pot Coupling/Cyclization Reaction, Organic Letters, 2013, vol. 15, No. 3, pp. 642-645.
International Search Report and the Written Opinion of the International Searching Authority, PCT/IB2015/051988, date May 12, 2015.
Pettersson, M. et al., Design, Synthesis, and Pharmacological Evaluation of a Novel Series of Pyridopyrazine-1-6-dione y-Secretase Modulators, Journal of Medicinal Chemistry, Feb. 13, 2014, pp. 1046-1062, vol. 57(3).
International Search Report and th Written Opinion of the International Searching Authority, PCT/IB2014/064738 dated Dec. 15, 2014.
International Search Report and th Written Opinion of the International Searching Authority, PCT/IB2016/050384 dated Jan. 26, 2016.
Database Caplus Chemical Abstracts Service, Columbus, Ohio, US; Database Accession No. 2015:1580140, Abstract of U.S. Publication No. 20150274721, Pettersson et al., Oct. 1, 2015.

SUBSTITUTED PYRIDO[1,2-A]PYRAZINES FOR THE TREATMENT OF NEURODEGENERATIVE AND NEUROLOGICAL DISORDERS

CROSS REFERENCE

This application is a continuation of U.S. patent application Ser. No. 14/543,020 filed Nov. 17, 2014, which is a divisional patent application of U.S. patent application Ser. No. 14/031,163, filed on Sep. 19, 2013, which claims benefit of U.S. provisional patent application No. 61/703,969, filed on Sep. 21, 2012, the disclosures of which are hereby incorporated by reference in their entirety.

FIELD OF THE INVENTION

The present invention relates to the treatment of Alzheimer's disease and other neurodegenerative and/or neurological disorders in mammals, including humans. This invention also relates to the modulation, in mammals, including humans, of the production of A-☐beta peptides that can contribute to the formation of neurological deposits of amyloid protein. More particularly, this invention relates to novel bicyclic pyridinone compounds useful for the treatment of neurodegenerative and/or neurological disorders, such as Alzheimer's disease and Down's Syndrome.

BACKGROUND OF THE INVENTION

Dementia results from a wide variety of distinctive pathological processes. The most common pathological processes causing dementia are Alzheimer's disease (AD), cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD affects nearly half of all people past the age of 85, the most rapidly growing portion of the United States population. As such, the number of AD patients in the United States is expected to increase from about 4 million to about 14 million by 2050.

The present invention relates to a group of γ-secretase modulators, useful for the treatment of neurodegenerative and/or neurological disorders such as Alzheimer's disease and Down's Syndrome. (see Ann. Rep. Med. Chem. 2007, Olsen et al., 42: 27-47).

SUMMARY OF THE INVENTION

The present invention is directed to γ-secretase modulators of Formula I or pharmaceutically acceptable salts thereof as represented below:

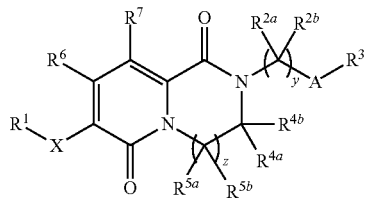

I wherein:
X is a 5- to 14-membered heteroaryl containing 1-3 heteroatoms;

$R^1$ is hydrogen, halogen, $C_1$-$C_6$alkyl, $C_3$-$C_6$cycloalkyl, or $C_2$-$C_6$alkenyl; wherein said alkyl, cycloalkyl or alkenyl is optionally substituted with one to three substituents each independently selected from the group consisting of fluoro, hydroxyl and $C_1$-$C_6$alkoxy;

A is a $C_3$-$C_6$cycloalkyl or a 4- to 10-membered heterocycloalkyl; wherein said cycloalkyl or heterocycloalkyl is optionally substituted with one to three substituents each independently selected from the group consisting of halogen and $C_1$-$C_6$alkyl;

$R^{2a}$ and $R^{2b}$ for each occurrence is independently hydrogen, fluoro, cyano, —$CF_3$, $C_1$-$C_6$alkyl, $C_2$-$C_6$alkenyl, $C_3$-$C_6$cycloalkyl, $C_4$-$C_8$bicycloalkyl, $C_2$-$C_6$alkynyl or phenyl; wherein said alkyl, alkenyl, cycloalkyl, bicycloalkyl, alkynyl or phenyl is optionally substituted with one to three substituents each independently selected from the group consisting of cyano, $C_1$-$C_3$alkyl and fluoro; or $R^{2a}$ and $R^{2b}$ together with the carbon to which they are bonded form a 3- to 5-membered cycloalkyl optionally substituted with one to three of $R^8$;

$R^3$ is hydrogen, halogen, $C_1$-$C_6$alkyl, $C_2$-$C_6$alkenyl, —$(C(R^{10})_2)_t$—$(C_3$-$C_6$cycloalkyl), —$(C(R^{10})_2)_t$-(4- to 10-membered heterocycloalkyl), —$(C(R^{10})_2)_t$—$(C_6$-$C_{10}$aryl), —$(C(R^{10})_2)_t$-(5- to 10-membered heteroaryl) or —$(C(R^{10})_2)_t$—$OR^{12}$; wherein said alkyl, alkenyl, cycloalkyl, heterocycloalkyl, aryl or heteroaryl is optionally substituted with one to five of $R^{11}$;

$R^{4a}$ and $R^{4b}$ are each independently hydrogen, —$CF_3$, or $C_1$-$C_6$alkyl, wherein said alkyl is optionally substituted with one to three substituents each independently selected from the group consisting of —$CF_3$, cyano and fluoro; or $R^{4a}$ and $R^{4b}$ together with the carbon to which they are bonded form a 3- to 5-membered cycloalkyl, wherein said cycloalkyl is optionally substituted with one to three substituents each independently selected from the group consisting of —$CF_3$, cyano, fluoro and $C_1$-$C_6$alkyl;

$R^{5a}$ and $R^{5b}$ for each occurrence are each independently hydrogen, —$CF_3$, or $C_1$-$C_6$alkyl, wherein said alkyl is optionally substituted with one to three substituents each independently selected from the group consisting of —$CF_3$, cyano and fluoro; or $R^{5a}$ and $R^{5b}$ together with the carbon to which they are bonded form a 3- to 5-membered cycloalkyl, wherein said cycloalkyl is optionally substituted with one to three substituents each independently selected from the group consisting of —$CF_3$, cyano, fluoro and $C_1$-$C_6$alkyl;

$R^6$, $R^7$ and $R^8$ are each independently hydrogen, —$CF_3$, cyano, halogen, $C_1$-$C_6$alkyl, or —$OR^9$; provided that $R^6$ and $R^7$ cannot both be —OH;

$R^9$ is hydrogen, $C_1$-$C_6$alkyl or —$CF_3$; wherein said alkyl is optionally substituted with one to three substituents each independently selected from the group consisting of cyano and fluoro;

each $R^{10}$ is independently hydrogen, halogen, cyano, —$CF_3$, $C_1$-$C_6$alkyl, or —$SF_5$; wherein said alkyl is optionally substituted with one to three fluoro;

each $R^{11}$ is independently hydrogen, halogen, —$CF_3$, —$SF_5$, —$Si(CH_3)_3$, —$OR^{12}$, $C_1$-$C_6$alkyl, $C_2$-$C_6$alkenyl, $C_2$-$C_6$alkynyl, —$(C(R^{10})_2)_t$—$(C_3$-$C_6$cycloalkyl), —$(C(R^{10})_2)_t$—$(C_6$-$C_{10}$aryl) or —$(C(R^{10})_2)_t$-(5- to 10-membered heteroaryl) wherein said —$Si(CH_3)_3$, alkyl, alkenyl, alkynyl, cycloalkyl, aryl or heteroaryl is optionally substituted with one to five substituents each independently selected from the group consisting of halogen and —$CF_3$;

each $R^{12}$ is hydrogen, $C_1$-$C_6$alkyl, —$(C(R^{13})_2)_n$—$(C_3$-$C_6$cycloalkyl), —$(C(R^{13})_2)_n$-(4- to 10-membered heterocycloalkyl), —$(C(R^{13})_2)_n$—$(C_6$-$C_{10}$aryl), or —$(C(R^{13})_2)_n$-(5- to 10-membered heteroaryl); wherein said alkyl, cycloalkyl, heterocycloalkyl, aryl or heteroaryl is optionally substituted with one to five of $R^{14}$;

each $R^{13}$ is independently hydrogen, $C_1$-$C_6$alkyl, $C_2$-$C_6$alkenyl, $C_2$-$C_6$alkynyl, halogen, cyano, —$CF_3$, or —$OCF_3$;

$R^{14}$ is independently hydrogen, —$CF_3$, cyano, halogen or $C_{1-6}$alkyl; wherein said alkyl is optionally substituted with one to three substituents each independently selected from the group consisting of hydroxyl, —$CF_3$, cyano and fluoro; and each t or n is an integer independently selected from 0, 1, 2 or 3;

each z is an integer independently selected from 1 or 2;

each y is an integer independently selected from 0, 1, 2, 3 or 4.

Compounds of the invention include Examples 1-73 or a pharmaceutically acceptable salt thereof as described herein.

Also provided herein are compositions comprising a pharmaceutically effective amount of one or more of the compounds described herein and a pharmaceutically acceptable vehicle, carrier or excipient.

The compounds of Formula I are γ-secretase modulators. γ-Secretase plays a role in the production of amyloid beta protein (Aβ) plaques associated with Alzheimer's Disease. Accordingly, the compounds of Formula I are useful in treating a variety of neurodegenerative and/or neurological disorders related to AR production.

Other features and advantages of this invention will be apparent from this specification and the appending claims which describe the invention.

DETAILED DESCRIPTION OF THE INVENTION

The headings within this document are only being utilized to expedite its review by the reader. They should not be construed as limiting the invention or claims in any manner.

Definitions and Exemplifications

As used throughout this application, including the claims, the following terms have the meanings defined below, unless specifically indicated otherwise. The plural and singular should be treated as interchangeable, other than the indication of number:

The term "$C_1$-$C_6$alkyl" refers to a linear or branched-chain saturated hydrocarbyl substituent (i.e., a substituent obtained from a hydrocarbon by removal of a hydrogen) containing from 1 to 6 carbon atoms. Examples of such substituents include methyl, ethyl, propyl (including n-propyl and isopropyl), butyl (including n-butyl, isobutyl, sec-butyl and tert-butyl), pentyl, and hexyl.

The term "$C_1$-$C_3$alkyl" refers to a linear or branched-chain saturated hydrocarbyl substituent (i.e., a substituent obtained from a hydrocarbon by removal of a hydrogen) containing from 1 to 3 carbon atoms. Examples of such substituents include methyl, ethyl, and propyl (including n-propyl and isopropyl).

The term "$C_2$-$C_6$alkenyl" refers to an aliphatic hydrocarbon containing from 1 to 6 carbon atoms and having at least one carbon-carbon double bond, including straight chain or branched chain groups having at least one carbon-carbon double bond. Representative examples include, but are not limited to, ethenyl, 1-propenyl, 2-propenyl (allyl), isopropenyl, 2-methyl-1-propenyl, 1-butenyl, and 2-butenyl. When the compounds of the invention contain a $C_2$-$C_6$alkenyl group, the compound may exist as the pure E (entgegen) form, the pure Z (zusammen) form, or any mixture thereof.

The term "$C_2$-$C_6$alkynyl" refers to an aliphatic hydrocarbon containing from 2 to 6 carbon atoms and having at least one carbon-carbon triple bond, including straight chain or branched chain groups having at least one carbon-carbon triple bond. Representative examples of an alkynyl include, but are not limited to, to acetylenyl, 1-propynyl, 2-propynyl, 3-butynyl, 2-pentynyl, and 1-butynyl.

The term "$C_3$-$C_6$cycloalkyl" refers to a carbocyclic substituent obtained by removing a hydrogen from a saturated carbocyclic molecule and having 3 to 6 carbon atoms. A cycloalkyl may be a single ring, which typically contains from 3 to 6 ring atoms. Examples include cyclopropyl, cyclobutyl, cyclopentyl, and cyclohexyl. A cycloalkyl may contain one or more double or triple bonds depending upon the number of carbon atoms contained in the ring (e.g., cyclohexene has one carbon to carbon double bond or cycloheyne has one carbon to carbon triple bond). Alternatively, a cycloalkyl may be a double ring such as a bicycloalkyl, e.g., $C_4$-$C_8$bicycloalkyl. The term "$C_4$-$C_8$bicycloalkyl" refers to a double ring containing 4 to 8 carbon atoms. The bicycloalkyl may be fused together, such as bicyclo[1.1.0]butane, bicyclo[2.1.0]pentane, bicyclo[2.2.0]hexane, bicyclo[3.1.0]hexane bicylco[3.2.0]heptanes and octohydropentalene. The term "bicycloalkyl" also includes bridged bicycloalkyl systems such as, but not limited to, bicyclo[2.2.1]heptane and bicyclo[1.1.1]pentane.

The term "$C_6$-$C_{10}$aryl" refers to an aromatic substituent containing from 6 to 10 carbon atoms, including one ring or two fused rings. Examples of such aryl substituents include, but not limited to, phenyl, naphthyl, and dihydroindenyl.

The term "hydrogen" refers to a hydrogen substituent, and may be depicted as —H.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents are attached include, for example, alcohols, enols and phenol.

The term "cyano" (also referred to as "nitrile") means —CN, which also may be depicted:

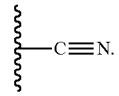

The term "halogen" refers to fluorine (which may be depicted as —F), chlorine (which may be depicted as —Cl), bromine (which may be depicted as —Br), or iodine (which may be depicted as —I). In one embodiment, the halogen is chlorine. In another embodiment, the halogen is fluorine. In another embodiment, the halogen is bromine.

The term "($C_1$-$C_6$)alkoxy" as used herein, means a ($C_1$-$C_6$)alkyl group, as defined herein, appended to the parent molecular moiety through an oxygen atom. Examples include, but are not limited to, methoxy, ethoxy, and n-propoxy.

The term "4- to 10-membered heterocycloalkyl" refers to a substituent obtained by removing a hydrogen from a saturated or partially saturated ring structure containing a total of 4 to 10 ring atoms, wherein at least one of the ring atoms is a heteroatom selected from oxygen, nitrogen, or sulfur. Examples of 4- to 10-membered heterocycloalkyls include, but are not limited to, dihydrofuranyl, tetrahydrofuranyl, tetrahydropyranyl, dihydrothiophenyl, and tetrahydrothiophenyl. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be the at least one heteroatom when the heteroatom is nitrogen, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom when the heteroatom is nitrogen, or it may be bound to a ring carbon atom, where the ring carbon atom may be in the same ring as the at least one heteroatom or where the ring carbon atom may be in a different ring from the at least one heteroatom.

The term "5- to 14-membered heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include but are not limited to: 6-membered ring substituents such as pyridyl, pyrazyl, pyrimidinyl, and pyridazinyl; 5-membered ring substituents such as triazolyl, imidazolyl, furanyl, thiophenyl (also known as "thiofuranyl"), pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused ring substituents such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom when the heteroatom is nitrogen, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom when the heteroatom is nitrogen, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

If a substituent is described as being "substituted," a non-hydrogen substituent is in the place of a hydrogen substituent on a carbon or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

This specification uses the terms "substituent," "radical," and "group" interchangeably.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

If substituents are described as being "independently selected" from a group, each substituent is selected independent of the other(s). Each substituent therefore may be identical to or different from the other substituent(s).

It is understood that descriptions of any one substituent, such as $R^1$, may be combined with descriptions of any other substituents, such as $R^2$, such that each and every combination of the first substituent and the second substituent is provided herein the same as if each combination were specifically and individually listed. For example, in one variation, $R^1$ is taken together with $R^2$ to provide an embodiment wherein $R^1$ is methyl and $R^2$ is halogen.

As used herein the terms "Formula I", "Formula Ia", "Formula Ib", and "Formula Ic" may be hereinafter referred to as "compound(s) of the invention." Such terms are also defined to include all forms of the compound of Formulas I, Ia, Ib, and Ic, including hydrates, solvates, isomers, crystalline and non-crystalline forms, isomorphs, polymorphs, and metabolites thereof. For example, the compounds of Formulas I, Ia, Ib and Ic or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein, in contrast to the aforementioned solvates, the drug and host are present in stoichiometric or non-stoichiometric amounts. Also included are complexes of Formulas I, Ia, Ib, and Ic containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention may have asymmetric carbon atoms. The carbon-carbon bonds of the compounds of the invention may be depicted herein using a solid line (—) a solid wedge (——) or a dotted wedge ( ........ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry are marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, and conformational isomers. The compounds of the invention may exhibit more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention also includes isotopically-labeled compounds, which are identical to those recited in Formulas I, Ia, Ib and Ic, but for the fact that one or more atoms are replaced by an atom having an atomic mass or mass number different from the atomic mass or mass number usually found in nature. Examples of isotopes that may be incorporated into compounds of the invention include isotopes of hydrogen, carbon, nitrogen, oxygen, phosphorus, fluorine and chlorine, such as, but not limited to, $^2H$, $^3H$, $^{13}C$, $^{14}C$, $^{15}N$, $^{18}O$, $^{17}O$, $^{32}P$, $^{35}S$, $^{18}F$, and $^{36}Cl$. Certain isotopically-labeled compounds of compounds of the invention for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalenesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts. The term "therapeutically effective amount" as used herein refers to that amount of the compound being administered which will relieve to some extent one or more of the symptoms of the disorder being treated.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

Compounds

To further elucidate the compounds of the present invention, the following subgenuses are described below.

Formula Ia depicted below is a subset of Formula I as depicted, wherein z is 1, and $R^{5a}$, $R^{5b}$, $R^6$ and $R^7$ are each hydrogen. In Formula Ia X is a 5-membered heteroaryl selected from imidazolyl, pyrazolyl, isothiazolyl, thiazolyl, isoxazolyl, oxazolyl or pyridyl; $R^1$ is selected from hydrogen, halogen, or $C_1$-$C_3$alkyl; y is 0 or 1; $R^{2a}$ and $R^{2b}$ are each independently hydrogen or $C_1$-$C_3$alkyl; $R^{4a}$ and $R^{4b}$ are each independently hydrogen or $C_1$-$C_3$alkyl; A is a $C_3$-$C_6$cycloalkyl selected from cyclobutyl, cyclopentyl or cyclohexyl, or A is a 5- to 6-membered heterocycloalkyl selected from tetrahydrofuranyl, tetrahydropyranyl or dihydroisoxazolyl, wherein the cyclobutyl, cyclopentyl cyclohexyl, tetrahydrofuranyl, tetrahydropyranyl or dihydroisoxazolyl are optionally substituted with one to three substituents each independently selected from halogen or $C_1$-$C_3$alkyl; and $R^3$ is —$(C(R^{10})_2)_t$—$(C_6$-$C_{10}$aryl), —$(C(R^{10})_2)_t$-(5- to 10-membered heteroaryl) or —$(C(R^{10})_2)_t$—$OR^{12}$; wherein said aryl is optionally substituted with one to five substituents each independently selected from fluoro, chloro, —$CF_3$, —$SF_5$, —$OCF_3$, —$OCHF_2$, —$OCH_3$, —$CF_2CF_3$, —$CF_2CH_3$; each $R^{12}$ is independently $C_6$-$C_{10}$aryl or a 5- to 10-membered heteroaryl, wherein said aryl or heteroaryl is optionally substituted with one to five fluoro, chloro, $CF_3$, methyl, or isopropyl; and t is 0 or 1.

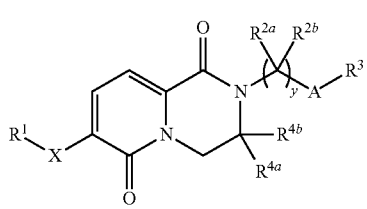

Ia

In certain embodiments of the invention, in Formula Ia as depicted above, x is imidazolyl; $R^1$ is methyl; y is 0; $R^{2a}$ and $R^{2b}$ are each independently hydrogen; $R^{4a}$ and $R^{4b}$ are each independently hydrogen; A is cyclobutyl; and $R^3$ is (6,7-difluoronaphthylen-1-yl)oxy.

In certain other embodiment of the invention, in Formula Ia as depicted above, x is imidazolyl; $R^1$ is methyl; y is 1; one of $R^{2a}$ or $R^{2b}$ is hydrogen and the other is methyl; $R^{4a}$ and $R^{4b}$ are each independently hydrogen; A is tetrahydrofuranyl; and $R^3$ is 5-trifluoromethylthiophen-2-yl.

Formula Ib depicted below is a subset of Formula I as depicted wherein x is imidazolyl, $R^3$ is phenyl, z is 1, and $R^{5a}$, $R^{5b}$, $R^6$ and $R^7$ are each hydrogen. In Formula Ib, as depicted below, $R^1$ is selected from hydrogen, halogen, or $C_1$-$C_3$alkyl; y is 0 or 1; $R^{2a}$ and $R^{2b}$ are independently hydrogen or $C_1$-$C_3$alkyl; $R^{4a}$ and $R^{4b}$ are each independently hydrogen or $C_1$-$C_3$alkyl; A is a $C_3$-$C_6$cycloalkyl selected from cyclopentyl or cyclohexyl, or A is a 5- to 6-membered heterocycloalkyl selected from tetrahydrofuranyl, tetrahydropyranyl or dihydroisoxazolyl, wherein the cyclopentyl, cyclohexyl, tetrahydrofuranyl, tetrahydropyranyl or dihydroisoxazolyl are optionally substituted with one to three substituents each independently selected from halogen or $C_1$-$C_3$alkyl; m is 1, 2, or 3; and each $R^{11}$ is independently selected from hydrogen, fluoro, chloro, —$CF_3$, —$SF_5$, —$OCF_3$, —$OCHF_2$, —$OCH_3$, —$CF_2CF_3$, —$CF_2CH_3$, or cyclopropyl.

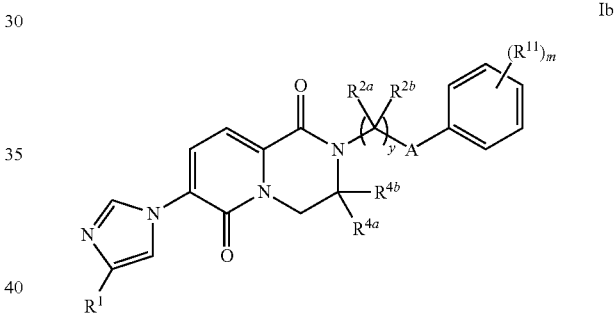

Ib

In certain embodiments of the invention, in Formula Ib as depicted above, $R^1$ is methyl; y is 1; $R^{2a}$ and $R^{2b}$ are independently hydrogen; $R^{4a}$ and $R^{4b}$ are each independently hydrogen; A is tetrahydropyranyl; m is 1; and $R^{11}$ is $CF_3$. In certain embodiments the $CF_3$ substituent is attached to the phenyl ring at the para position.

In certain embodiments of the invention, in Formula Ib as depicted above, $R^1$ is methyl; y is 1; $R^{2a}$ and $R^{2b}$ are independently hydrogen; $R^{4a}$ and $R^{4b}$ are each independently hydrogen; A is cyclohexyl; m is 1 and $R^{11}$ is chloro. In certain embodiments the chloro substituent is attached to the phenyl ring at the para position.

Formula Ic depicted below is a subset of Formula I as depicted wherein x is imidazolyl; $R^3$ is phenyl, A is tetrahydrofuranyl, z is 1, and $R^{5a}$, $R^{5b}$, $R^6$ and $R^7$ are each independently hydrogen. In Formula Ic, as depicted below, $R^1$ is selected from hydrogen, halogen, or $C_1$-$C_3$alkyl; $R^{2a}$ and $R^{2b}$ are independently hydrogen or methyl; $R^{4a}$ and $R^{4b}$ are each independently hydrogen or $C_1$-$C_3$alkyl; the tetrahydrofuranyl moiety is optionally substituted with one to three substituents each independently selected from halogen or $C_1$-$C_3$alkyl; and $R^{11}$ is selected from hydrogen, fluoro, chloro, —$CF_3$, —$SF_5$, —$OCF_3$, —$OCHF_2$, —$OCH_3$, —$CF_2CF_3$, —$CF_2CH_3$, or cyclopropyl.

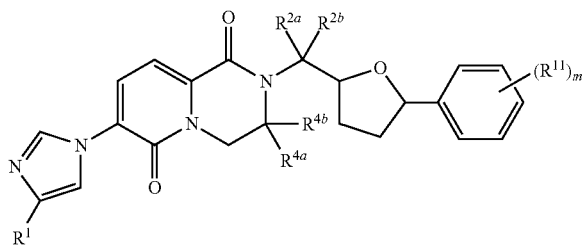

Ic

In certain other embodiments of the invention, in Formula Ic as depicted above, $R^1$ is methyl; $R^{2a}$ and $R^{2b}$ are both hydrogen; one of $R^{4a}$ and $R^{4b}$ is hydrogen and the other is methyl; and $R^{11}$ is —$CF_3$. In certain embodiments the —$CF_3$ substituent on the phenyl ring is attached at the para position.

In certain other embodiments of the invention, in Formula Ic as depicted above, $R^1$ is methyl; $R^{2a}$ and $R^{2b}$ are both hydrogen; $R^{4a}$ and $R^{4b}$ are both hydrogen; the tetrahydrofuranyl moiety is substituted with a single fluoro or methyl substituent; and $R^{11}$ is —$CF_3$. In certain embodiments the —$CF_3$ substituent on the phenyl ring is attached at the para position.

In certain other embodiments of the invention, in Formula Ic as depicted above, $R^1$ is methyl; $R^{2a}$ and $R^{2b}$ are both hydrogen; $R^{4a}$ and $R^{4b}$ are both hydrogen; and $R^{11}$ is fluoro, chloro, —$CF_3$, —$SF_5$, or —$OCH_3$.

In certain other embodiments of the invention, in Formula Ic as depicted above, $R^1$ is methyl; one of $R^{2a}$ and $R^{2b}$ is hydrogen and the other is methyl; $R^2$ is hydrogen; $R^{4a}$ and $R^{4b}$ are both hydrogen; and $R^{11}$ is fluoro, chloro, —$CF_3$, —$OCF_3$, —$OCHF_2$, or —$OCH_3$.

Formula Id depicted below is a subset of Formula I as depicted wherein x is imidazolyl, A is tetrahydrofuranyl, z is 1, and $R^{5a}$, $R^{5b}$, $R^6$ and $R^7$ are each independently hydrogen. In Formula Id depicted below, $R^2$ is hydrogen or methyl; $R^3$ is $C_6$-$C_{10}$aryl or a 5- to 6-membered heteroaryl, wherein said aryl or heteroaryl is optionally substituted with one to three $R^{11}$, wherein each $R^{11}$ is independently selected from the group consisting of fluoro, chloro, —$CF_3$, —$SF_5$, —$OCH_3$, —$OCF_3$, and —$OCHF_2$.

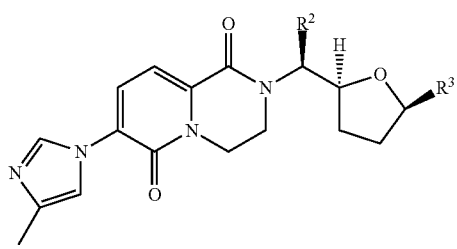

Id

In certain embodiments of Formula Id is as depicted above $R^3$ is phenyl optionally substituted with one to three $R^{11}$ substituents independently selected from fluoro, chloro, —$CF_3$, —$SF_5$, —$OCH_3$, —$OCF_3$, and —$OCHF_2$.

In certain other embodiments of Formula Id is as depicted above $R^3$ is thiophenyl optionally substituted with one to three $R^{11}$ substituents independently selected from fluoro, chloro, —$CF_3$, —$SF_5$, —$OCH_3$, —$OCF_3$, and —$OCHF_2$.

Pharmacology

Alzheimer's Disease (AD) research indicates that the disease is associated with the build-up of plaques in variable shapes and sizes in the brain. The primary plaques associated with AD are amyloid beta protein (Aβ). Aβ is produced when the amyloid protein precursor (APP) undergoes successive proteolysis by β- and γ-secretase (Haas, et al., "*Trafficking and proteolytic processing of APP*", Cold Spring Harbor Perspect Med., 2011). γ-Secretase is a large complex of four different integral proteins, one of which has been identified as the catalytic component that comprises an unusual membrane-embedded component (De Strooper, Bart, et al, "*Presenilins and γ-Secretase: Structure, Function, and Role in Alzheimer's Disease*" Cold Spring Harb Perspect Med 2012; 2:a006304). The catalytic components known as presenilins were first discovered as sites of missense mutations responsible for early-onset Alzheimer disease (AD). The encoded multipass membrane proteins were subsequently found to be the catalytic components of γ-secretases, membrane-embedded aspartyl protease complexes responsible for generating the carboxyl terminus of the amyloid b-protein (Aβ) from the amyloid protein precursor (APP). (De Strooper, Bart, et al, 2012). Accordingly, targeting γ-secretase proteins as a potential target for drug discovery in the treatment of Alzheimer's disease has become a main focus of Alzheimer's disease research.

The compounds of the present invention are γ-secretase modulators and can be used for treating conditions or diseases of the central nervous system identified to have enhanced gamma secretase activity, such as Niemann-Pick type C; neurological disorders (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorders (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorders; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders, urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I, Formula Ia, Formula Ib, and Formula Ic or a pharmaceutically acceptable salt thereof.

In certain embodiments, the compounds of the present invention can be utilized for treating a neurological disorder (such as migraine; epilepsy; Alzheimer's disease; Parkinson's disease; Niemann Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof.

Compounds of the present invention may also be useful for improving memory (both short term and long term) and learning ability.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV and that terminology and classification systems evolve with medical scientific progress.

Formulations

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronised suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a γ-secretase modulator compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-β (or fragments thereof), such as $A\beta_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W (3,5-bis(4-nitrophenoxy)benzoic acid), NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; Gamma Secretase Modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethyllne (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g. ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPOMEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxzpine, resperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN); (xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-3-fluoro-3-(3-fluoro-4-pyrrolidin-1-ylmethyl-phenyl)-cyclobutane carboxylic acid ethylamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-benzyloxy-5-((5-undecyl-2H-pyrrol-2-ylidene)methyl)-2,2'-bi-1H-pyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g. carbidopa (SINEMET, CARBILEV, PARCOPA), benserazide (MADOPAR), α-methyldopa, monofluromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (I-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, viluzole 2,3,4,9-tetrahydro-1H-carbazol-3-one oxime, desmoteplase, anatibant, astaxanthin, neuropeptide NAP (e.g. AL-108 and AL-208; both Allon Therapeutics), neurostrol, perampanel, isproniciline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADI- CUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-β-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including (a) PDE1 inhibitors (e.g. vinpocetine (CAVINTON, CERACTIN, INTELECTOL) and those disclosed in U.S. Pat. No. 6,235,742, (b) PDE2 inhibitors (e.g. erythro-9-(2-hydroxy-3-nonyl)adenine (EHNA), BAY 60-7550, and those described in U.S. Pat. No. 6,174,884), (c) PDE3 inhibitors (e.g. anagrelide, cilostazol, milrinone, olprinone, parogrelil, and pimobendan), (d) PDE4 inhibitors (e.g. apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g. sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE9 inhibitors (e.g. BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitor such as 2-[4-(1-Methyl-4-pyridin-4-yl-1H-pyrazol-3-yl)phenoxymethyl]quinoline (PF-2545920), and SCH-1518291;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, Ac-rER ($N^2$-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[2-ethyl-1(S)-(hydroxymethyl)butyl]benzenesulfonamide;

(xxxiii) serotonin (5-hydroxytryptamine) 1A (5-$HT_{1A}$) receptor antagonists, such as spiperone, levo-pindolol, BMY 7378, NAD-299, S(−)-UH-301, NAN 190, lecozotan;

(xxxiv) serotonin (5-hydroxytryptamine) 2C (5-HT2c) receptor agonists, such as vabicaserin, and zicronapine;

(xxxv) serotonin (5-hydroxytryptamine) 4 (5-$HT_4$) receptor agonists, such as PRX-03140 (Epix);

(xxxvi) serotonin (5-hydroxytryptamine) 6 (5-$HT_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, and N-((3S,4S)-4-(4-(5-cyanothiophen-2-yl)phenoxy)tetrahydrofuran-3-yl)propane-2-sulfonamide; and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

The compounds of Formula I, Formula Ia, Formula Ib and Formula Ic, or their pharmaceutically acceptable salts, may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, Formula Ia, Formula Ib, Formula Ic and Formula Id, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1

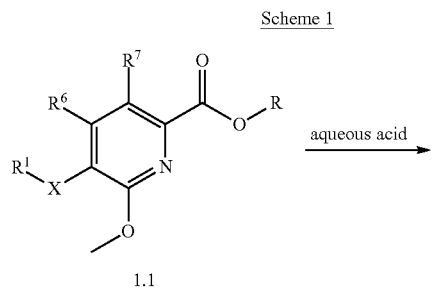

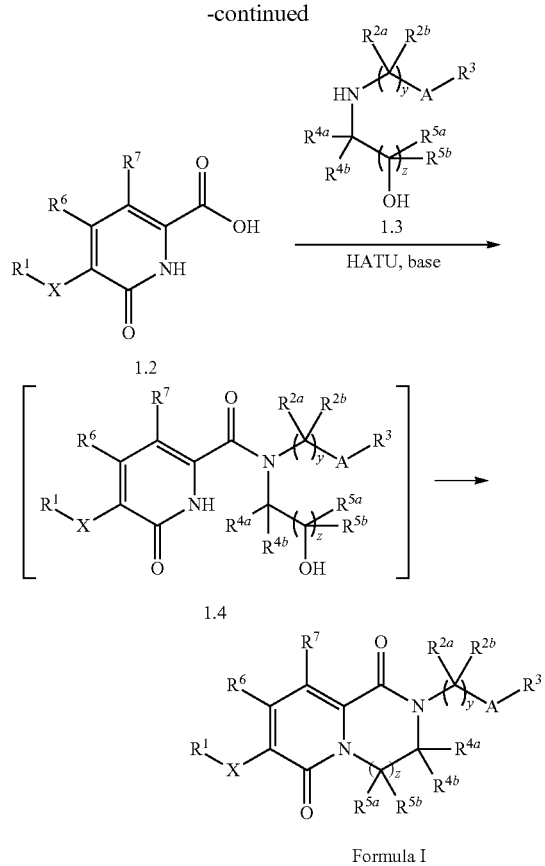

Scheme 1 illustrates a method for preparing compounds depicted by Formula I. A compound of Formula 1.1 is heated in the presence of an aqueous acid such as hydrochloric acid to furnish the corresponding pyridinone acid of Formula 1.2. The intermediate of Formula 1.2 is subjected to an amide coupling and in situ cyclization reaction with an amino alcohol of Formula 1.3 using a coupling reagent such as HATU [O-(7-azabenzotriazol-1-yl)-N,N,N',N'-tetramethyluronium hexafluorophosphate]. The reaction is carried out in the presence of a suitable base such as diisopropylethylamine and in a solvent such as dichloromethane, or N,N'-dimethylformamide.

Scheme 2

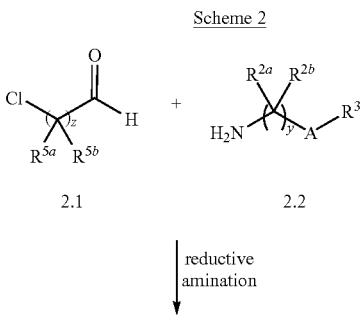

reductive amination

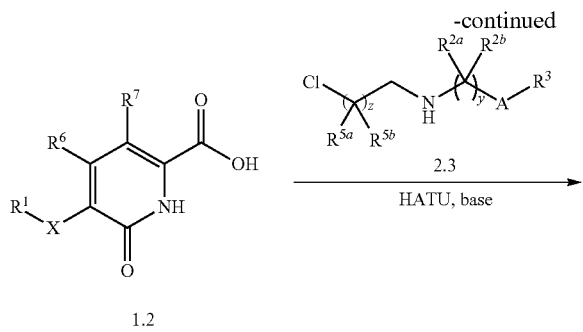
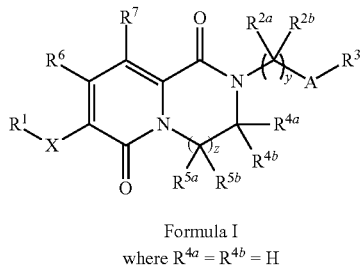

Scheme 2 illustrates a method for the preparation of compounds of Formula I. This method commences with reaction of chloroaldehyde 2.1 and an amine of Formula 2.2 using one of many reductive amination protocols known to those skilled in the art. For example, this reaction may be carried out by using a reducing agent such as sodium triacetoxyborohydride in a suitable solvent such as methanol. Following purification, the resultant chloroalkylamine 2.3 may be isolated and stored as its HCl salt. The final compound of Formula I may then be prepared by treating a mixture of chloroalkylamine 2.3, acid 1.2, and a base such as diisopropylethylamine with a suitable amide coupling reagent such as BOP-Cl [(bis(2-oxo-3-oxazolidinyl)phosphonic chloride], T3P [propylphosphonic anhydride] or HATU (preferably HATU) in a solvent such as dichloromethane.

Formula 1.3 may be prepared by carrying out a reductive amination of a ketone of Formula 3.1 with an amine of Formula 2.2 using one of many procedures well known to those skilled in the art. Another method involves reductive amination of an aldehyde of Formula 3.2 with an amine of Formula 2.2 followed by removal of the TBS protecting group by using a suitable procedure including treatment with methanolic HCl or tetrabutylammonium fluoride. Another method for the synthesis of an aminoalcohol of Formula 1.3 involves alkylation of amine 3.3 with a halide or mesylate of Formula 3.4. Yet another method involves alkylation of an amine of Formula 2.2 with bromoalcohol 3.5. Methods of synthesis for various amines 2.2, as well as alternative methods of preparation of amino alcohols 1.3, are exemplified in the Experimental Section. A person skilled in the art, utilizing these disclosures in combination with what is commonly known in the art, may further generalize those syntheses to allow access to a wide variety of amines 2.2 and amino alcohols 1.3 including but not limited to variations in $R^{2a}$, $R^{2b}$, y, alternative cycloalkyls and heterocycloalkyls A, and variously substituted aryls and heteroaryls $R^3$.

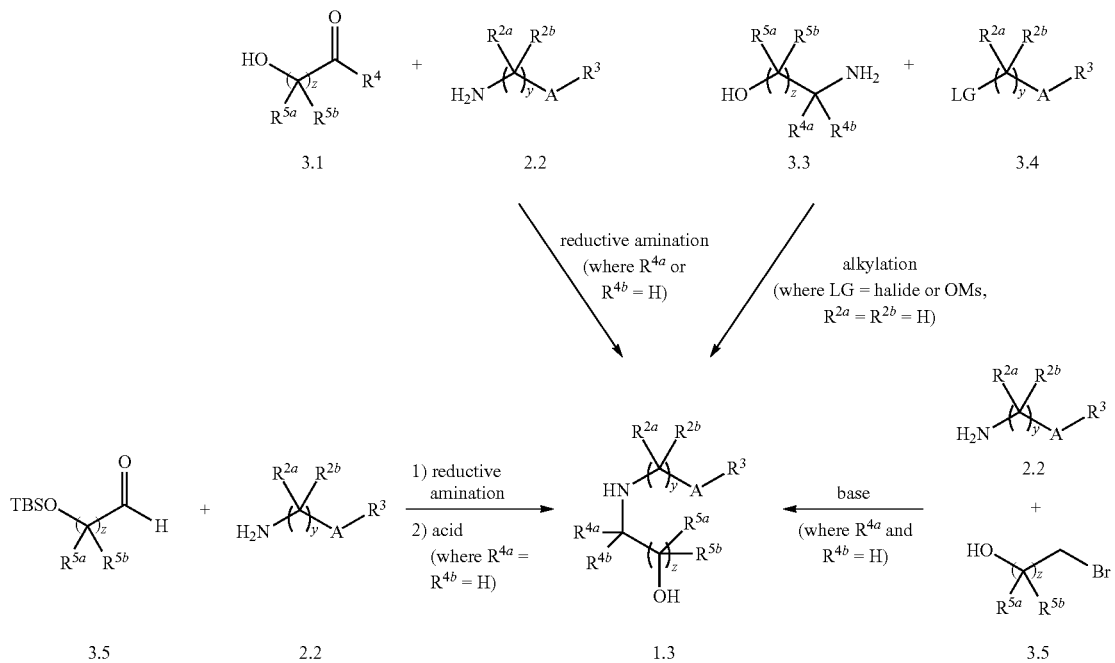

The aminoalcohol coupling partner of Formula 1.3 may be prepared via a wide variety of synthetic methods, which can readily be envisioned and developed by one skilled in the art. These include, but are not limited to, those methods illustrated in Scheme 3. For example, the aminoalcohol of Scheme 4

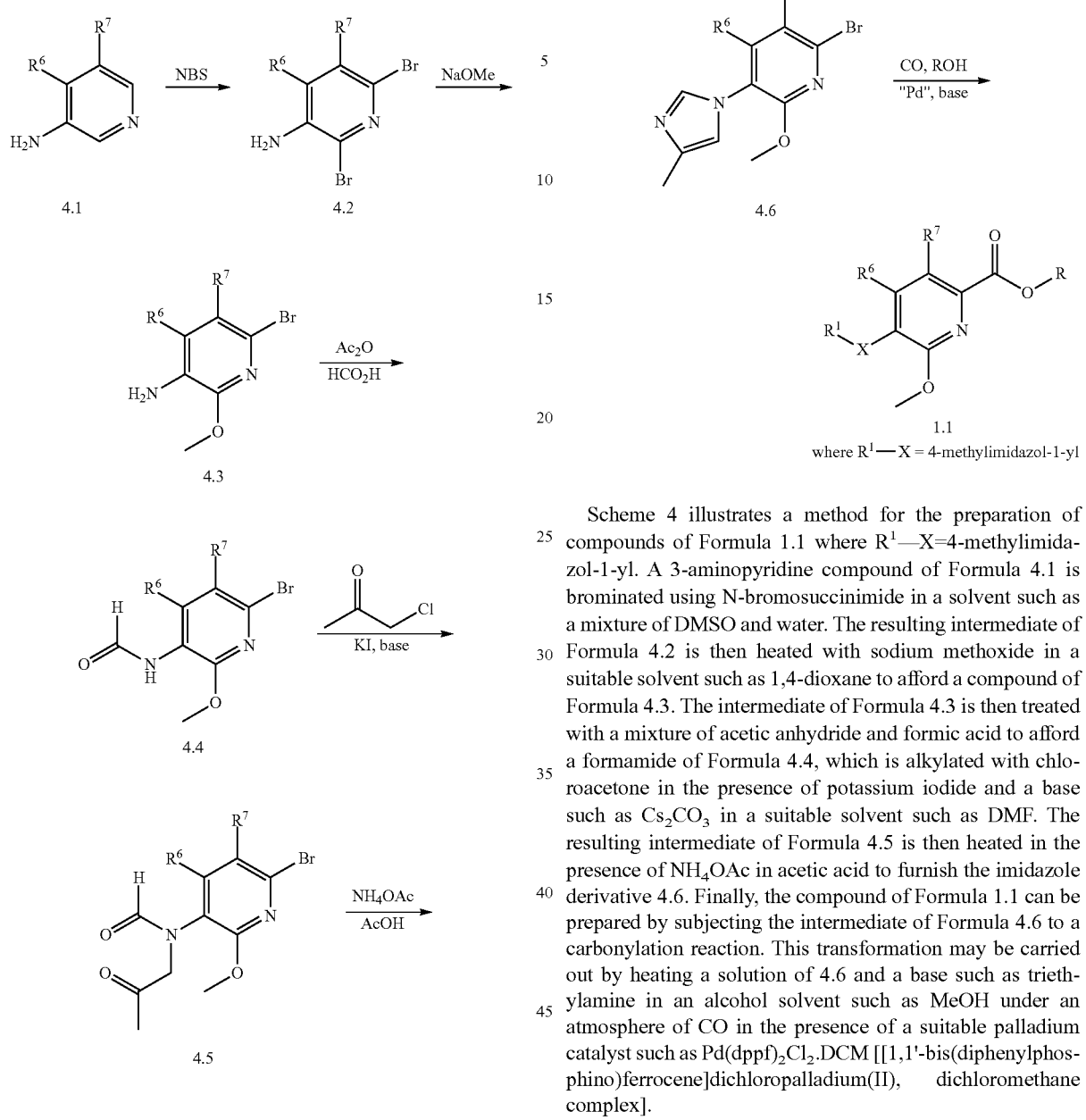

where R¹—X = 4-methylimidazol-1-yl

Scheme 4 illustrates a method for the preparation of compounds of Formula 1.1 where R¹—X=4-methylimidazol-1-yl. A 3-aminopyridine compound of Formula 4.1 is brominated using N-bromosuccinimide in a solvent such as a mixture of DMSO and water. The resulting intermediate of Formula 4.2 is then heated with sodium methoxide in a suitable solvent such as 1,4-dioxane to afford a compound of Formula 4.3. The intermediate of Formula 4.3 is then treated with a mixture of acetic anhydride and formic acid to afford a formamide of Formula 4.4, which is alkylated with chloroacetone in the presence of potassium iodide and a base such as $Cs_2CO_3$ in a suitable solvent such as DMF. The resulting intermediate of Formula 4.5 is then heated in the presence of $NH_4OAc$ in acetic acid to furnish the imidazole derivative 4.6. Finally, the compound of Formula 1.1 can be prepared by subjecting the intermediate of Formula 4.6 to a carbonylation reaction. This transformation may be carried out by heating a solution of 4.6 and a base such as triethylamine in an alcohol solvent such as MeOH under an atmosphere of CO in the presence of a suitable palladium catalyst such as $Pd(dppf)_2Cl_2$.DCM [[1,1'-bis(diphenylphosphino)ferrocene]dichloropalladium(II), dichloromethane complex].

Scheme 5

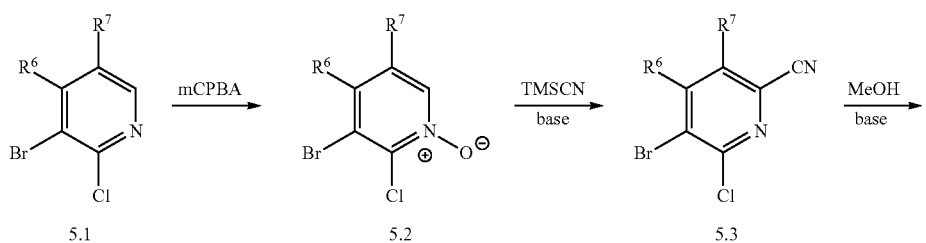

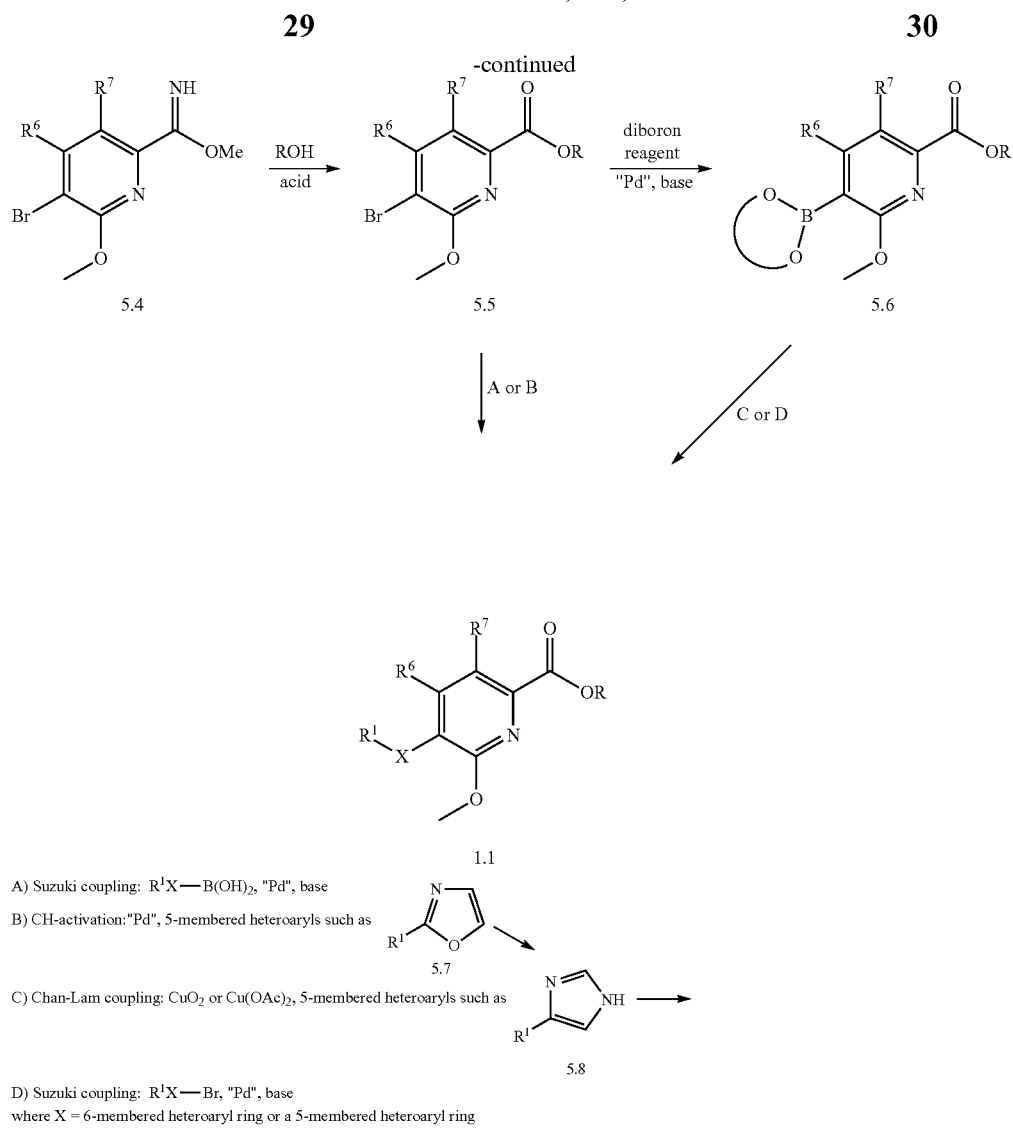

A) Suzuki coupling: $R^1X$—$B(OH)_2$, "Pd", base
B) CH-activation: "Pd", 5-membered heteroaryls such as
C) Chan-Lam coupling: $CuO_2$ or $Cu(OAc)_2$, 5-membered heteroaryls such as
D) Suzuki coupling: $R^1X$—Br, "Pd", base
where X = 6-membered heteroaryl ring or a 5-membered heteroaryl ring Scheme 5 depicts a method for the preparation of compounds of Formula 1.1. A pyridyl derivative of Formula 5.1 is oxidized with an oxidizing agent such as mCPBA [3-chloroperoxybenzoic acid] in a suitable solvent such as dichloroethane to afford the corresponding N-oxide of Formula 5.2. The intermediate of Formula 5.2 is then heated in the presence of TMSCN [trimethylsilyl cyanide] and a base such as triethylamine in a solvent such as acetonitrile to afford the intermediate of Formula 5.3. The corresponding ester may then be prepared from 5.3 in two steps by subjecting 5.3 to sodium methoxide in a solvent such as THF, followed by treatment with an alcohol and an acid such as HCl. The ester of Formula 5.5 is a versatile intermediate that allows introduction of a variety of heterocycles $R^1X$. For example, 5.5 may be subjected to a Suzuki coupling with a heteroarylboronic acid using methods well known to those skilled in the art [see *Tetrahedron* 2002, 58, 9633-9695]. Alternatively, the compound of Formula 5.5 may be coupled to a heterocycle X using a direct arylation approach [see D. Lapointe et al., *J. Org. Chem.* 2011, 76, 749-759, and references therein]. For example, 5.5 may be coupled to 2-methyl-1,3-oxazole [Formula 5.7 where $R^1$=Me] by heating in the presence of a suitable palladium catalyst such as allylpalladium chloride dimer and a base such as $K_2CO_3$ in a solvent such as 1,4-dioxane to afford the intermediate of Formula 1.1 where $R^1X$=2-methyl-1,3-oxazol-5-yl.

Alternatively, the compound of Formula 5.5 may be converted to the corresponding boronate 5.6, using a palladium-catalyzed cross coupling with a diboron reagent such as 5,5,5',5'-tetramethyl-2,2'-bi-1,3,2-dioxaborinane in the presence of potassium acetate and a palladium catalyst such as $Pd(dppf)_2Cl_2.DCM$ in a solvent such as 1,4-dioxane. The resulting boronate intermediate of Formula 5.6 can in turn be subjected to a Suzuki coupling with a heteroaryl halide to afford the final compound of Formula 1.1. Another method for the introduction of a heterocycle X involves the use of a Chan-Lam coupling [see *Tetrahedron Lett.* 2003, 44, 3863-3865, and *Synthesis* 2008, 5, 795-799]. For example, 5.6 may be coupled to substituted imidazole 5.8 by heating with a suitable copper source such as copper oxide or copper acetate in a solvent such as methanol in the presence of air to afford the intermediate of Formula 1.1 where X=imidazol-1-yl.

Scheme 6

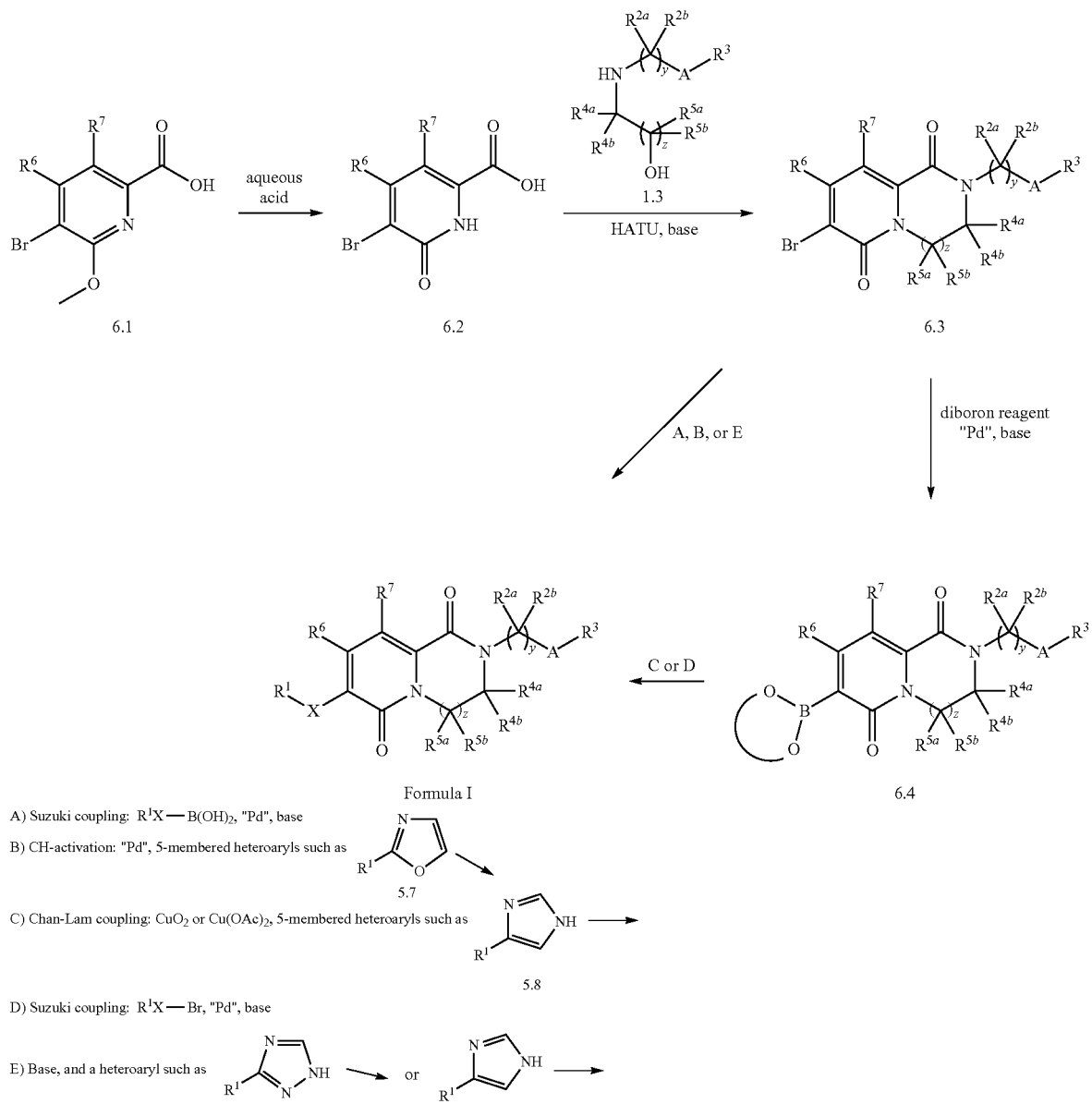

Scheme 6 illustrates a method for the synthesis of compounds of Formula I. The method commences by heating the compound of Formula 6.1 in an acid such as hydrochloric acid to afford pyridinone acid intermediate 6.2. The acid of Formula 6.2 may be subjected to a coupling/cyclization reaction with an aminoalcohol of Formula 1.3 to afford an intermediate of Formula 6.3 using chemistry described in Scheme 1. The final compound, Formula I, may then be formed directly from 6.3 or via boronate 6.4 using the strategies discussed in Scheme 5. Alternatively, compounds of Formula I where heterocycle X is linked to the pyridinone ring via a C—N bond may be formed by nucleophilic aromatic substitution. For example, triazole 6.5 may be coupled to 6.3 by heating in the presence of a base such as $K_2CO_3$ and a solvent such as DMSO to afford the final compound of Formula I where X=triazol-1-yl.

Scheme 7

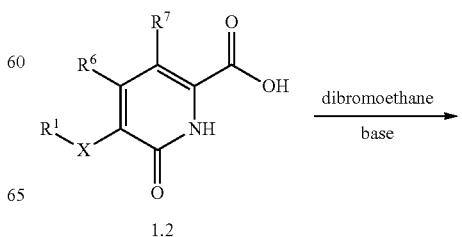

-continued

Scheme 8

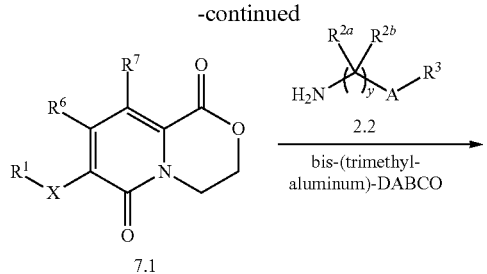

7.1

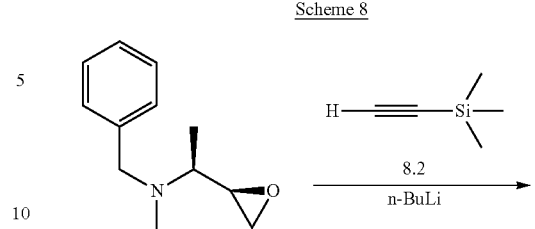

8.1

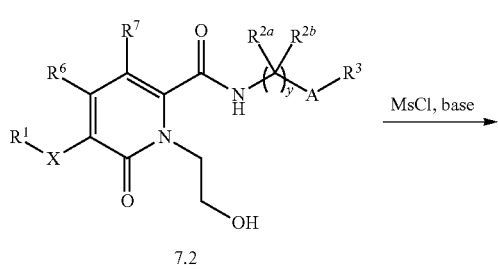

7.2

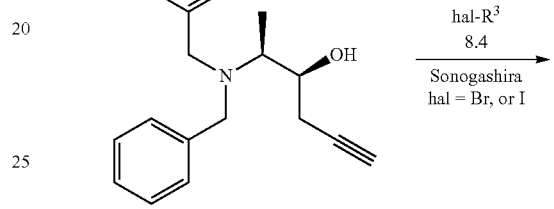

8.3

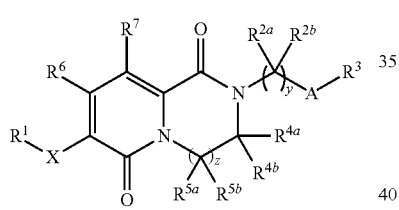

Formula I,
where z = 1, and $R^{4a} = R^{4b} = R^{5a} = R^{5b} = H$

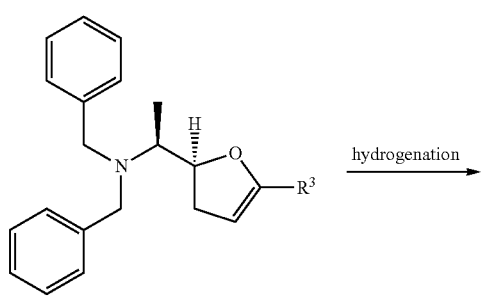

8.5

8.6

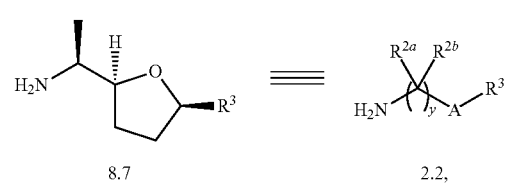

8.7

2.2,
where y = 1,
$R^{2a}$ = CH$_3$, $R^{2b}$ = H, A = tetrahydrofuranyl, and $R^3$ = aryl or heteroaryl Scheme 7 illustrates a method for the synthesis of compounds of Formula I where z=1 and $R^{4a}=R^{4b}=R^{5a}=R^{5b}=H$. The method involves heating a mixture of a compound of Formula 1.2, dibromoethane, and a base such as Cs$_2$CO$_3$ in a solvent such as DMF to afford lactone intermediate 7.1. The lactone of Formula 7.1 may then be reacted with an amine of Formula 2.2 in the presence of a reagent such as DIBAL (diisobutylaluminum hydride) or bis(trimethylaluminum)-1,4-diazabicyclo[2.2.2]octane adduct in a solvent such as THF to afford the amide alcohol of Formula 7.2. This intermediate, in turn, may be reacted with methanesulfonyl chloride in the presence of a base such as triethylamine in a solvent such as THF followed by treatment with a base such as 1,3,4,6,7,8-hexahydro-2H-pyrimido[1,2-a]pyrimidine to afford the compound of Formula I wherein z=1 and $R^{4a}=R^{4b}=R^{5a}=R^{5b}=H$. Alternatively, the ring closure may be carried out in a stepwise fashion by first converting alcohol 7.2 into the corresponding chloride by treatment with thionyl chloride, followed by deprotonation of the amide NH with a suitable base such as lithium bis(trimethylsilyl)amide to afford the final compound Formula I.

Scheme 8 illustrates a method for the synthesis of amines of Formula 8.7, which represent a subset of the general structure of Formula 2.2. The synthesis commences with deprotonation of ethynyl(trimethyl)silane using a suitable base such as n-butyllithium in a solvent such as THF. This mixture is then added to a solution of an epoxide of Formula 8.1 (see J. Barluenga et al., *J. Org. Chem.* 1995, 60, 6696-6699) in a solvent such as THF. The resultant alkyne of Formula 8.3 may then be subjected to a Sonogashira coupling with an aryl or heteroaryl halide of Formula 8.4 (where hal=bromine or iodine) using standard conditions known to those skilled in the art (see R. Chinchilla et al., *Chem. Soc. Rev.* 2011, 40, 5084-5121) to afford a compound of Formula 8.5. This intermediate is then subjected to a cyclization reaction mediated by a platinum catalyst such as di-µ-chlorodichlorobis(ethylene)diplatinum(II) and an acid such as trifluoroacetic acid in a solvent such as $CH_2Cl_2$ to afford a dihydrofuran intermediate of Formula 8.6. Finally, transfer hydrogenation using ammonium formate and a suitable catalyst such as palladium hydroxide on carbon in a solvent such as methanol affords amine 8.7, which is subset of Formula 2.2, wherein y=1, $R^{2a}$=$CH_3$, $R^{2b}$=H, A=tetrahydrofuranyl, and $R^3$=aryl or heteroaryl.

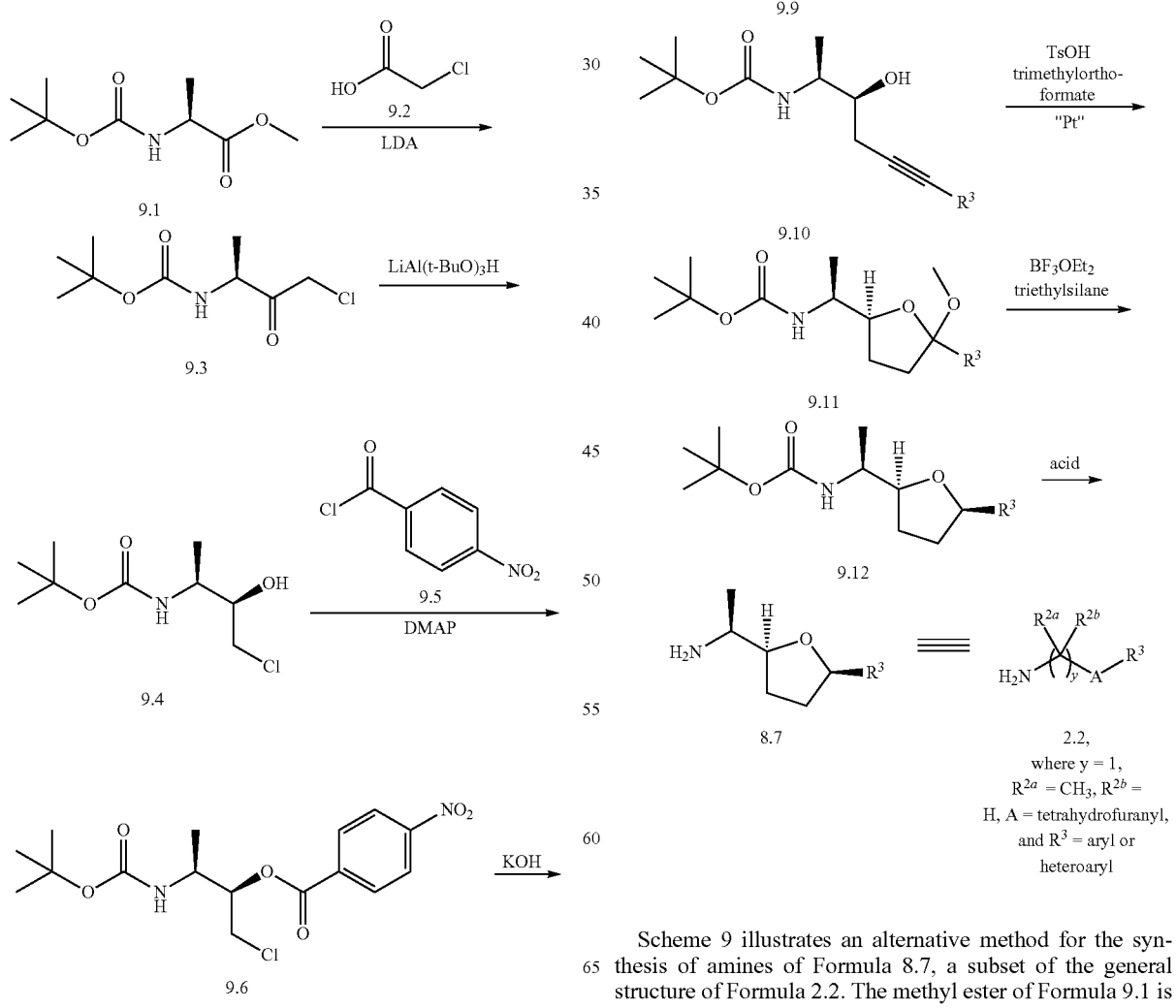

Scheme 9 illustrates an alternative method for the synthesis of amines of Formula 8.7, a subset of the general structure of Formula 2.2. The methyl ester of Formula 9.1 is reacted with the dianion resulting from deprotonation of chloroacetic acid (9.2) with a suitable base such as LDA in a solvent such as THF. The resulting α-chloroketone of Formula 9.3 is then treated with a suitable reducing agent such as lithium tri-tert-butoxyaluminum hydride in a solvent such as diethyl ether to afford chlorohydrin 9.4, which in turn may be converted to the p-nitrobenzoate 9.6 by acylation with p-nitrobenzoyl chloride (9.5) in the presence of DMAP [4-(dimethylamino)pyridine] and a base such as triethylamine in a solvent such as dichloromethane. The intermediate of Formula 9.6 is then treated with a base such as potassium hydroxide, resulting in the formation of an epoxide of Formula 9.7. In analogy with Scheme 8, epoxide 9.7 may be subjected to ring opening with the acetylide resulting from deprotonation of 8.2 with a base such as n-butyllithium in the presence of dimethylaluminum chloride in a solvent such as toluene to afford the alkyne of Formula 9.8. This intermediate, in turn, is then subjected to removal of the trimethylsilyl group by exposure to a protic solvent such as methanol and a base such as potassium carbonate to deliver the deprotected alkyne 9.9. This intermediate is then subjected to a Sonogashira coupling with aryl halide 8.4, as described in Scheme 8, to afford the intermediate of Formula 9.10. This intermediate is then subjected to a cyclization reaction mediated by a platinum catalyst such as di-μ-chlorodichlorobis(ethylene)diplatinum (II), an acid such as p-toluenesulfonic acid, and trimethyl orthoformate in a solvent such as MeOH to afford the compound of Formula 9.11. Treatment of 9.11 with boron trifluoride diethyl etherate and a reducing agent such as triethylsilane in a suitable solvent such as dichloromethane delivers the tetrahydrofuran of Formula 9.12. Finally, removal of the Boc protecting group by exposure to an acid such as trifluoroacetic acid or hydrochloric acid in a solvent such as dichloromethane or 1,4-dioxane provides amine 8.7, which is a subset of Formula 2.2 wherein y=1, $R^{2a}$=CH$_3$, $R^{2b}$=H, A=tetrahydrofuranyl, and $R^3$=aryl or heteroaryl.

When intermediates used to synthesize compounds of the present invention incorporate a basic center their suitable acid addition salts may be employed in synthetic pathways. Such suitable addition salts include but are not limited to those derived from inorganic acids, such as hydrochloric, hydrobromic, hydrofluoric, hydroiodic, boric, fluoroboric, phosphoric, nitric, carbonic, and sulfuric acids, and organic acids such as acetic, benzenesulfonic, benzoic, ethanesulfonic, fumaric, lactic, maleic, methanesulfonic, trifluoromethanesulfonic, succinic, toluenesulfonic, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, lactate, maleate, fumarate, benzoate, p-hydroxybenzoate, phenylacetate, mandelate, methanesulfonate, ethanesulfonate, benzenesulfonate, toluenesulfonate, adipate, butyrate, camphorate, cyclopentanepropionate, dodecylsulfate, heptanoate, hexanoate, nicotinate, 2-naphthalenesulfonate, oxalate, 3-phenylpropionate, pivalate, and undecanoate.

Furthermore, where intermediates used to prepare compounds of the invention carry an acidic moiety, suitable salts thereof may be employed for synthesis. Such salts include alkali metal salts, i.e., lithium, sodium or potassium salts; alkaline earth metal salts, e.g., calcium or magnesium salts; and salts formed with suitable organic ligands such as amines or quaternary ammonium cations. Organic salts of such acidic intermediates may be made from primary, secondary or tertiary amines such as methylamine, diethylamine, ethylenediamine or trimethylamine. Quaternary amines may be prepared by reaction of tertiary amines with agents such as lower alkyl(C$_1$-C$_6$) halides (e.g., methyl, ethyl, propyl, and butyl chlorides, bromides, and iodides), dialkyl sulfates (i.e., dimethyl, diethyl, dibutyl, and diamyl sulfates), arylalkyl halides (i.e., benzyl and phenethyl bromides), and others.

Experimental Procedures and Working Example

The following illustrate the synthesis of various compounds of the present invention. Additional compounds within the scope of this invention may be prepared using the methods illustrated in these Examples, either alone or in combination with techniques generally known in the art.

It will be understood that the intermediate compounds of the invention depicted above are not limited to the particular enantiomer shown, but also include all stereoisomers and mixtures thereof.

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate R$_f$s or retention times.

Preparations

Preparation P1: 5-(4-Methyl-1H-imidazol-1-yl)-6-oxo-1,6-dihydropyridine-2-carboxylic acid, hydrobromide salt (P1)

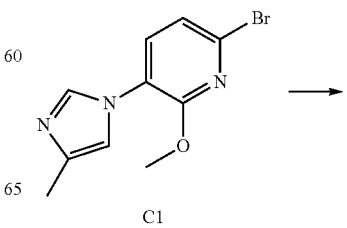

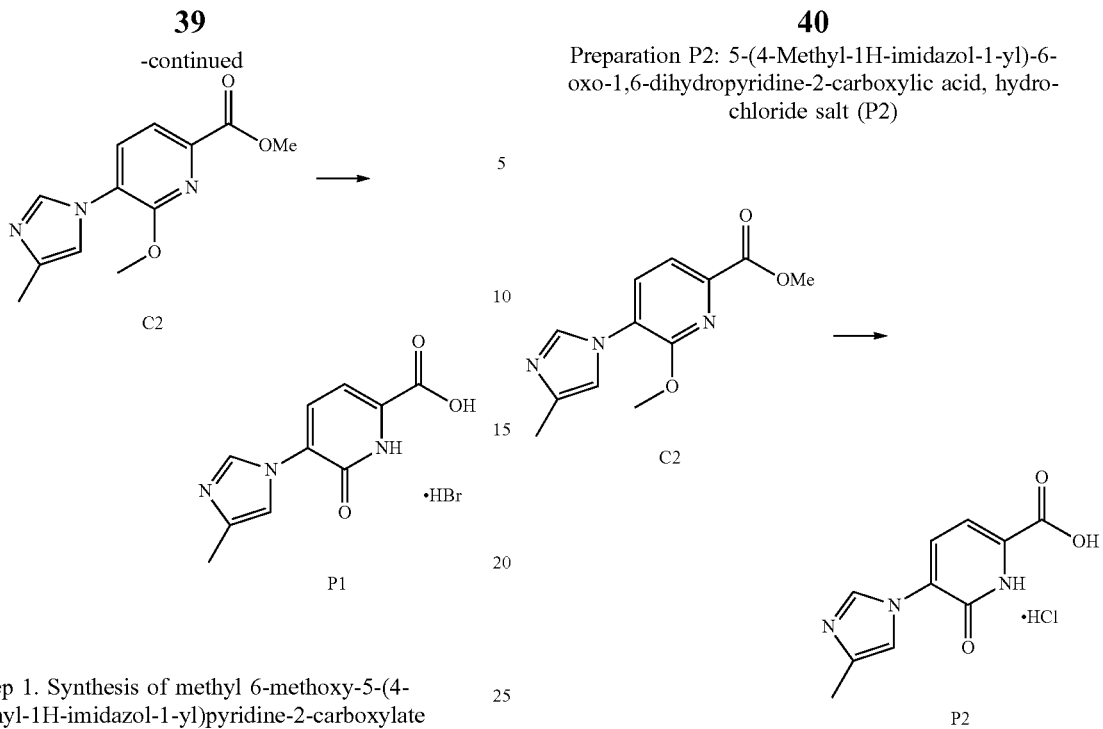

Step 1. Synthesis of methyl 6-methoxy-5-(4-methyl-1H-imidazol-1-yl)pyridine-2-carboxylate (C2)

To a solution of the known 6-bromo-2-methoxy-3-(4-methyl-1H-imidazol-1-yl)pyridine (C1, T. Kimura et al., U.S. Pat. Appl. Publ. 2009, US 20090062529 A1) (44.2 g, 165 mmol) in methanol (165 mL) was added triethylamine (46 mL, 330 mmol) and [1,1'-bis(diphenylphosphino)ferrocene]dichloropalladium(II), dichloromethane complex (6.7 g, 8.2 mmol). The mixture was degassed several times with nitrogen. The reaction was heated to 70° C. under CO atmosphere (3 bar) in a Parr apparatus. After 30 minutes, the pressure dropped to 0.5 bar; additional CO was added until the pressure stayed constant for a period of 30 minutes. The mixture was allowed to cool to room temperature and filtered through a pad of Celite. The Celite pad was washed twice with methanol and the combined filtrates were concentrated under reduced pressure. The residue (88 g) was dissolved in ethyl acetate (1 L) and water (700 mL); the organic layer was washed with water (200 mL), and the aqueous layer was extracted with ethyl acetate (500 mL). The combined organic layers were dried over magnesium sulfate, filtered and concentrated to provide the title compound. Yield: 42.6 g, quantitative.

Step 2. Synthesis of 5-(4-methyl-1H-imidazol-1-yl)-6-oxo-1,6-dihydropyridine-2-carboxylic acid, hydrobromide salt (P1)

A solution of C2 (3.82 g, 15.9 mmol) in acetic acid (30 mL) and aqueous hydrobromic acid (48%, 30 mL) was heated at reflux for 4 hours. The reaction was allowed to cool to room temperature, and then chilled in an ice bath; the resulting precipitate was collected via filtration and washed with ice water (30 mL). Recrystallization from ethanol (20 mL) provided the title compound as a light yellow solid. Yield: 3.79 g, 12.6 mmol, 79%. LCMS m/z 220.1 (M+1). $^1$H NMR (400 MHz, DMSO-$d_6$) δ 12.6 (v br s, 1H), 9.58-9.60 (m, 1H), 8.07 (d, J=7.6 Hz, 1H), 7.88-7.91 (m, 1H), 7.09 (d, J=7.4 Hz, 1H), 2.34 (br s, 3H).

Preparation P2: 5-(4-Methyl-1H-imidazol-1-yl)-6-oxo-1,6-dihydropyridine-2-carboxylic acid, hydrochloride salt (P2)

A mixture of C2 (12.8 g, 51.8 mmol) and 37% hydrochloric acid (25 mL) was heated at reflux for 18 hours. After the reaction mixture had cooled to room temperature, the solid was collected via filtration; it was stirred with 1,4-dioxane (2×20 mL) and filtered again, to afford the product as a yellow solid. Yield: 13 g, 51 mmol, 98%. $^1$H NMR (400 MHz, CD$_3$OD) δ 9.52 (br s, 1H), 8.07 (d, J=7.5 Hz, 1H), 7.78 (br s, 1H), 7.21 (d, J=7.5 Hz, 1H), 2.44 (s, 3H).

Preparation P3: 7-(4-Methyl-1H-imidazol-1-yl)-3,4-dihydropyrido[2,1-c][1,4]oxazine-1,6-dione (P3)

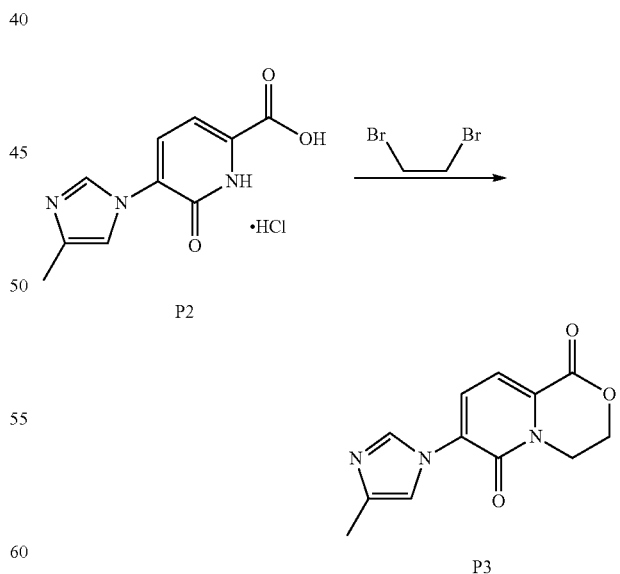

Compound P2 (65 g, 250 mmol), 1,2-dibromoethane (52.5 g, 280 mmol) and cesium carbonate (124 g, 381 mmol) were combined in N,N-dimethylformamide (850 mL) and heated at 90° C. for 6 hours. The reaction mixture was then cooled and filtered through Celite. After concentration of the filtrate in vacuo, the residue was dissolved in dichloromethane (500 mL), washed with saturated aqueous sodium chloride solution (100 mL), washed with water (50 mL), dried over magnesium sulfate, filtered, and concentrated under reduced pressure. The resulting solid was washed with acetonitrile to provide the product. Yield: 46.5 g, 190 mmol, 76%. $^1$H NMR (400 MHz, CDCl$_3$) δ 8.33 (d, J=1.4 Hz, 1H), 7.43 (AB quartet, J$_{AB}$=7.7 Hz, Δv$_{AB}$=33.4 Hz, 2H), 7.15-7.17 (m, 1H), 4.66-4.70 (m, 2H), 4.38-4.42 (m, 2H), 2.30 (d, J=0.8 Hz, 3H).

Preparation P4: 2-({cis-2-[2-(Trifluoromethyl)phenoxy]cyclobutyl}amino)ethanol (P4)

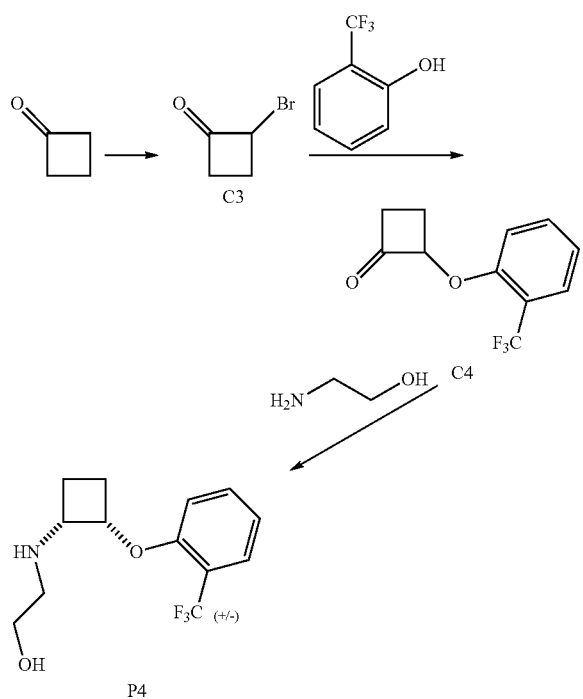

Step 1. Synthesis of 2-bromocyclobutanone (C3)

A solution of cyclobutanone (1.28 mL, 17.1 mmol) in chloroform (20 mL) at 0° C. was treated drop-wise with bromine (0.88 mL, 17 mmol) over 25 minutes, warmed to room temperature and stirred for 16 hours. Dichloromethane (100 mL) was added and the solution was washed with aqueous sodium thiosulfate solution (50 mL) and saturated aqueous sodium chloride solution (50 mL). The organic layer was dried over magnesium sulfate and concentrated in vacuo to afford the title compound as a colorless oil. Yield: 2.45 g, 16.4 mmol, 96%. $^1$H NMR (400 MHz, CDCl$_3$) δ 4.97-5.04 (m, 1H), 3.16-3.24 (m, 2H), 2.69-2.80 (m, 1H), 2.18-2.30 (m, 1H).

Step 2. Synthesis of 2-[2-(trifluoromethyl)phenoxy]cyclobutanone (C4)

A solution of 2-(trifluoromethyl)phenol (2.72 g, 16.8 mmol) in acetone (147 mL) at 0° C. was treated with cesium carbonate (5.47 g, 16.8 mmol), followed by drop-wise addition of C3 (2.5 g, 16.8 mmol). The mixture was stirred at 0° C. for 1.5 hours, filtered through Celite, and concentrated in vacuo to afford the title compound as a colorless oil. Yield: 3.5 g, 15 mmol, 89%. $^1$H NMR (400 MHz, CDCl$_3$) δ 7.56 (br d, J=7.7 Hz, 1H), 7.45-7.50 (m, 1H), 7.14 (d, J=8.3 Hz, 1H), 7.07 (br dd, J=7.6, 7.6 Hz, 1H), 5.31-5.37 (m, 1H), 2.92-3.00 (m, 2H), 2.55-2.66 (m, 1H), 2.19-2.30 (m, 1H).

Step 3. Synthesis of 2-({cis-2-[2-(trifluoromethyl)phenoxy]cyclobutyl}amino)ethanol (P4)

A solution of C4 (3.5 g, 15 mmol) and 2-aminoethanol (1.03 g, 16.8 mmol) in 1,2-dichloroethane (100 mL) was treated with sodium triacetoxyborohydride (5.62 g, 25.2 mmol) and stirred at room temperature for 2 hours. The reaction was treated with acetic acid (4 mL) and stirred at room temperature for 16 hours. Aqueous sodium hydroxide solution (1 N, 100 mL) was added and the mixture was extracted with dichloromethane (2×100 mL). The combined organic layers were dried over magnesium sulfate and concentrated in vacuo. Purification via silica gel chromatography (Gradient: 0% to 70% [10% 2 N ammonia in methanol/90% ethyl acetate] in ethyl acetate) afforded the title compound as a light amber oil. Yield: 2.1 g, 7.6 mmol, 51%. The indicated cis stereochemistry was tentatively assigned, based on NOE (nuclear Overhauser enhancement) experiments. $^1$H NMR (400 MHz, CDCl$_3$) δ 7.57 (br dd, J=7.7, 1.3 Hz, 1H), 7.41-7.47 (m, 1H), 6.99 (br dd, J=7.6, 7.6 Hz, 1H), 6.80 (d, J=8.2 Hz, 1H), 4.88-4.93 (m, 1H), 3.54-3.66 (m, 3H), 2.81-2.88 (m, 1H), 2.63-2.70 (m, 1H), 2.22-2.31 (m, 1H), 1.97-2.16 (m, 2H), 1.86-1.94 (m, 1H).

Preparation P5: 2-({[3-(4-Chlorophenyl)cyclohexyl]methyl}amino)ethanol (P5)

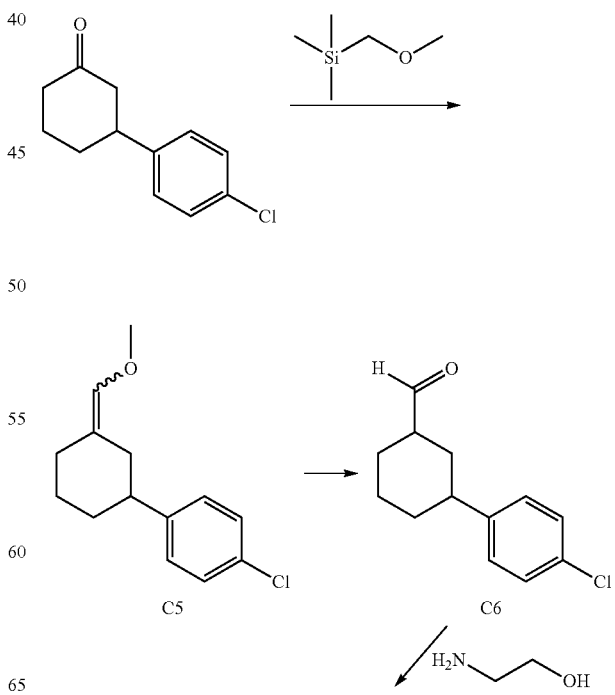

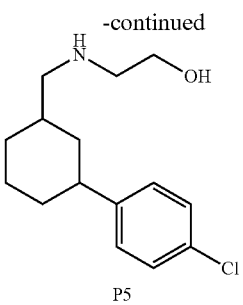

P5

Step 1. Synthesis of 1-chloro-4-[3-(methoxymethyl-idene)cyclohexyl]benzene (C5)

To a solution of (methoxymethyl)trimethylsilane (694 mg, 5.75 mmol) in tetrahydrofuran (6.8 mL) at −78° C. was added drop-wise sec-butyllithium (1.4 M, 4.45 mL, 6.23 mmol). The solution was warmed to −25° C., held at that temperature for 30 minutes, then cooled to −78° C. To the reaction was added drop-wise 3-(4-chlorophenyl)cyclohexanone (prepared according to the method of G. A. Whitlock et al., *Bioorg. Med. Chem. Lett.* 2009, 19, 3118-3121) (1.0 g, 4.8 mmol). The reaction was warmed to −25° C. and stirred for 30 minutes, then allowed to slowly warm to room temperature and stir for 48 hours. The reaction was diluted with tetrahydrofuran (10 mL), quenched with saturated aqueous ammonium chloride solution, and extracted three times with ethyl acetate. The combined organic layers were dried over magnesium sulfate and concentrated in vacuo to provide the crude title compound as a pale yellow oil. Yield: 1.25 g. This material was used directly in the following step. GCMS m/z 236 (M+).

Step 2. Synthesis of 3-(4-chlorophenyl)cyclohexanecarbaldehyde (C6)

Crude C5 (1.25 g from the preceding step, ≤4.8 mmol) was dissolved in aqueous formic acid (3 M, 2.0 mL) and the mixture was refluxed for 2 hours. The solution was cooled to room temperature, diluted with water and extracted twice with ethyl acetate; the combined organic layers were dried over sodium sulfate and concentrated in vacuo. Silica gel chromatography (Gradient: 0% to 100% ethyl acetate in heptanes) afforded the title compound as an oil, presumed by $^1$H NMR to be a roughly 4:1 mixture of the two stereoisomers. Yield: 338 mg, 1.52 mmol, 32% over two steps. GCMS m/z 222 (M+). $^1$H NMR (400 MHz, CDCl$_3$) δ [9.65 (d, J=1.4 Hz) and 9.79 (br s), total 1H], 7.25-7.30 (m, 2H), 7.12-7.18 (m, 2H), 1.21-2.66 (m, 10H).

Step 3. Synthesis of 2-({[3-(4-chlorophenyl)cyclohexyl]methyl}amino)ethanol (P5)

To a solution of C6 (338 mg, 1.52 mmol) in methanol (5 mL) was added 2-aminoethanol (139 mg, 2.28 mmol) followed by acetic acid (89 µL, 1.55 mmol). The reaction was stirred at reflux for 2 hours, then cooled to 0° C. Sodium borohydride (115 mg, 3.04 mmol) was added and the mixture was allowed to warm to room temperature. The reaction was diluted with ethyl acetate, quenched with water, and then extracted three times with ethyl acetate. The combined organic layers were dried over sodium sulfate and concentrated in vacuo to provide the crude title compound as a liquid. Yield: 362 mg, 1.35 mmol, 89%. This was presumed to be a mixture of stereoisomers. LCMS m/z 268.3 (M+1). $^1$H NMR (400 MHz, CDCl$_3$), characteristic peaks: δ 7.22-7.28 (m, 2H), 7.10-7.16 (m, 2H), 3.63 (dd, J=5.3, 5.1 Hz, 2H), 2.75 (dd, J=5.3, 5.1 Hz, 2H).

EXAMPLES

Example 1

7-(4-Methyl-1H-imidazol-1-yl)-2-{trans-2-[2-(trifluoromethyl)phenoxy]cyclobutyl}-3,4-dihydro-2H-pyrido[1,2-a]pyrazine-1,6-dione, trifluoroacetate salt (1)

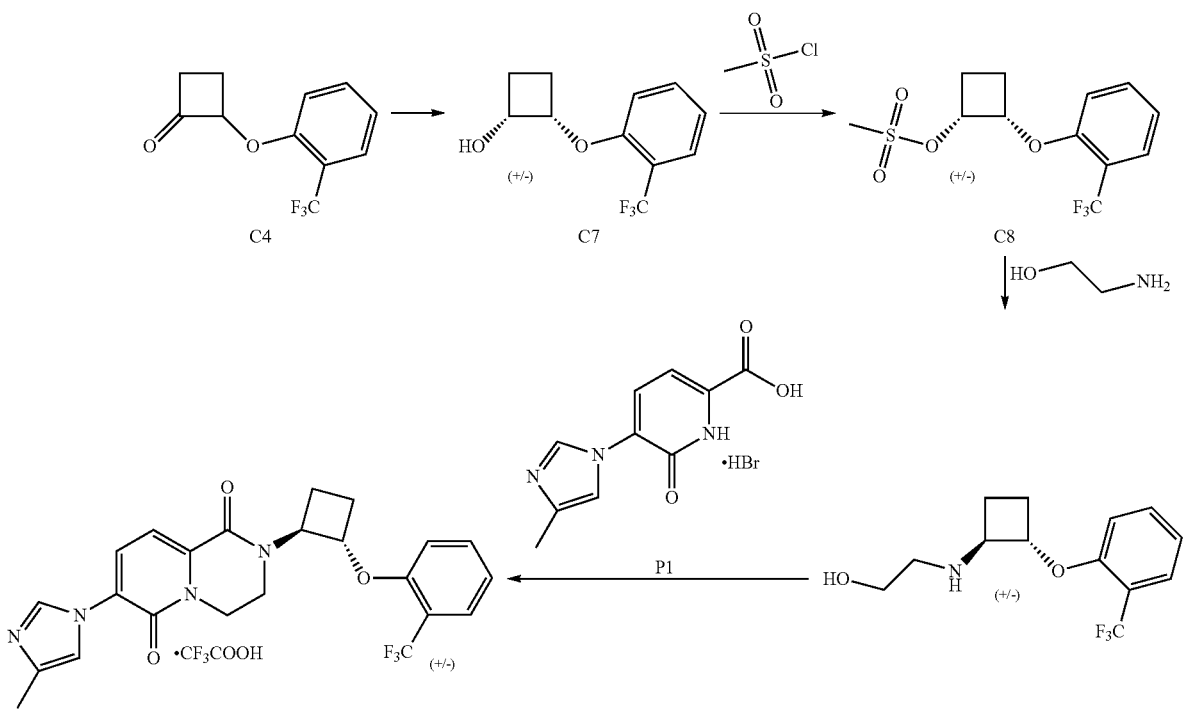

Step 1. Synthesis of cis-2-[2-(trifluoromethyl)phenoxy]cyclobutanol (C7)

Compound C4 (3.00 g, 13.0 mmol) was dissolved in methanol (100 mL) and cooled to −78° C. Sodium borohydride (1.48 g, 39.1 mmol) was added portion-wise over 10 minutes, and the mixture was stirred at −78° C. for an additional 30 minutes before being allowed to warm to room temperature and stir for 1 hour. The reaction was quenched with saturated aqueous sodium bicarbonate solution (100 mL) and extracted with dichloromethane (2×150 mL). The organic layers were combined, washed with saturated aqueous sodium chloride solution (100 mL), dried over magnesium sulfate, filtered and concentrated under reduced pressure. Two purifications via silica gel chromatography [Gradients: 1) 0% to 50% ethyl acetate in heptane; 2) 0% to 50% dichloromethane in heptane] provided the title compound as a colorless oil. The product was tentatively assigned cis stereochemistry on the basis of NOE studies. Yield: 650 mg, 2.80 mmol, 22%. $^1$H NMR (400 MHz, CDCl$_3$) δ 7.60 (br dd, J=7.8, 1.2 Hz, 1H), 7.47 (br ddd, J=8.2, 7.8, 1.2 Hz, 1H), 7.04 (br dd, J=7.6, 7.6 Hz, 1H), 6.87 (br d, J=8.4 Hz, 1H), 4.86-4.91 (m, 1H), 4.45-4.53 (m, 1H), 2.75 (d, J=9.2 Hz, 1H), 2.27-2.36 (m, 1H), 2.02-2.22 (m, 3H).

Step 2. Synthesis of cis-2-[2-(trifluoromethyl)phenoxy]cyclobutyl methanesulfonate (C8)

A mixture of C7 (484 mg, 2.08 mmol), triethylamine (0.87 mL, 6.3 mmol) and dichloromethane (30 mL) was cooled to 0° C. and methanesulfonyl chloride (0.32 mL, 4.2 mmol) was added drop-wise over 15 minutes. After an additional 30 minutes at 0° C., the reaction was quenched with saturated aqueous sodium bicarbonate solution (50 mL), and the mixture was extracted with dichloromethane (2×50 mL). The combined organic layers were washed with saturated aqueous sodium chloride solution (50 mL), dried over magnesium sulfate, filtered and concentrated in vacuo to provide the title compound as a colorless oil. Yield: 640 mg, 2.06 mmol, 99%. $^1$H NMR (400 MHz, CDCl$_3$) δ 7.60 (br dd, J=7.8, 1.2 Hz, 1H), 7.45-7.51 (m, 1H), 7.06 (br dd, J=7.7, 7.6 Hz, 1H), 6.88 (br d, J=8.4 Hz, 1H), 5.26-5.32 (m, 1H), 5.01-5.06 (m, 1H), 2.95 (s, 3H), 2.53-2.63 (m, 1H), 2.37-2.46 (m, 1H), 2.18-2.30 (m, 2H).

Step 3. Synthesis of 2-({trans-2-[2-(trifluoromethyl)phenoxy]cyclobutyl}amino)ethanol (C9)

A mixture of C8 (500 mg, 1.61 mmol) and 2-aminoethanol (5 mL) was heated at 90° C. for 18 hours, then at 100° C. for an additional 24 hours. The reaction was cooled, diluted with ethyl acetate (100 mL) and washed with aqueous sodium hydroxide solution (1 M, 5×50 mL). The organic layer was dried over magnesium sulfate, filtered and concentrated in vacuo. Purification via HPLC (Column: Phenomenex Luna C18(2), 5 μm; Mobile phase A: 0.1% formic acid in water; Mobile phase B: 0.1% formic acid in methanol; Gradient: 5% to 100% B) afforded the title compound as a solid. Yield; 191 mg, 0.694 mmol, 43%. LCMS m/z 276.3 (M+1). $^1$H NMR (400 MHz, CDCl$_3$) δ 8.49 (br s, 1H), 7.56 (br d, J=7.6 Hz, 1H), 7.44-7.50 (m, 1H), 7.04 (br dd, J=7.6, 7.6 Hz, 1H), 6.92 (br d, J=8.4 Hz, 1H), 4.90-4.97 (m, 1H), 3.75-3.90 (m, 3H), 2.99-3.15 (m, 2H), 2.46-2.56 (m, 1H), 2.21-2.31 (m, 1H), 1.90-2.02 (m, 1H), 1.77-1.89 (m, 1H).

Step 4. Synthesis of 7-(4-methyl-1H-imidazol-1-yl)-2-{trans-2-[2-(trifluoromethyl)phenoxy]cyclobutyl}-3,4-dihydro-2H-pyrido[1,2-a]pyrazine-1,6-dione, trifluoroacetate salt (1)

A mixture of P1 (35 mg, 0.13 mmol), C9 (39 mg, 0.14 mmol), O-(7-azabenzotriazol-1-yl)-N,N,N',N'-tetramethyluronium hexafluorophosphate (HATU, 149 mg, 0.392 mmol) and N,N-diisopropylethylamine (0.89 mL, 0.51 mmol) in dichloromethane (2.3 mL) was stirred for 20 hours. Water (5 mL) was added, and the mixture was extracted with dichloromethane (3×5 mL). The combined organic layers were dried over magnesium sulfate, filtered, and concentrated in vacuo. Purification was carried out using reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 10% to 100% B). Yield: 50 mg, 0.11 mmol, 85%. LCMS m/z 459.1 (M+1). Retention time: 2.53 minutes (Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; Flow rate: 2 mL/minute).

Example 2

7-(4-Methyl-1H-imidazol-1-yl)-2-{trans-2-[2-(trifluoromethyl)phenoxy]cyclopentyl}-3,4-dihydro-2H-pyrido[1,2-a]pyrazine-1,6-dione (2)

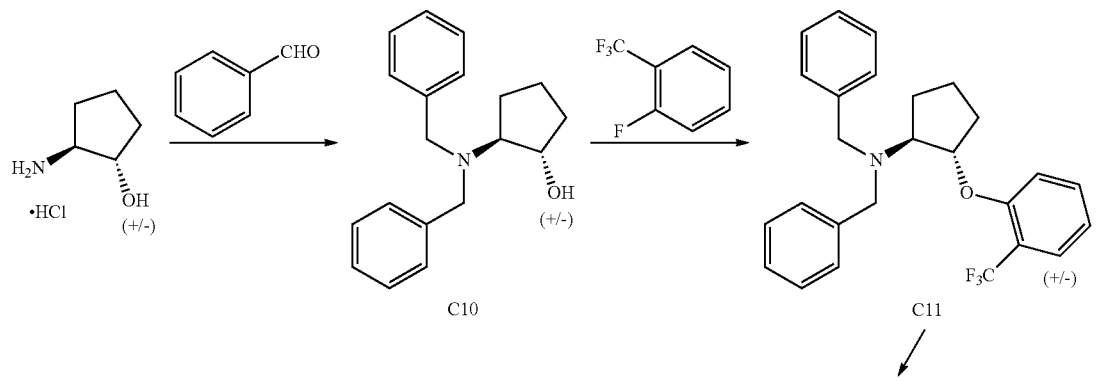

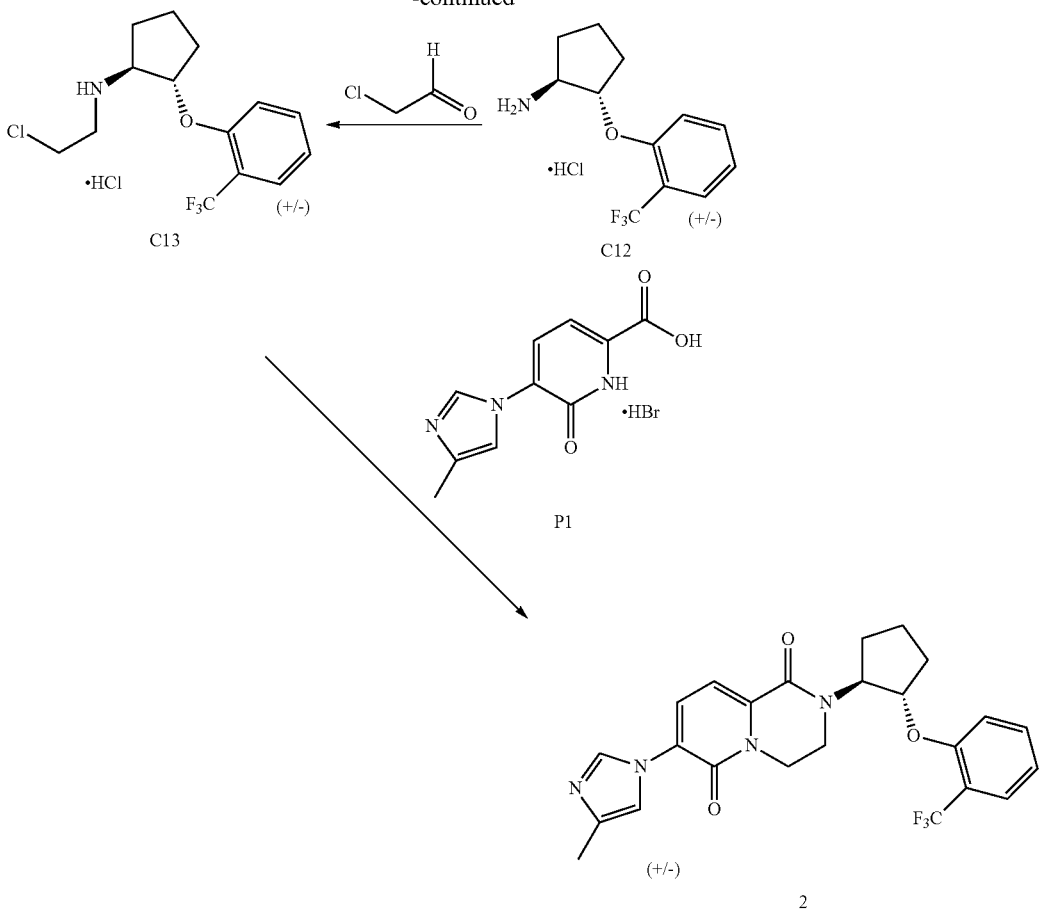

Step 1. Synthesis of trans-2-(dibenzylamino)cyclopentanol (C10)

To a solution of trans-2-aminocyclopentanol hydrochloride (385 mg, 2.82 mmol) in 1,2-dichloroethane was added benzaldehyde (748 mg, 7.04 mmol) and triethylamine (0.51 mL, 3.7 mmol). The mixture was heated to reflux for 2 hours, cooled to room temperature, and sodium triacetoxyborohydride was added. The reaction mixture was heated at reflux for an additional 18 hours, cooled to room temperature, then taken up in dichloromethane. The organic layer was washed with saturated aqueous sodium bicarbonate solution and with water, then dried over magnesium sulfate, filtered, and concentrated in vacuo. Purification via silica gel chromatography (Gradient: 25% to 50% ethyl acetate in heptane) afforded the title compound as a golden oil. Yield: 734 mg, 2.61 mmol, 93%. LCMS m/z 282.2 (M+1). $^1$H NMR (400 MHz, CDCl$_3$) δ 7.35-7.39 (m, 4H), 7.32 (br dd, J=7.8, 7.2 Hz, 4H), 7.21-7.26 (m, 2H), 4.05-4.12 (m, 1H), 3.79 (d, J=13.9 Hz, 2H), 3.52 (d, J=13.9 Hz, 2H), 2.90-2.99 (m, 1H), 1.74-1.95 (m, 2H), 1.52-1.71 (m, 3H), 1.39-1.49 (m, 1H).

Step 2. Synthesis of trans-N,N-dibenzyl-2-[2-(trifluoromethyl)phenoxy]cyclopentanamine (C11)

To a solution of C10 (820 mg, 2.91 mmol) in tetrahydrofuran (20 mL) in a high pressure tube was added sodium hydride (60% in oil, 175 mg, 4.37 mmol). After 15 minutes, 1-fluoro-2-(trifluoromethyl)benzene (1.43 g, 8.74 mmol) was introduced, the tube was sealed, and the mixture was heated to 70° C. for 18 hours, whereupon it was cooled to room temperature. The mixture was taken up in ethyl acetate, then washed with water and with saturated aqueous sodium chloride solution; the organic layer was dried over magnesium sulfate, filtered and concentrated in vacuo. Purification via silica gel chromatography (Gradient: 20% to 40% ethyl acetate in heptane) afforded the title compound as a golden oil. Yield: 212 mg, 0.498 mmol, 17%. LCMS m/z 426.2 (M+1). $^1$H NMR (400 MHz, CDCl$_3$) δ 7.55 (d, J=7.8 Hz, 1H), 7.41 (dd, J=8.0, 7.8 Hz, 1H), 7.34-7.39 (m, 4H), 7.24-7.30 (m, 4H), 7.17-7.23 (m, 2H), 7.03 (d, J=8.4 Hz, 1H), 6.95 (dd, J=7.6, 7.6 Hz, 1H), 4.76-4.82 (m, 1H), 3.68 (AB quartet, J$_{AB}$=14.0 Hz, Δv$_{AB}$=41.1 Hz, 4H), 3.50-3.57 (m, 1H), 1.85-2.00 (m, 2H), 1.62-1.84 (m, 4H).

Step 3. Synthesis of trans-2-[2-(trifluoromethyl)phenoxy]cyclopentanamine, hydrochloride salt (C12)

A solution of C11 (212 mg, 0.498 mmol), hydrogen chloride (4 N in 1,4-dioxane, 2 mL) and 10% Pd/C (100 mg) in methanol (5 mL) was hydrogenated at 50 psi in a Parr shaker at 50° C. After 3 hours, the reaction was filtered through Celite and concentrated in vacuo to afford the title compound as a dark residue. Yield: 156 mg, quantitative. LCMS m/z 246.2 (M+1).

Step 4. Synthesis of trans-N-(2-chloroethyl)-2-[2-(trifluoromethyl)phenoxy]cyclopentanamine, hydrochloride salt (C13)

To a solution of C12 (130 mg, 0.463 mmol), triethylamine (0.097 mL, 0.695 mmol), and sodium triacetoxyborohydride (238 mg, 1.06 mmol) in methanol (5 mL) was added chloroacetaldehyde (55% solution in water, 0.071 mL, 0.60 mmol). After 3 hours, the reaction mixture was concentrated in vacuo. The residue was taken up in dichloromethane and washed with saturated aqueous sodium bicarbonate solution and with water. The organic layer was dried over magnesium sulfate and filtered. To the filtrate was added hydrogen chloride (2 N in diethyl ether, 2 mL) and the mixture was concentrated in vacuo to afford the title compound as a light brown solid. This material was taken on to the next step without further purification. Yield: 111 mg, 0.323 mmol, 70%. LCMS m/z 308.1 (M+1).

Step 5. Synthesis of 7-(4-methyl-1H-imidazol-1-yl)-2-{trans-2-[2-(trifluoromethyl)phenoxy]cyclopentyl}-3,4-dihydro-2H-pyrido[1,2-a]pyrazine-1,6-dione (2)

To a solution of P1 (80 mg, 0.27 mmol) and C13 (110 mg, 0.32 mmol) in dichloromethane (5 mL) was added N,N-diisopropylethylamine (0.19 mL, 1.07 mmol) and O-(7-azabenzotriazol-1-yl)-N,N,N',N'-tetramethyluronium hexafluorophosphate (HATU, 97%, 124 mg, 0.32 mmol). The reaction was stirred for 5 days, then taken up in additional dichloromethane and washed with saturated aqueous sodium bicarbonate solution and with water. The organic layer was dried over magnesium sulfate, filtered and concentrated in vacuo. Purification by reversed phase HPLC (Column: Waters XBridge C18, 5 μm; Mobile phase A: 0.03% ammonium hydroxide in water (v/v); Mobile phase B: 0.03% ammonium hydroxide in acetonitrile (v/v); Gradient: 30% to 70% B) afforded the title compound as an oil. Yield: 3.6 mg, 7.6 μmol, 3%. LCMS m/z 473.3 (M+1). Retention time: 2.62 minutes (Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; Flow rate: 2 mL/minute).

Example 3

2-{trans-2-[(6,7-Difluoronaphthalen-1-yl)oxy]cyclobutyl}-7-(4-methyl-1H-imidazol-1-yl)-3,4-dihydro-2H-pyrido[1,2-a]pyrazine-1,6-dione (3)

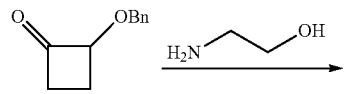

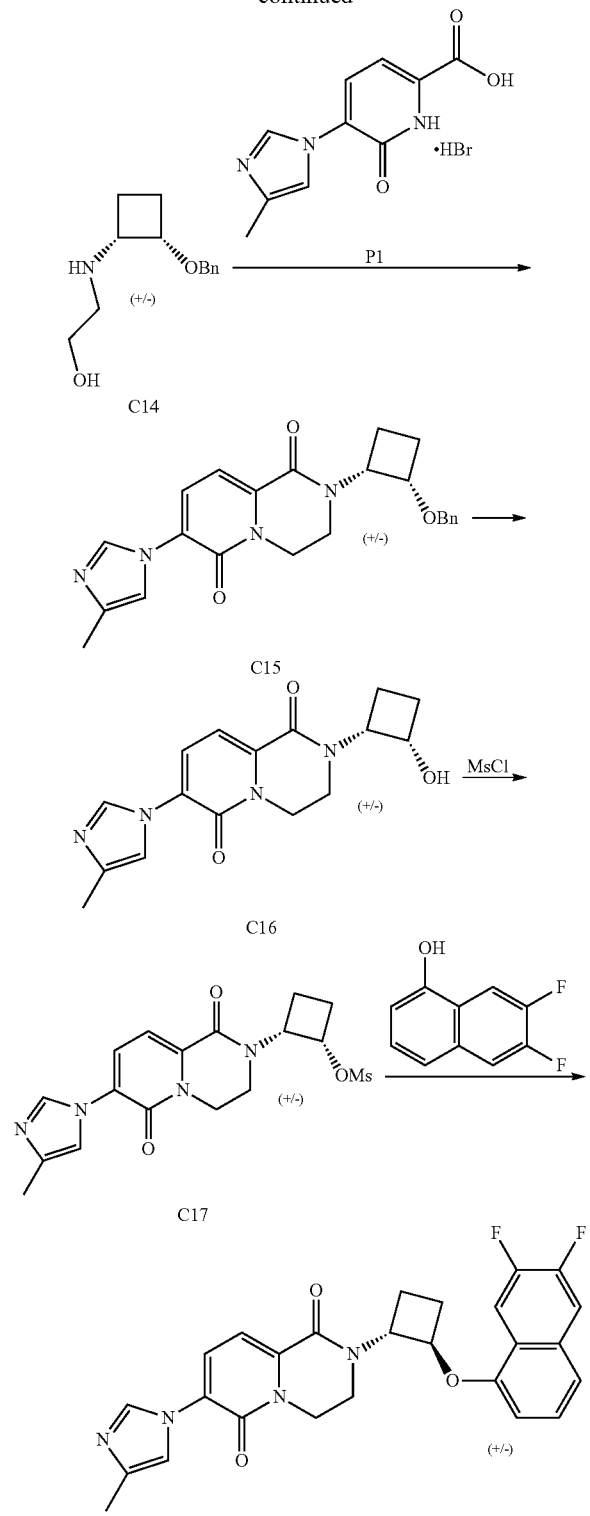

Step 1. Synthesis of 2-{[cis-2-(benzyloxy)cyclobutyl]amino}ethanol (C14)

A solution of 2-(benzyloxy)cyclobutanone (prepared according to the method of P. Bisel et al., *Eur. J. Org. Chem.*

1998, 4, 729-733; 2.35 g, 13.3 mmol) and 2-aminoethanol (1.63 g, 26.7 mmol) in dichloromethane (47 mL) was treated with acetic acid (0.76 mL, 13.3 mmol) and sodium triacetoxyborohydride (5.95 g, 26.7 mmol) and stirred at room temperature for 16 hours. Aqueous sodium hydroxide solution (1 N, 100 mL) was added and the mixture was extracted with dichloromethane (2×100 mL). The combined organic layers were washed with aqueous sodium hydroxide solution (1 N, 100 mL), dried over magnesium sulfate and concentrated in vacuo to afford the product as a colorless oil. Yield: 2.9 g, 13 mmol, 98%. $^1$H NMR (400 MHz, CDCl$_3$) δ 7.28-7.39 (m, 5H), 4.51 (AB quartet, $J_{AB}$=11.7 Hz, $\Delta v_{AB}$=61.1 Hz, 2H), 4.13-4.18 (m, 1H), 3.54-3.58 (m, 2H), 3.32-3.39 (m, 1H), 2.72-2.78 (m, 2H), 2.5 (v br s, 2H), 2.05-2.14 (m, 1H), 1.83-1.98 (m, 3H).

Step 2: Synthesis of 2-[cis-2-(benzyloxy)cyclobutyl]-7-(4-methyl-1H-imidazol-1-yl)-3,4-dihydro-2H-pyrido[1,2-a]pyrazine-1,6-dione (C15)

Compound P1 (2.40 g, 8.00 mmol) and C14 (2.00 g, 9.04 mmol) were combined in dichloromethane (160 mL) and treated with N,N-diisopropylethylamine (6.06 mL, 34.8 mmol) and O-(7-azabenzotriazol-1-yl)-N,N,N',N'-tetramethyluronium hexafluorophosphate (HATU, 97%, 7.84 g, 20.0 mmol). The reaction was stirred at room temperature for 55 hours. Water (200 mL) was added, and the mixture was extracted with dichloromethane (3×150 mL). The combined organic layers were dried over magnesium sulfate and concentrated in vacuo. Purification via silica gel chromatography (Gradient: 50% to 100% [10% 2 N ammonia in methanol/90% ethyl acetate] in ethyl acetate) afforded the title compound as a light yellow solid. Yield: 2.95 g, 7.29 mmol, 91%. $^1$H NMR (400 MHz, CDCl$_3$), characteristic peaks: δ 8.35 (d, J=1.4 Hz, 1H), 7.52 (d, J=7.8 Hz, 1H), 7.23-7.35 (m, 6H), 7.18-7.20 (m, 1H), 5.22-5.29 (m, 1H), 4.45 (AB quartet, $J_{AB}$=11.7 Hz, $\Delta v_{AB}$=52.2 Hz, 2H), 4.06-4.18 (m, 2H), 3.68-3.79 (m, 2H), 2.46-2.58 (m, 1H), 2.31 (d, J=0.8 Hz, 3H).

Step 3: Synthesis of 2-[cis-2-hydroxycyclobutyl]-7-(4-methyl-1H-imidazol-1-yl)-3,4-dihydro-2H-pyrido[1,2-a]pyrazine-1,6-dione (C16)

Compound C15 (2.50 g, 6.18 mmol) was mixed with dichloromethane (110 mL), treated with methanesulfonic acid (27 mL) and stirred at room temperature for 1.5 hours. Aqueous sodium hydroxide (6 N) was added until the pH reached 12 and then the mixture was extracted with dichloromethane (3×150 mL, then 5×50 mL). The combined organic layers were dried over magnesium sulfate and concentrated in vacuo. Silica gel chromatography (Gradient: 50% to 100% [20% 2 N ammonia in methanol/80% ethyl acetate] in ethyl acetate) provided the title compound as a white solid. Yield: 1.40 g, 4.45 mmol, 72%. $^1$H NMR (400 MHz, CDCl$_3$) δ 8.24 (d, J=1.2 Hz, 1H), 7.36 (d, J=7.6 Hz, 1H), 7.15 (d, J=7.8 Hz, 1H), 7.03-7.05 (m, 1H), 4.70-4.78 (m, 2H), 4.26-4.40 (m, 2H), 3.99 (ddd, J=13.4, 6.9, 4.3 Hz, 1H), 3.68 (ddd, J=13.3, 7.8, 4.3 Hz, 1H), 2.54-2.65 (m, 1H), 2.26 (d, J=0.8 Hz, 3H), 2.20-2.34 (m, 2H), 1.89-1.99 (m, 1H).

Step 4: Synthesis of cis-2-[7-(4-methyl-1H-imidazol-1-yl)-1,6-dioxo-1,3,4,6-tetrahydro-2H-pyrido[1,2-a]pyrazin-2-yl]cyclobutyl methanesulfonate (C17)

Methanesulfonyl chloride (148 μL, 1.91 mmol) was added drop-wise to a 0° C. solution of C16 (150 mg, 0.47 mmol) and triethylamine (530 μL, 3.82 mmol) in dichloromethane (15 mL), and the mixture was stirred for 20 minutes. Water (50 mL) was added, and the mixture was extracted with dichloromethane (3×50 mL). The combined organic layers were washed with saturated aqueous sodium chloride solution, dried over magnesium sulfate and concentrated in vacuo to afford the title compound as a light yellow solid. Yield: 175 mg, 0.45 mmol, 94%. LCMS m/z 393.4 (M+1). $^1$H NMR (400 MHz, CDCl$_3$) δ 8.24 (d, J=1.2 Hz, 1H), 7.44 (d, J=7.8 Hz, 1H), 7.24 (d, J=7.6 Hz, 1H), 7.13-7.15 (m, 1H), 5.30-5.35 (m, 1H), 5.13-5.20 (m, 1H), 4.47 (ddd, half of ABXY pattern, J=14.3, 7.6, 4.1 Hz, 1H), 4.37 (ddd, half of ABXY pattern, J=14.4, 7.4, 4.0 Hz, 1H), 3.96 (ddd, J=13.3, 7.4, 4.1 Hz, 1H), 3.74 (ddd, J=13.2, 7.6, 4.0 Hz, 1H), 2.99 (s, 3H), 2.66-2.77 (m, 1H), 2.29 (d, J=1.0 Hz, 3H), 2.24-2.50 (m, 3H).

Step 5: Synthesis of 2-{trans-2-[(6,7-difluoronaphthalen-1-yl)oxy]cyclobutyl}-7-(4-methyl-1H-imidazol-1-yl)-3,4-dihydro-2H-pyrido[1,2-a]pyrazine-1,6-dione (3)

A mixture of C17 (20 mg, 51 μmol), 6,7-difluoronaphthalen-1-ol (9.2 mg, 51 μmol), and potassium carbonate (35.6 mg, 255 μmol) in dimethyl sulfoxide (1.0 mL) was heated to 100° C. for 3 hours, filtered, and purified by reversed phase HPLC (Column: Waters XBridge C18, 5 μm; Mobile phase A: 0.03% ammonium hydroxide in water (v/v); Mobile phase B: 0.03% ammonium hydroxide in acetonitrile (v/v); Gradient: 20% to 70% B). LCMS m/z 477.0 (M+1). Retention time: 2.58 minutes (Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; Flow rate: 2 mL/minute).

Example 4

2-({3-[4-Chloro-3-(trifluoromethyl)phenyl]-4,5-dihydro-1,2-oxazol-5-yl}methyl)-7-(4-methyl-1H-imidazol-1-yl)-3,4-dihydro-2H-pyrido[1,2-a]pyrazine-1,6-dione (4)

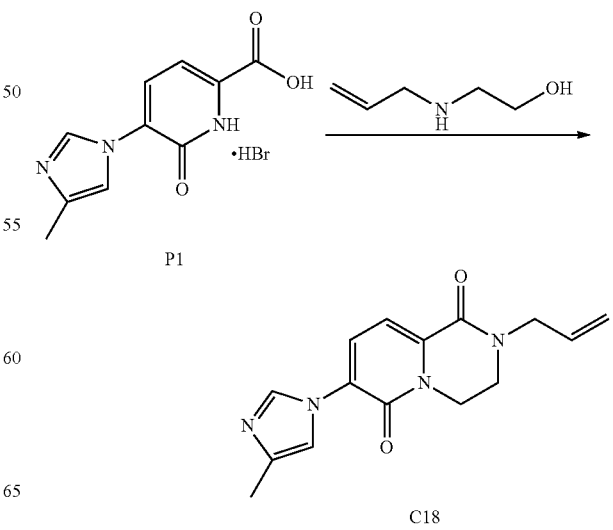

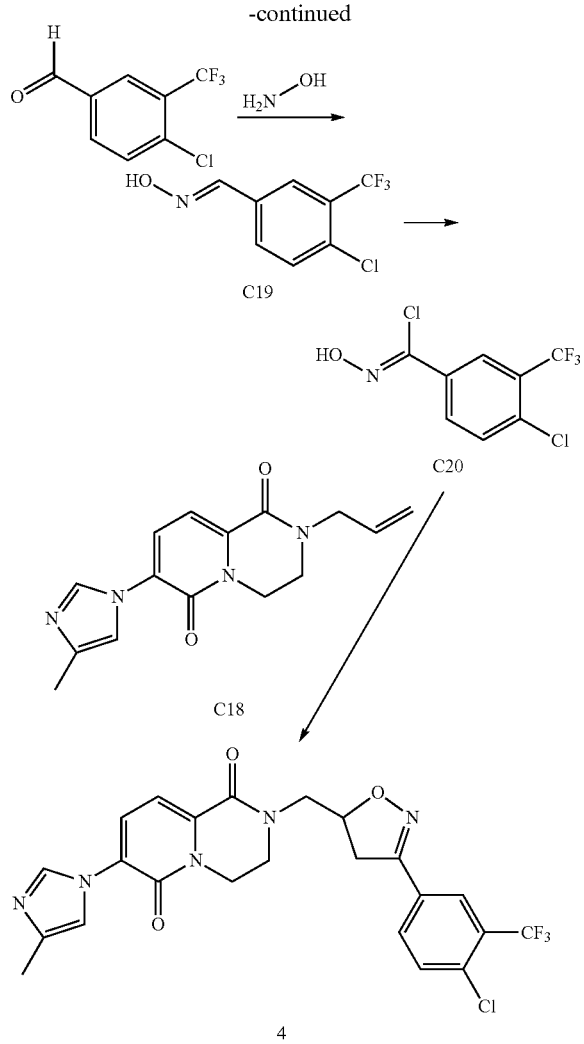

5.83 (ddt, J=16.8, 10.5, 6.1 Hz, 1H), 5.28-5.35 (m, 2H), 4.34-4.38 (m, 2H), 4.21 (ddd, J=6.0, 1.4, 1.2 Hz, 2H), 3.63-3.67 (m, 2H), 2.30 (d, J=1.0 Hz, 3H).

Step 2: Synthesis of (E)-1-[4-chloro-3-(trifluoromethyl)phenyl]-N-hydroxymethanimine (C19)

To a solution of 4-chloro-3-(trifluoromethyl)benzaldehyde (93.9 mg, 0.45 mmol) in tetrahydrofuran (0.9 mL) and ethanol (0.9 mL) was added hydroxylamine (50% in water, 0.20 mL) and the reaction was maintained at room temperature for 36 hours. Methanol (3.0 mL) was added, the solvent was removed in vacuo, and the residue was triturated with toluene (2×1 mL) to afford the title compound as a solid. Yield: 101 mg, 0.45 mmol, 100%.

Step 3: Synthesis of 4-chloro-N-hydroxy-3-(trifluoromethyl)benzenecarboximidoyl chloride (C20)

To a solution of C19 (101 mg, 0.45 mmol) in N,N-dimethylformamide (1.05 mL) was added N-chlorosuccinimide (0.45 M in N,N-dimethylformamide, 1.05 mL, 0.47 mmol). The reaction mixture was heated to 60° C. for 3 hours, then cooled to room temperature and used directly in the following step.

Step 4: Synthesis of 2-({3-[4-chloro-3-(trifluoromethyl)phenyl]-4,5-dihydro-1,2-oxazol-5-yl}methyl)-7-(4-methyl-1H-imidazol-1-yl)-3,4-dihydro-2H-pyrido[1,2-a]pyrazine-1,6-dione (4)

A solution of C18 (0.4 M in dichloromethane, 0.375 mL, 0.15 mmol) was added to the crude reaction mixture from the previous step, followed by addition of N-methylmorpholine (1.0 M in N,N-dimethylformamide, 0.60 mL, 0.60 mmol), and the reaction mixture was left at room temperature for 66 hours. After removal of solvents in vacuo, the residue was dissolved in 1,2-dichloroethane (5.0 mL) and treated with 50% saturated aqueous sodium bicarbonate solution (4.0 mL). The aqueous layer was extracted with 1,2-dichloroethane (4.0 mL), and the combined organic layers were concentrated in vacuo. Purification via reversed phase high pressure liquid chromatography (HPLC) (Column: Phenomenex Gemini C18, 5 μm; Mobile phase A: 0.1% ammonium hydroxide in water (v/v); Mobile phase B: 0.1% ammonium hydroxide in methanol (v/v); Gradient: 5% to 100% B) yielded material assigned as the indicated 3,5-disubstituted dihydro-1,2-oxazole isomer on the basis of 2-dimensional NMR experiments. This was concentrated from ethyl acetate three times to provide the title compound as a yellow solid. Yield: 5.7 mg, 0.011 mmol, 7%. LCMS m/z 505.9 (M+1). $^1$H NMR (400 MHz, CDCl$_3$) δ 8.24 (d, J=1.2 Hz, 1H), 7.87 (d, J=2.2 Hz, 1H), 7.54-7.64 (m, 2H), 7.45 (d, J=7.8 Hz, 1H), 7.26 (d, J=8 Hz, 1H, assumed; partially obscured by solvent peak), 7.13-7.16 (m, 1H), 5.11-5.20 (m, 1H), 4.45 (ddd, J=14.3, 7.0, 4.1 Hz, 1H), 4.31 (ddd, J=14.3, 7.6, 4.3 Hz, 1H), 3.87-4.04 (m, 3H), 3.74 (dd, J=14.4, 6.7 Hz, 1H), 3.63 (dd, half of ABX pattern, J=17.5, 10.7 Hz, 1H), 3.47 (dd, half of ABX pattern, J=17.6, 7.2 Hz, 1H), 2.28 (br s, 3H).

Step 1: Synthesis of 7-(4-methyl-1H-imidazol-1-yl)-2-(prop-2-en-1-yl)-3,4-dihydro-2H-pyrido[1,2-a]pyrazine-1,6-dione (C18)

Compound P1 (2.02 g, 6.73 mmol) and 2-(prop-2-en-1-ylamino)ethanol (prepared according to the method of M. Matteucci et al., U.S. Pat. Appl. Publ. 2007, US 20070060534 A1 20070315) (681 mg, 6.73 mmol) were combined in dichloromethane (40 mL) and N,N-diisopropylethylamine (5.86 mL, 33.7 mmol) and the mixture was stirred until it became homogenous. O-(7-Azabenzotriazol-1-yl)-N,N,N',N'-tetramethyluronium hexafluorophosphate (HATU, 97%, 7.92 g, 20.2 mmol) was added and the reaction was stirred at room temperature for 48 hours. Aqueous sodium hydroxide solution (1 N) was added and the mixture was extracted three times with 20% isopropanol in chloroform. The combined organic layers were dried over sodium sulfate and concentrated in vacuo. Purification was carried out using silica gel chromatography (Gradient: 0% to 20% [2 M NH$_3$ in methanol] in dichloromethane) followed by trituration with ethyl acetate. Yield: 718 mg, 2.52 mmol, 38%. A second crop was obtained from the filtrate via a second trituration. Yield: 221 mg, 0.77 mmol, 11%. $^1$H NMR (400 MHz, CDCl$_3$) δ 8.28 (d, J=1.2 Hz, 1H), 7.47 (d, J=7.8 Hz, 1H), 7.29 (d, J=7.6 Hz, 1H), 7.13-7.15 (m, 1H),

Example 5

2-{cis-2-[4-Fluoro-2-(trifluoromethyl)phenoxy]cyclopentyl}-7-(4-methyl-1H-imidazol-1-yl)-3,4-dihydro-2H-pyrido[1,2-a]pyrazine-1,6-dione (5)

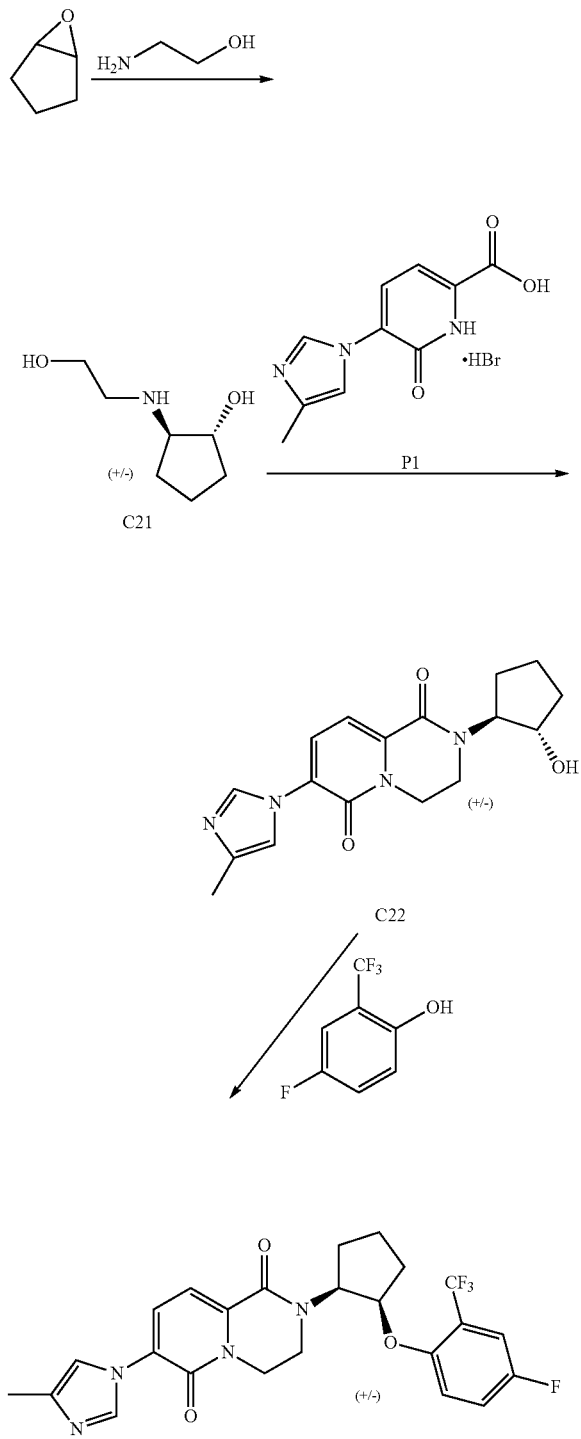

Step 1. Synthesis of trans-2[(2-hydroxyethyl)amino]cyclopentanol (C21)

A mixture of 6-oxabicyclo[3.1.0]hexane (3.00 g, 35.7 mmol) and 2-aminoethanol (2.18 g, 35.7 mmol) in ethanol (15 mL) was stirred at 80° C. in a sealed tube for 16 hours. The reaction mixture was cooled to room temperature and concentrated in vacuo. Purification using silica gel chromatography (Eluant: methanol in dichloromethane) afforded the title compound. Yield: 1.6 g, 11 mmol, 31%. $^1$H NMR (400 MHz, DMSO-$d_6$) δ 4.43-4.64 (br m, 2H), 3.68-3.75 (m, 1H), 3.44 (t, J=5.6 Hz, 2H), 2.71-2.77 (m, 1H), 2.58-2.63 (m, 2H), 1.73-1.89 (m, 2H), 1.47-1.64 (m, 2H), 1.34-1.44 (m, 1H), 1.17-1.28 (m, 1H).

Step 2. Synthesis of 2-[trans-2-hydroxycyclopentyl]-7-(4-methyl-1H-imidazol-1-yl)-3,4-dihydro-2H-pyrido[1,2-a]pyrazine-1,6-dione (C22)

The reaction of C21 with P1 was carried out according to the general procedure for the synthesis of 1 in Example 1. When the reaction was complete as assessed by thin layer chromatography, the reaction mixture was diluted with water. The aqueous layer was extracted three times with 5% methanol in dichloromethane, and the combined organic layers were dried over sodium sulfate and concentrated in vacuo. Silica gel chromatography (Eluant: methanol in dichloromethane) and trituration with ethyl acetate afforded the title compound as an off-white solid. Yield: 340 mg, 1.04 mmol, 22%. LCMS m/z 329.0 (M+1). $^1$H NMR (300 MHz, DMSO-$d_6$) δ 8.27 (s, 1H), 7.80 (d, J=7.3 Hz, 1H), 7.42 (s, 1H), 7.08 (d, J=7.3 Hz, 1H), 4.85-4.98 (br m, 1H), 4.44-4.60 (m, 1H), 4.03-4.36 (m, 3H), 3.59-3.68 (m, 2H), 2.15 (s, 3H), 1.42-1.96 (m, 6H).

Step 3. Synthesis of 2-{cis-2-[4-fluoro-2-(trifluoromethyl)phenoxy]cyclopentyl}-7-(4-methyl-1H-imidazol-1-yl)-3,4-dihydro-2H-pyrido[1,2-a]pyrazine-1,6-dione (5)

Triphenylphosphine (12.2 mg, 0.046 mmol) was added to a solution of C22 (11 mg, 0.033 mmol) and 4-fluoro-2-(trifluoromethyl)phenol (7.4 mg, 0.041 mmol) in tetrahydrofuran (0.5 mL). The reaction mixture was treated with a solution of diisopropyl azodicarboxylate (94%, 0.015 mL, 0.071 mmol) in tetrahydrofuran, and heated at 50° C. for 18 hours, then at 90° C. for 4 hours. The same quantities of triphenylphosphine and diisopropyl azodicarboxylate were again added, and heating was continued at 90° C. for an additional 4 days. The mixture was concentrated in vacuo. Purification by reversed phase HPLC (Column: Waters XBridge C18, 5 μm; Mobile phase A: 0.03% ammonium hydroxide in water (v/v); Mobile phase B: 0.03% ammonium hydroxide in acetonitrile (v/v); Gradient: 40% to 100% B) afforded the title compound. Yield: 2.8 mg, 5.7 μmol, 17%. LCMS m/z 491.1 (M+1). Retention time: 2.32 minutes (Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; Flow rate: 2 mL/minute).

Example 6
7-(4-Methyl-1H-imidazol-1-yl)-2-({(2S,3S,5R)-3-methyl-5-[4-(trifluoromethyl)phenyl]tetrahydrofuran-2-yl}methyl)-3,4-dihydro-2H-pyrido[1,2-a]pyrazine-1,6-dione (6)
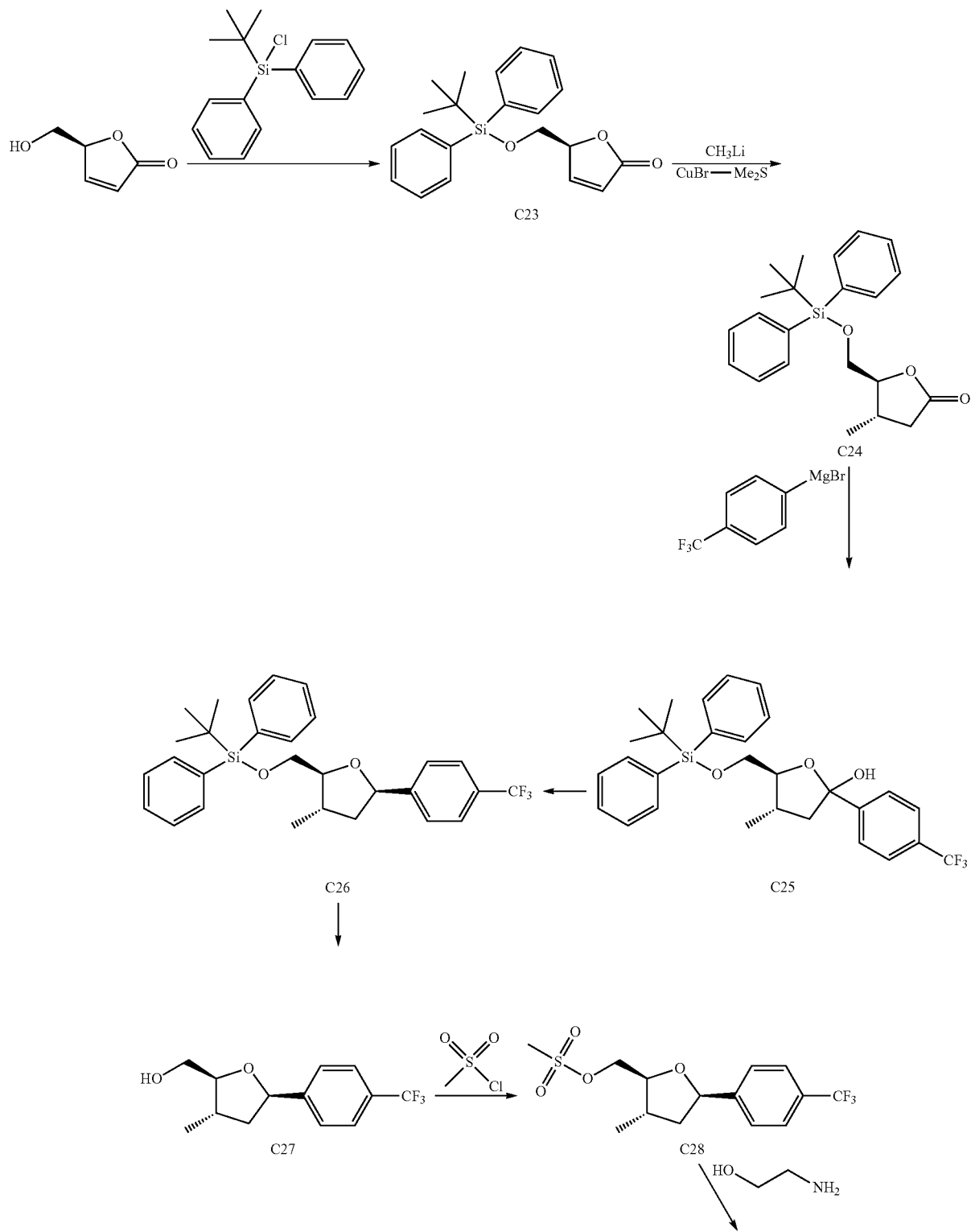

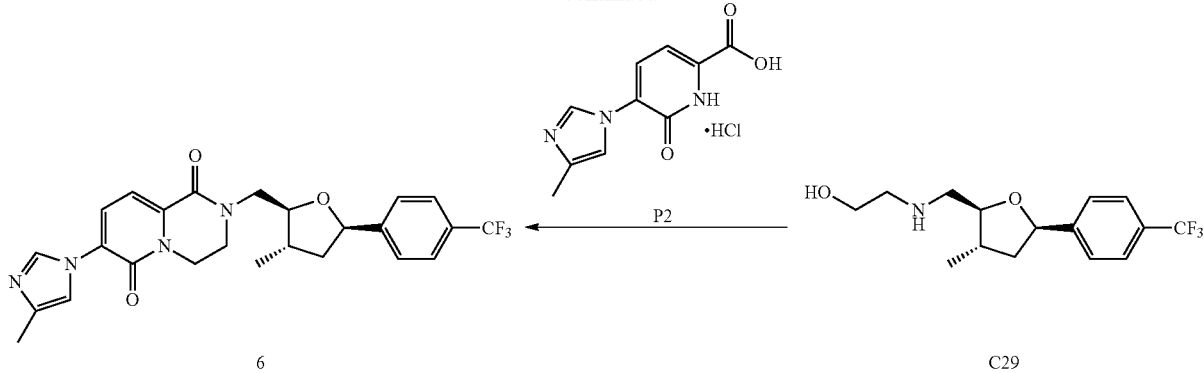

Step 1. Synthesis of (5S)-5-({[tert-butyl(diphenyl)silyl]oxy}methyl)furan-2(5H)-one (C23)

Imidazole (1.22 g, 17.6 mmol) and tert-butyl(diphenyl)silyl chloride (3.95 mL, 15.4 mmol) were added to a solution of (5S)-5-(hydroxymethyl)furan-2(5H)-one (1.60 g, 14.0 mmol) in N,N-dimethylformamide (50 mL), and the reaction mixture was stirred at room temperature for 18 hours. It was then partitioned between tert-butyl methyl ether and water; the organic layer was washed twice with water, dried over magnesium sulfate, filtered, and concentrated in vacuo. Silica gel chromatography (Gradient: 5% to 30% ethyl acetate in heptane) afforded the product as a white solid. Yield: 5.20 g, quantitative. $^1$H NMR (400 MHz, CDCl$_3$) δ 7.63-7.66 (m, 4H), 7.38-7.49 (m, 7H), 6.19 (dd, J=5.7, 2.0 Hz, 1H), 5.06-5.10 (m, 1H), 3.93 (dd, half of ABX pattern, J=10.9, 4.5 Hz, 1H), 3.88 (dd, half of ABX pattern, J=10.8, 5.0 Hz, 1H), 1.05 (s, 9H).

Step 2. Synthesis of (4S,5S)-5-({[tert-butyl(diphenyl)silyl]oxy}methyl)-4-methyldihydrofuran-2(3H)-one (C24)

Copper(I) bromide-dimethyl sulfide complex (99%, 3.65 g, 17.6 mmol) was suspended in diethyl ether (25 mL) and cooled to 0° C. After drop-wise addition of methyllithium (1.6 M solution in diethyl ether, 22.0 mL, 35.2 mmol), the reaction mixture was cooled to −25° C. A solution of C23 (3.10 g, 8.79 mmol) in diethyl ether (20 mL) was added at a rate such that the reaction temperature remained below −20° C. After 30 minutes, the reaction was quenched with saturated aqueous ammonium chloride solution (50 mL) and warmed to room temperature. The mixture was extracted with diethyl ether, and the combined organic layers were dried over magnesium sulfate, filtered, and concentrated under reduced pressure to afford the product as a thick oil, which was used in the following step without additional purification. Yield: 3.20 g, 8.68 mmol, 99%. $^1$H NMR (400 MHz, CDCl$_3$) δ 7.65-7.69 (m, 4H), 7.38-7.48 (m, 6H), 4.09-4.13 (m, 1H), 3.87 (dd, half of ABX pattern, J=11.5, 3.3 Hz, 1H), 3.73 (dd, half of ABX pattern, J=11.5, 3.5 Hz, 1H), 2.83 (dd, J=17.6, 8.8 Hz, 1H), 2.53-2.64 (m, 1H), 2.18 (dd, J=17.4, 7.0 Hz, 1H), 1.14 (d, J=7.0 Hz, 3H), 1.06 (s, 9H).

Step 3. Synthesis of (4S,5S)-5-({[tert-butyl(diphenyl)silyl]oxy}methyl)-4-methyl-2-[4-(trifluoromethyl)phenyl]tetrahydrofuran-2-ol (C25)

Finely ground cerium chloride (95%, 6.98 g, 26.9 mmol) was heated at 135° C. under high vacuum for 2 hours, and then cooled to room temperature. To this material was added a solution of C24 (3.20 g, 8.68 mmol) in tetrahydrofuran (40 mL); the resulting mixture was stirred for 1 hour and then cooled to an internal temperature of −45° C. [4-(Trifluoromethyl)phenyl]magnesium bromide (0.48 M solution in tetrahydrofuran, 54.3 mL, 26.1 mmol) was added at a rate that maintained the reaction temperature below −40° C., and stirring was continued for 1 hour. The reaction was quenched with saturated aqueous ammonium chloride solution (30 mL) and filtered through Celite. The filtrate was extracted with tert-butyl methyl ether, and the combined organic layers were washed with saturated aqueous sodium chloride solution, dried over sodium sulfate, filtered and concentrated in vacuo. The product, obtained as an oil, was used without additional purification. Yield: 4.4 g, 8.6 mmol, 99%.

Step 4. Synthesis of tert-butyl({(2S,3S,5R)-3-methyl-5-[4-(trifluoromethyl)phenyl]tetrahydrofuran-2-yl}methoxy)diphenylsilane (C26)

Compound C25 (4.4 g, 8.6 mmol) was dissolved in dichloromethane (50 mL) and cooled to −78° C. Triethylsilane (98%, 6.97 mL, 42.8 mmol) was added, followed by drop-wise addition of boron trifluoride diethyl etherate (98%, 5.50 mL, 42.7 mmol). After 1 hour at −78° C., the reaction was quenched with saturated aqueous sodium bicarbonate solution, warmed to room temperature, and extracted with tert-butyl methyl ether. The combined organic layers were dried over magnesium sulfate, filtered, combined with the product of an identical reaction carried out on 2.5 g (4.9 mmol) of C25, and concentrated in vacuo. Two chromatographic purifications on silica gel [1) Gradient: 0% to 2.5% ethyl acetate in heptane; 2) Eluent: 1% ethyl acetate in heptane] afforded the product (the second-eluting isomer from the column) as an oil. Yield: 1.19 g, 2.39 mmol, 18%. The indicated relative stereochemistry was assigned on the basis of $^1$H NMR studies carried out on the product of the following step. Products of related reactions (vide infra) were assigned corresponding stereochemistry. $^1$H NMR (400 MHz, CDCl$_3$) δ 7.70-7.75 (m, 4H), 7.51 (s, 4H), 7.36-7.48 (m, 6H), 5.10 (dd, J=7.0, 6.8 Hz, 1H), 3.91 (dd, half of ABX pattern, J=10.9, 4.1 Hz, 1H), 3.80 (dd, half of ABX pattern, J=10.9, 4.3 Hz, 1H), 3.72 (ddd, J=7.1, 4.1, 4.0 Hz, 1H), 2.29-2.41 (m, 1H), 1.97-2.09 (m, 2H), 1.09 (s, 9H), 1.07 (d, J=6.8 Hz, 3H).

Step 5. Synthesis of {(2S,3S,5R)-3-methyl-5-[4-(trifluoromethyl)phenyl]tetrahydrofuran-2-yl}methanol (C27)

Tetrabutylammonium fluoride (1.0 M solution in tetrahydrofuran, 2.62 mL, 2.62 mmol) was added to a solution of C26 (1.19 g, 2.39 mmol) in tetrahydrofuran (15 mL). After 1 hour at room temperature, tert-butyl methyl ether was added, and the mixture was washed with water, dried over sodium sulfate, filtered, and concentrated in vacuo. Chromatography on silica gel (Gradient: 10% to 50% ethyl acetate in heptane) provided the product as a colorless oil. Yield: 530 mg, 2.04 mmol, 85%. The indicated relative stereochemistry was supported by NOE studies on C27 and its aryl stereoisomer, which was obtained in the same way from the first-eluting isomer of the previous step. $^1$H NMR (400 MHz, CDCl$_3$) δ 7.60 (br d, J=8.0 Hz, 2H), 7.44-7.49 (m, 2H), 5.09 (dd, J=7.2, 7.0 Hz, 1H), 3.84-3.91 (m, 1H), 3.67-3.75 (m, 2H), 2.16-2.27 (m, 1H), 2.05-2.10 (m, 2H), 1.90 (br s, 1H), 1.13 (d, J=6.8 Hz, 3H).

Step 6. Synthesis of {(2S,3S,5R)-3-methyl-5-[4-(trifluoromethyl)phenyl]tetrahydrofuran-2-yl}methyl methanesulfonate (C28)

The product, obtained as an oil, was prepared from C27 according to the general procedure for the synthesis of C8 in Example 1. Yield: 689 mg, 2.04 mmol, 100%. $^1$H NMR (400 MHz, CDCl$_3$) δ 7.61 (br d, J=8.1 Hz, 2H), 7.45-7.49 (m, 2H), 5.13 (br dd, J=7.1, 6.9 Hz, 1H), 4.43 (dd, half of ABX pattern, J=11.0, 3.4 Hz, 1H), 4.37 (dd, half of ABX pattern, J=11.0, 5.6 Hz, 1H), 3.90 (ddd, J=7.2, 5.6, 3.3 Hz, 1H), 3.07 (s, 3H), 2.18-2.30 (m, 1H), 2.07-2.12 (m, 2H), 1.17 (d, J=6.8 Hz, 3H).

Step 7. Synthesis of 2-[({(2S,3S,5R)-3-methyl-5-[4-(trifluoromethyl)phenyl]tetrahydrofuran-2-yl}methyl)amino]ethanol (C29)

Compound C28 (689 mg, 2.04 mmol) was combined with 2-aminoethanol (96%, 2 mL, 30 mmol) and heated to 85° C. for 2 hours. After cooling to room temperature, the reaction mixture was partitioned between tert-butyl methyl ether and water (10 mL). The organic layer was dried over sodium sulfate, filtered, and concentrated in vacuo to provide the product as a thick oil. Yield: 618 mg, 2.04 mmol, 100%. LCMS m/z 304.2 [M+H$^+$]. $^1$H NMR (400 MHz, CDCl$_3$) δ 7.59 (br d, J=8 Hz, 2H), 7.42-7.47 (m, 2H), 5.05 (br dd, J=6.8, 6.6 Hz, 1H), 3.69-3.75 (m, 1H), 3.67 (t, J=5.3 Hz, 2H), 2.79-2.94 (m, 4H), 2.01-2.12 (m, 3H), 1.11 (d, J=6.2 Hz, 3H).

Step 8. Synthesis of 7-(4-methyl-1H-imidazol-1-yl)-2-({(2S,3S,5R)-3-methyl-5-[4-(trifluoromethyl)phenyl]tetrahydrofuran-2-yl}methyl)-3,4-dihydro-2H-pyrido[1,2-a]pyrazine-1,6-dione (6)

To a solution of P2 (514 mg, 2.01 mmol) and C29 (610 mg, 2.01 mmol) in dichloromethane (20 mL) was added N,N-diisopropylethylamine (1.23 mL, 7.06 mmol) and O-(7-azabenzotriazol-1-yl)-N,N,N',N'-tetramethyluronium hexafluorophosphate (HATU, 99%, 1.78 g, 4.63 mmol). The reaction mixture was heated at reflux for 2 hours, then diluted with additional dichloromethane and washed with saturated aqueous sodium bicarbonate solution, with water, and with saturated aqueous sodium chloride solution. The organic layer was dried over sodium sulfate, filtered and concentrated in vacuo. The residue was purified via silica gel chromatography (Gradient: 0% to 5% [~0.7 M ammonia in methanol] in ethyl acetate). The off-white foam obtained from the column was treated with ethyl acetate; after standing, a precipitate formed. This was isolated by filtration and washed with small amounts of ethyl acetate and tert-butyl methyl ether to afford the product as a white solid. Yield: 243 mg, 0.499 mmol, 25%. LCMS m/z 487.3 [M+H$^+$]. $^1$H NMR (400 MHz, CDCl$_3$) δ 8.33 (d, J=1.3 Hz, 1H), 7.62 (br d, J=8.1 Hz, 2H), 7.49 (d, J=7.7 Hz, 1H), 7.43 (br d, J=8 Hz, 2H), 7.29 (d, J=7.7 Hz, 1H), 7.15-7.17 (m, 1H), 5.04 (br dd, J=7, 7 Hz, 1H), 4.40 (ddd, half of ABXY pattern, J=14.2, 7.2, 4.2 Hz, 1H), 4.30 (ddd, half of ABXY pattern, J=14.2, 7.7, 4.2 Hz, 1H), 4.22 (dd, J=14.0, 2.5 Hz, 1H), 3.99 (ddd, J=13.5, 7.9, 4.2 Hz, 1H), 3.79-3.87 (m, 2H), 3.46 (dd, J=14.0, 8.0 Hz, 1H), 2.32 (d, J=1.0 Hz, 3H), 2.06-2.11 (m, 3H), 1.19-1.22 (m, 3H).

Example 7

2-({(2S,4R,5S)-4-Fluoro-5-[4-(trifluoromethyl)phenyl]tetrahydrofuran-2-yl}methyl)-7-(4-methyl-1H-imidazol-1-yl)-3,4-dihydro-2H-pyrido[1,2-a]pyrazine-1,6-dione (7)

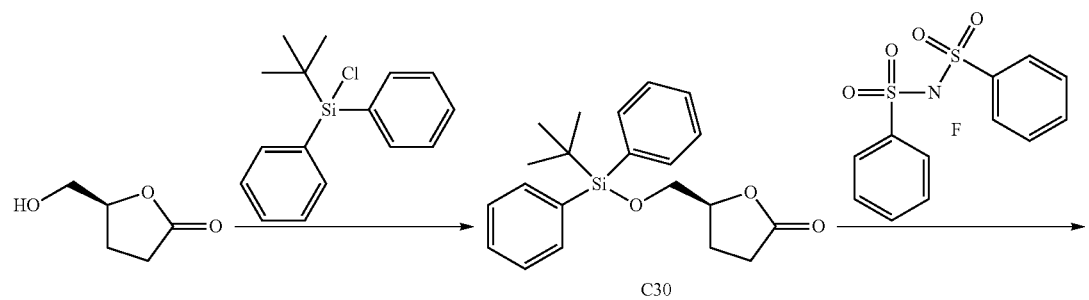

C30

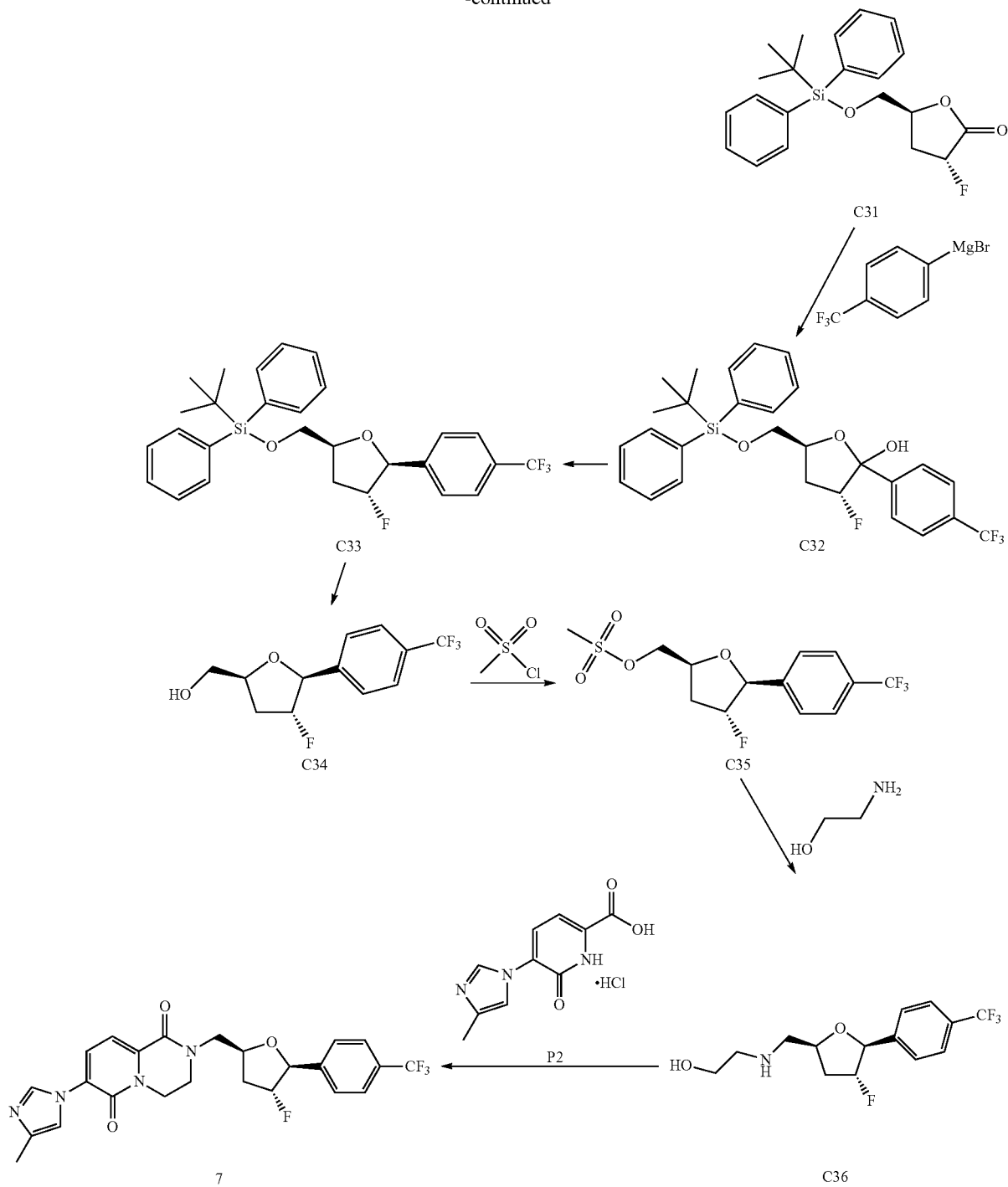

Step 1. Synthesis of (5S)-5-({[tert-butyl(diphenyl)silyl]oxy}methyl)dihydrofuran-2(3H)-one (C30)

(5S)-5-(Hydroxymethyl)dihydrofuran-2(3H)-one was converted to the product according to the general procedure for the synthesis of C23 in Example 6. In this case, the crude product was recrystallized from hexanes, and the product was obtained as a white solid. Yield: 10.6 g, 29.9 mmol, 56%. $^1$H NMR (400 MHz, CDCl$_3$) δ 7.65-7.69 (m, 4H), 7.38-7.48 (m, 6H), 4.58-4.64 (m, 1H), 3.89 (dd, half of ABX pattern, J=11.3, 3.3 Hz, 1H), 3.70 (dd, half of ABX pattern, J=11.3, 3.3 Hz, 1H), 2.69 (ddd, half of ABXY pattern, J=17.7, 10.2, 7.1 Hz, 1H), 2.52 (ddd, half of ABXY pattern, J=17.8, 10.0, 6.6 Hz, 1H), 2.18-2.35 (m, 2H), 1.07 (s, 9H).

Step 2. Synthesis of (3R,5S)-5-({[tert-butyl(diphenyl)silyl]oxy}methyl)-3-fluorodihydrofuran-2(3H)-one (C31)

A solution of C30 (5.00 g, 14.1 mmol) and N-fluoro-N-(phenylsulfonyl)benzenesulfonamide (4.45 g, 14.1 mmol) in tetrahydrofuran (50 mL) was cooled to −78° C. Lithium bis(trimethylsilyl)amide (1.0 M solution in tetrahydrofuran, 14.1 mL, 14.1 mmol) was added drop-wise over 15 minutes, and the reaction mixture was stirred at −78° C. for 2 hours. The reaction was quenched with saturated aqueous ammonium chloride solution (15 mL), warmed to room temperature, and partitioned between tert-butyl methyl ether and saturated aqueous sodium bicarbonate solution. The organic layer was washed with saturated aqueous sodium bicarbonate solution and with saturated aqueous sodium chloride solution, then dried over magnesium sulfate, filtered, and concentrated in vacuo. After purification via silica gel chromatography (Gradient: 5% to 30% ethyl acetate in heptane), recrystallization from hexanes afforded the product as a white solid. Yield: 1.64 g, 4.40 mmol, 31%. $^1$H NMR (400 MHz, CDCl$_3$) δ 7.61-7.66 (m, 4H), 7.39-7.50 (m, 6H), 5.50 (ddd, J=52.7, 8.6, 7.6 Hz, 1H), 4.69-4.74 (m, 1H), 3.93 (ddd, J=11.6, 2.2, 2.2 Hz, 1H), 3.62 (dd, J=11.5, 2.0 Hz, 1H), 2.71 (dddd, J=13.6, 9.4, 8.6, 2.4 Hz, 1H), 2.55 (dddd, J=27.7, 13.6, 8.8, 7.7 Hz, 1H), 1.06 (s, 9H).

Step 3. Synthesis of (3R,5S)-5-({[tert-butyl(diphenyl)silyl]oxy}methyl)-3-fluoro-2-[4-(trifluoromethyl)phenyl]tetrahydrofuran-2-ol (C32)

Compound C31 was converted to the product according to the general procedure for the synthesis of C25 in Example 6. The product was obtained as an oil, which was taken directly to the following step. Yield: 2.20 g, 4.24 mmol, 99%.

Step 4. Synthesis of tert-butyl({(2S,4R,5S)-4-fluoro-5-[4-(trifluoromethyl)phenyl]tetrahydrofuran-2-yl}methoxy)diphenylsilane (C33)

The product was prepared from C32 using the general procedure for synthesis of C26 in Example 6. In this case, purification was carried out using silica gel chromatography (Gradient: 0% to 5% ethyl acetate in heptane). Yield: 890 mg, 1.77 mmol, 42%. The indicated relative stereochemistry was consistent with NOE studies carried out on the product. $^1$H NMR (400 MHz, CDCl$_3$) δ 7.69-7.74 (m, 4H), 7.58-7.62 (m, 2H), 7.53 (br d, half of br AB quartet, J=8 Hz, 2H), 7.37-7.49 (m, 6H), 5.22 (br d, J=26.6 Hz, 1H), 4.93-5.11 (m, 1H), 4.43-4.50 (m, 1H), 4.10 (dd, J=11.4, 3.2 Hz, 1H), 3.84 (dd, J=11.3, 3.5 Hz, 1H), 2.08-2.32 (m, 2H), 1.11 (s, 9H).

Step 5. Synthesis of {(2S,4R,5S)-4-fluoro-5-[4-(trifluoromethyl)phenyl]tetrahydrofuran-2-yl}methanol (C34)

The product, obtained as a thick oil that slowly solidified, was prepared from C33 according to the general procedure for the synthesis of C27 in Example 6. Yield: 392 mg, 1.48 mmol, 84%. The indicated relative stereochemistry was consistent with NOE studies carried out on this sample. $^1$H NMR (400 MHz, CDCl$_3$) δ 7.64 (br d, J=8 Hz, 2H), 7.52 (br d, J=8 Hz, 2H), 5.19 (br d, J=26.8 Hz, 1H), 5.04 (dddd, J=55.0, 5.1, 1.8, 1.6 Hz, 1H), 4.44-4.51 (m, 1H), 4.03 (dd, J=12.0, 2.8 Hz, 1H), 3.77 (dd, J=12.0, 4.8 Hz, 1H), 2.00-2.25 (m, 2H), 1.81 (br s, 1H).

Step 6. Synthesis of {(2S,4R,5S)-4-fluoro-5-[4-(trifluoromethyl)phenyl]tetrahydrofuran-2-yl}methyl methanesulfonate (C35)

The product, obtained as a thick oil that slowly solidified, was prepared from C34 using the general procedure for the synthesis of C8 in Example 1. Yield: 505 mg, 1.48 mmol, 100%. $^1$H NMR (400 MHz, CDCl$_3$) δ 7.65 (br d, J=8 Hz, 2H), 7.52 (br d, J=8 Hz, 2H), 5.25 (br d, J=26.6 Hz, 1H), 4.98-5.15 (m, 1H), 4.60-4.67 (m, 1H), 4.57 (dd, half of ABX pattern, J=11.3, 2.9 Hz, 1H), 4.45 (dd, half of ABX pattern, J=11.3, 4.9 Hz, 1H), 3.10 (s, 3H), 2.30 (dddd, J=19.9, 14.1, 5.2, 1.2 Hz, 1H), 2.04 (dddd, J=36.8, 14.1, 10.7, 5.0 Hz, 1H).

Step 7. Synthesis of 2-[({(2S,4R,5S)-4-fluoro-5-[4-(trifluoromethyl)phenyl]tetrahydrofuran-2-yl}methyl)amino]ethanol (C36)

The product, obtained as an oil, was prepared from C35 using the general procedure for the synthesis of C29 in Example 6. Yield: 454 mg, 1.48 mmol, 100%. LCMS m/z 308.1 [M+H$^+$]. $^1$H NMR (400 MHz, CDCl$_3$) δ 7.63 (br d, J=8 Hz, 2H), 7.49 (br d, J=8 Hz, 2H), 5.16 (br d, J=27.3 Hz, 1H), 4.93-5.10 (m, 1H), 4.44-4.52 (m, 1H), 3.69 (dd, J=5.7, 4.9 Hz, 2H), 3.01 (dd, half of ABX pattern, J=12.5, 3.5 Hz, 1H), 2.84-2.96 (m, 3H), 2.24 (dddd, J=21.1, 14.1, 5.0, 1.2 Hz, 1H), 1.90 (dddd, J=37.1, 14.0, 10.8, 5.3 Hz, 1H).

Step 8. Synthesis of 2-({(2S,4R,5S)-4-fluoro-5-[4-(trifluoromethyl)phenyl]tetrahydrofuran-2-yl}methyl)-7-(4-methyl-1H-imidazol-1-yl)-3,4-dihydro-2H-pyrido[1,2-a]pyrazine-1,6-dione (7)

Compound C36 was converted to the product according to the general method described for synthesis of 6 in Example 6. The product was obtained as a solid. Yield: 50 mg, 0.10 mmol, 7%. LCMS m/z 491.3 [M+H$^+$]. $^1$H NMR (400 MHz, CDCl$_3$) δ 8.39 (br s, 1H), 7.67 (br d, J=8 Hz, 2H), 7.51 (d, J=7.8 Hz, 1H), 7.48 (br d, J=8 Hz, 2H), 7.31 (d, J=7.6 Hz, 1H), 7.16-7.18 (m, 1H), 5.17 (br d, J=27.3 Hz, 1H), 5.04 (br dd, J=55, 5 Hz, 1H), 4.57-4.65 (m, 1H), 4.32-4.47 (m, 2H), 4.30 (dd, J=14.2, 2.7 Hz, 1H), 4.02 (ddd, J=13.5, 7.6, 4.1 Hz, 1H), 3.85 (ddd, J=13.5, 7.2, 4.1 Hz, 1H), 3.53 (dd, J=14.1, 8.2 Hz, 1H), 2.33 (d, J=1.0 Hz, 3H), 2.32-2.43 (m, 1H), 1.77-1.95 (m, 1H).

Example 8
7-(4-Methyl-1H-imidazol-1-yl)-2-[(1S)-1-{(2S,5R)-5-[4-(trifluoromethyl)phenyl]tetrahydrofuran-2-yl}ethyl]-3,4-dihydro-2H-pyrido[1,2-a]pyrazine-1,6-dione (8)
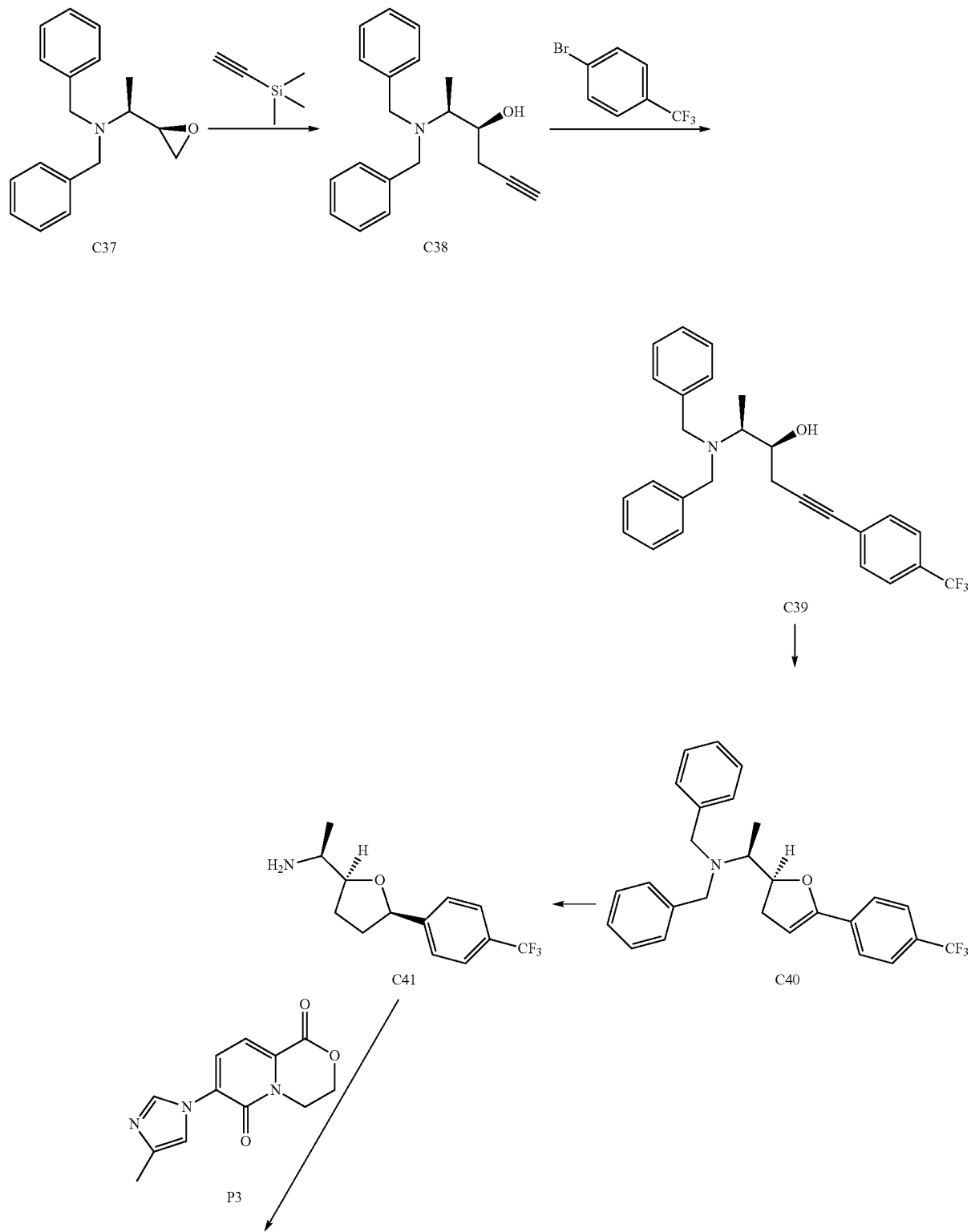

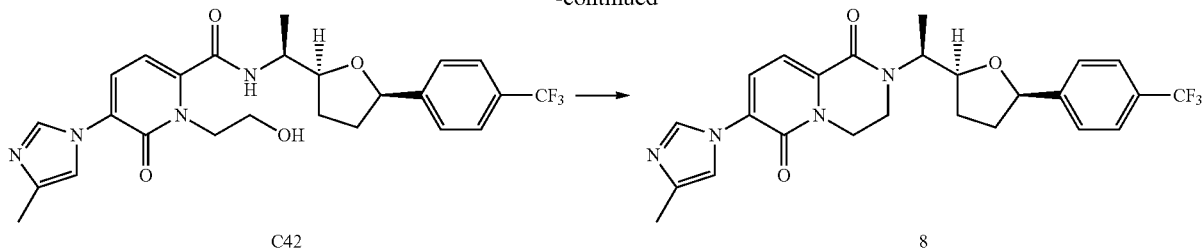

C42 → 8

Step 1. Synthesis of (2S,3S)-2-(dibenzylamino)hex-5-yn-3-ol (C38)

n-Butyllithium (2.5 M solution in hexanes, 131 mL, 328 mmol) was added drop-wise over approximately 9 minutes to a −70° C. solution of ethynyl(trimethyl)silane (46.3 mL, 328 mmol) in tetrahydrofuran (1 L), and the reaction mixture was stirred at −70° C. for 30 minutes. A solution of (1S)—N,N-dibenzyl-1-[(2R)-oxiran-2-yl]ethanamine (C37, see J. Barluenga et al., *J. Org. Chem.* 1995, 60, 6696-6699) (79.6 g, 298 mmol) in tetrahydrofuran (250 mL) was added; the reaction mixture, which had warmed as a result of the addition, was recooled to approximately −65° C., and boron trifluoride diethyl etherate (37.6 mL, 298 mmol) was added. The reaction mixture was then stirred for 1.5 hours at −70° C. Saturated aqueous ammonium chloride solution (200 mL) was added, and the mixture was allowed to warm to room temperature. The organic layer was washed with saturated aqueous sodium chloride solution, and the aqueous layer from the quenched reaction was extracted with ethyl acetate. The combined organic layers were dried over magnesium sulfate, filtered, and concentrated in vacuo. The residue was dissolved in methanol (500 mL), treated with potassium carbonate (206 g, 1.49 mol) and stirred at room temperature for 18 hours. After filtration through Celite and rinsing with ethyl acetate, the crude product solution was concentrated in vacuo, dissolved in diethyl ether (1 L), washed with water (250 mL) and with saturated aqueous sodium chloride solution (75 mL), dried over magnesium sulfate, filtered and concentrated under reduced pressure. After seeding with a small sample of solid product, heptane (60 mL) was added, and the mixture was vigorously stirred for 5 minutes, then filtered; the isolated solid was rinsed with heptane (50 mL) to afford the product as a pale orange solid. Yield: 37.3 g, 127 mmol, 43%. $^1$H NMR (400 MHz, CDCl$_3$) δ 7.22-7.36 (m, 10H), 4.53 (s, 1H), 3.84 (d, J=13.1 Hz, 2H), 3.63 (ddd, J=9.5, 5.8, 4.0 Hz, 1H), 3.34 (d, J=13.3 Hz, 2H), 2.80 (dq, J=9.4, 6.6 Hz, 1H), 2.46 (ddd, half of ABXY pattern, J=17.0, 4.0, 2.6 Hz, 1H), 2.21 (ddd, half of ABXY pattern, J=17.0, 6.0, 2.6 Hz, 1H), 1.86 (dd, J=2.7, 2.5 Hz, 1H), 1.07 (d, J=6.8 Hz, 3H).

Step 2. Synthesis of (2S,3S)-2-(dibenzylamino)-6-[4-(trifluoromethyl)phenyl]hex-5-yn-3-ol (C39)

Compound C38 (25.6 g, 87.2 mmol) was added to a mixture of 1-bromo-4-(trifluoromethyl)benzene (12.2 mL, 87.1 mmol), tetrakis(triphenylphosphine)palladium(0) (5.04 g, 4.36 mmol) and copper(I) iodide (997 mg, 5.24 mmol) in triethylamine (previously degassed with nitrogen via a dispersion tube for 20 minutes, 250 mL) and the reaction mixture was stirred at 75° C. for 1.75 hours. After cooling to room temperature, the reaction mixture was filtered through Celite and the filter pad was rinsed with diethyl ether (300 mL). The filtrate was poured into saturated aqueous ammonium chloride solution (250 mL); the aqueous layer was extracted with diethyl ether (250 mL), and the combined organic layers were washed with saturated aqueous sodium chloride solution, dried over magnesium sulfate, filtered, and concentrated in vacuo. Heptane (150 mL) was added to the residue, and the mixture was again concentrated under reduced pressure. This material was combined with the corresponding solids from a similar reaction carried out on C38 (25.0 g, 85.2 mmol) and purified via silica gel chromatography (Eluent: 25% ethyl acetate in heptane). The isolated solid (~60 g) was recrystallized from heptane (250 mL) to afford the product as a reddish-brown solid. Yield: 47.2 g, 108 mmol, 63%. $^1$H NMR (400 MHz, CDCl$_3$) δ 7.49 (br d, J=8 Hz, 2H), 7.20-7.33 (m, 12H), 4.55 (br s, 1H), 3.87 (d, J=13.1 Hz, 2H), 3.70-3.76 (m, 1H), 3.36 (d, J=13.3 Hz, 2H), 2.93 (dq, J=9.4, 6.7 Hz, 1H), 2.76 (dd, half of ABX pattern, J=17.4, 3.9 Hz, 1H), 2.48 (dd, half of ABX pattern, J=17.3, 5.0 Hz, 1H), 1.12 (d, J=6.7 Hz, 3H).

Step 3. Synthesis of (1S)—N,N-dibenzyl-1-{(2S)-5-[4-(trifluoromethyl)phenyl]-2,3-dihydrofuran-2-yl}ethanamine (C40)

Trifluoroacetic acid (18 mL, 230 mmol) and di-μ-chlorodichlorobis(ethylene)diplatinum(II) (97%, 3.76 g, 6.20 mmol) were added to a solution of C39 (49.4 g, 113 mmol) in dichloromethane (80 mL). After 1.5 hours at room temperature, the reaction mixture was poured into aqueous sodium hydroxide solution (0.5 M, 500 mL), and the aqueous layer was extracted with dichloromethane (250 mL). The combined organic layers were dried over sodium sulfate, filtered, and concentrated in vacuo. The residue was combined with crude product from a similar reaction run on C39 (10.0 g, 22.9 mmol) and rapidly purified on a short column by silica gel chromatography (Eluent: 2% ethyl acetate in heptane), providing the product as a light yellow-orange solid. Yield: 46.5 g, 106 mmol, 78%. $^1$H NMR (400 MHz, CDCl$_3$) δ 7.65 (br AB quartet, $J_{AB}$=8.2 Hz, $\Delta v_{AB}$=40.1 Hz, 4H), 7.40 (br d, J=8 Hz, 4H), 7.23-7.28 (m, 4H), 7.16-7.22 (m, 2H), 5.46 (dd, J=2.9, 2.7 Hz, 1H), 4.80 (ddd, J=9.8, 9.6, 7.2 Hz, 1H), 3.95 (d, J=13.8 Hz, 2H), 3.63 (d, J=13.8 Hz, 2H), 2.96-3.04 (m, 1H), 2.73 (br dd, J=9.8, 2.5 Hz, 2H), 1.18 (d, J=6.8 Hz, 3H).

Step 4. Synthesis of (1S)-1-{(2S,5R)-5-[4-(trifluoromethyl)phenyl]tetrahydrofuran-2-yl}ethanamine (C41)

Palladium hydroxide on carbon (~50% water, 10 wt % palladium, 7.1 g, 5 mmol) was added to a slurry of C40 (22.0 g, 50.3 mmol) and ammonium formate (80.2 g, 1.27 mol) in methanol (500 mL), and the reaction mixture was stirred for 2.5 hours at room temperature, then combined with similar reactions run on C41 (24.5 g, 56.0 mmol) and filtered through Celite, rinsing with methanol (1 L). The filtrate was concentrated in vacuo and treated with aqueous sodium hydroxide solution (0.2 M, roughly 800 mL), while keeping the pH at approximately 9. This was extracted three times with ethyl acetate (0.5 L, 1 L and 0.5 L), and the combined organic layers were washed with saturated aqueous sodium chloride solution, dried over magnesium sulfate, and concentrated under reduced pressure to afford the product as a light yellow oil. Hydrogenation was assumed to have occurred on the less hindered face; the assigned stereochemistry was also supported by the $IC_{50}$ obtained on the final product 8, which indicated that the tetrahydrofuran moiety bore the substituents in a cis orientation (see Table 1). Yield: 26.3 g, 101 mmol, 95%. $^1$H NMR (400 MHz, CDCl$_3$) δ 7.53 (br AB quartet, $J_{AB}$=8 Hz, $\Delta\nu_{AB}$=50 Hz, 4H), 4.96 (dd, J=7.4, 7.0 Hz, 1H), 3.70-3.77 (m, 1H), 2.93-3.01 (m, 1H), 2.33-2.43 (m, 1H), 2.00-2.10 (m, 1H), 1.66-1.85 (m, 2H), 1.12 (d, J=6.4 Hz, 3H).

Step 5. Synthesis of 1-(2-hydroxyethyl)-5-(4-methyl-1H-imidazol-1-yl)-6-oxo-N-[(1S)-1-{(2S,5R)-5-[4-(trifluoromethyl)phenyl]tetrahydrofuran-2-yl}ethyl]-1,6-dihydropyridine-2-carboxamide (C42)

Bis(trimethylaluminum)-1,4-diazabicyclo[2.2.2]octane adduct (97%, 27.8 g, 105 mmol) was added to a solution of C41 (21.0 g, 81.0 mmol) in tetrahydrofuran (800 mL), and the mixture was heated to 40° C. for 45 minutes. Compound P3 (28 g, 110 mmol) was added, and the reaction mixture was heated at reflux for 2 hours, then cooled in an ice bath to approximately 5° C. With vigorous stirring, aqueous hydrochloric acid (1 N, 75 mL) was slowly added drop-wise {Caution: gas evolution does not begin immediately!}, bringing the pH to 7-8. Aqueous sodium hydroxide solution (1 M, 75 mL) was added, and the mixture was filtered through Celite, rinsing with ethyl acetate (3×500 mL). The organic layer from the filtrate was washed with aqueous sodium hydroxide solution (1 M, 150 mL), with water (250 mL), and with saturated aqueous sodium chloride solution (100 mL), then dried over magnesium sulfate, filtered, and concentrated in vacuo. The resulting pasty solid was dried under vacuum at 50° C., then cooled, stirred with diethyl ether (300 mL) for 20 minutes, and filtered to provide the product as a cream-colored solid, still containing roughly 13% diethyl ether by weight, via $^1$H NMR analysis. Corrected yield: 31.0 g, 61.4 mmol, 76%. This material was used in the following step. $^1$H NMR (400 MHz, CDCl$_3$) δ 8.19 (br d, J=8.8 Hz, 1H), 7.99 (d, J=1.2 Hz, 1H), 7.58 (br AB quartet, $J_{AB}$=8.2 Hz, $\Delta\nu_{AB}$=28.5 Hz, 4H), 7.17 (d, J=7.6 Hz, 1H), 6.98-7.00 (m, 1H), 6.34 (d, J=7.6 Hz, 1H), 5.00 (dd, J=7.4, 6.6 Hz, 1H), 4.34-4.41 (m, 1H), 4.28-4.33 (m, 2H), 4.06-4.14 (m, 1H), 3.96-4.03 (m, 1H), 3.71-3.78 (m, 1H), 2.38-2.47 (m, 1H), 2.15-2.23 (m, 1H), 2.12 (d, J=1.0 Hz, 3H), 1.80-1.95 (m, 2H), 1.35 (d, J=6.6 Hz, 3H).

Step 6. Synthesis of 7-(4-methyl-1H-imidazol-1-yl)-2-[(1S)-1-{(2S,5R)-5-[4-(trifluoromethyl)phenyl]tetrahydrofuran-2-yl}ethyl]-3,4-dihydro-2H-pyrido[1,2-a]pyrazine-1,6-dione (8)

Compound C42 (from the previous step; corrected weight: 30.9 g, 61.2 mmol) and triethylamine (16 mL, 110 mmol) were combined in tetrahydrofuran (1 L) and cooled in an ice bath. Methanesulfonyl chloride (98%, 8.5 mL, 110 mmol) was added drop-wise over 3 to 5 minutes, whereupon the cooling bath was removed. The reaction mixture was stirred at room temperature for 40 minutes, then cooled again in an ice bath, treated with 1,3,4,6,7,8-hexahydro-2H-pyrimido[1,2-a]pyrimidine (97%, 30.2 g, 210 mmol), and stirred for 2.5 hours. Ethyl acetate (500 mL) was added to the cold reaction mixture, which was subsequently washed with water (2×500 mL). The aqueous layer was extracted with ethyl acetate (500 mL) and the combined organic layers were washed with saturated aqueous sodium chloride solution (250 mL), dried over magnesium sulfate, filtered, and concentrated in vacuo. Silica gel chromatography (Eluents: ethyl acetate, then 5% methanol in ethyl acetate) afforded fractions containing the product; these were concentrated to a volume of roughly 500 mL and the resulting slurry was stirred under nitrogen for 18 hours. After being cooled to 7° C., the slurry was filtered to provide a white solid (22 g). The filtrate was concentrated under reduced pressure, and the resulting solid was slurried with diethyl ether (70 mL) and isolated by filtration; this material was recrystallized from ethyl acetate (60 mL), cooled in ice, filtered, and rinsed with ice-cold ethyl acetate to afford a cream-colored solid (5.5 g). The two lots were combined and recrystallized from ethyl acetate (330 mL) to afford the product as a white solid. Yield: 24.3 g, 49.9 mmol, 82%. LCMS m/z 487.3 [M+H$^+$]. $^1$H NMR (400 MHz, CDCl$_3$) δ 8.25 (d, J=1.2 Hz, 1H), 7.58 (br d, J=8 Hz, 2H), 7.47 (d, J=7.6 Hz, 1H), 7.42 (br d, J=8 Hz, 2H), 7.30 (d, J=7.6 Hz, 1H), 7.12-7.14 (m, 1H), 4.92 (dd, J=7.4, 6.8 Hz, 1H), 4.82-4.90 (m, 1H), 4.26-4.39 (m, 2H), 4.09-4.16 (m, 1H), 3.79 (ddd, half of ABXY pattern, J=13.3, 7.3, 4.3 Hz, 1H), 3.67 (ddd, half of ABXY pattern, J=13.3, 7.2, 4.3 Hz, 1H), 2.37-2.45 (m, 1H), 2.30 (d, J=1.0 Hz, 3H), 2.15-2.24 (m, 1H), 1.77-1.91 (m, 2H), 1.33 (d, J=7.0 Hz, 3H).

Example 9

2-[(1S)-1-{(2S,5R)-5-[4-Chloro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione (9)

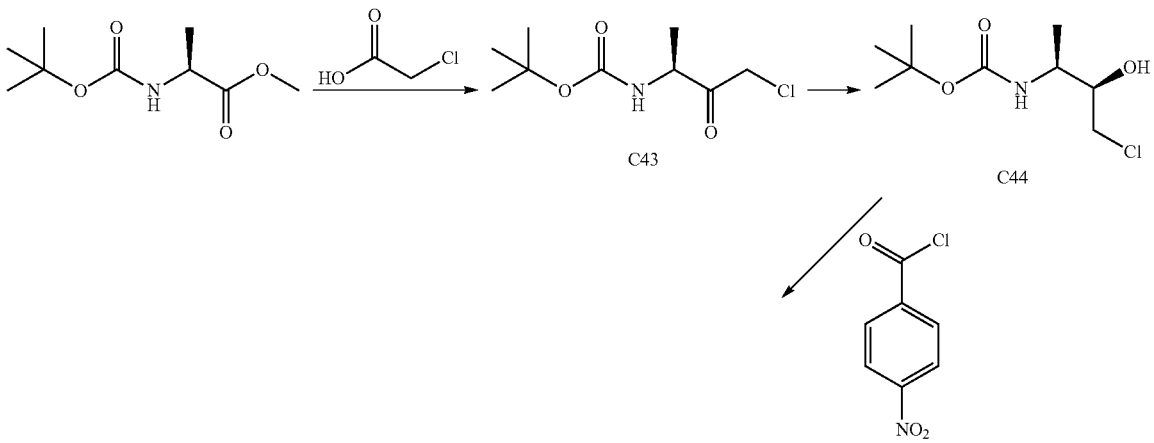

-continued
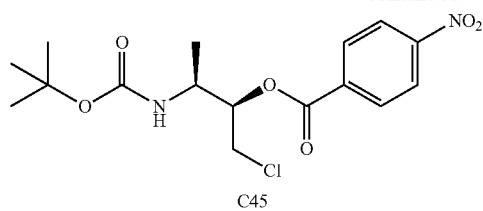
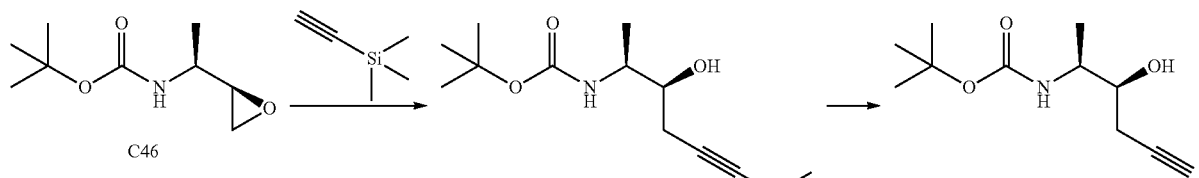
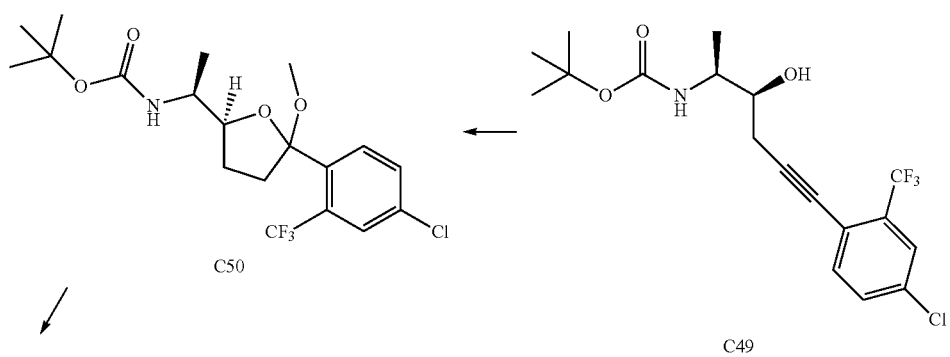
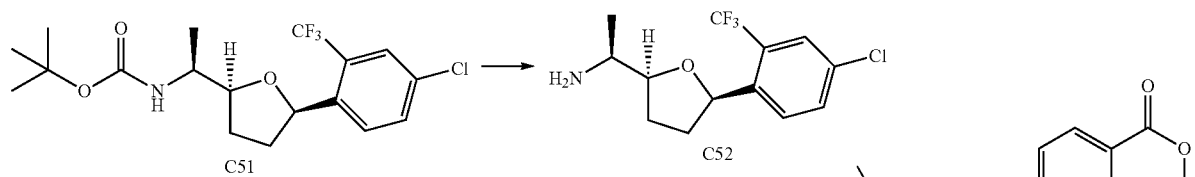

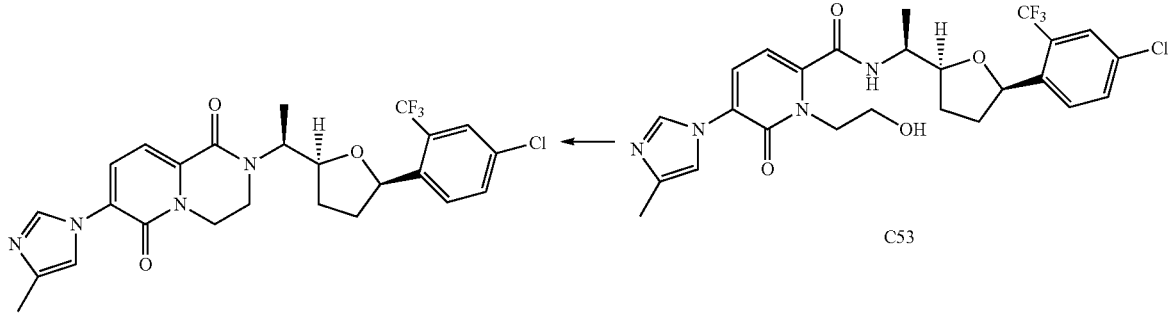

Step 1. Synthesis of tert-butyl [(2S)-4-chloro-3-oxobutan-2-yl]carbamate (C43)

A solution of chloroacetic acid (23.2 g, 246 mmol) in tetrahydrofuran (100 mL) was added over 35 minutes to a −78° C. solution of lithium diisopropylamide in tetrahydrofuran (2.05 M, 240 mL, 492 mmol), at a rate that kept the internal temperature below −65° C. After 30 minutes, the reaction mixture was quickly transferred into a (dry ice)-jacketed addition funnel and added over 5 minutes to a solution of methyl N-(tert-butoxycarbonyl)-L-alaninate (10.0 g, 49.2 mmol) in tetrahydrofuran (120 mL). Mechanical stirring was used for this reaction. The mixture was stirred for 30 minutes, during which time the reaction mixture warmed to 0° C. It was cooled to −78° C. and treated over 10 minutes with a solution of acetic acid (41 mL, 720 mmol) in tetrahydrofuran (41 mL). At this point, the flask was immersed in an ice bath, and stirring was continued for 1.5 hours, while the reaction warmed to 5° C. Water (250 mL) was added, followed by diethyl ether (400 mL); the organic layer was washed with saturated aqueous sodium bicarbonate solution (150 mL) and with saturated aqueous sodium chloride solution (50 mL), dried over magnesium sulfate, filtered, and concentrated in vacuo to afford the product as a waxy, light yellow solid. Yield: 9.47 g, 42.7 mmol, 87%. $^1$H NMR (400 MHz, CDCl$_3$) δ 5.11 (br d, J=6 Hz, 1H), 4.48-4.58 (m, 1H), 4.28 (AB quartet, $J_{AB}$=15.9 Hz, $\Delta v_{AB}$=8.3 Hz, 2H), 1.44 (s, 9H), 1.38 (d, J=7.1 Hz, 3H).

Step 2. Synthesis of tert-butyl [(2S,3R)-4-chloro-3-hydroxybutan-2-yl]carbamate (C44)

A solution of C43 (16.0 g, 72.2 mmol) in diethyl ether (100 mL) was added to a mixture of lithium tri-tert-butoxyaluminum hydride (97%, 28.4 g, 108 mmol) in diethyl ether (500 mL). After 3 hours at room temperature, the reaction mixture was cooled to 0° C., quenched with aqueous hydrochloric acid (1 M, 150 mL), and extracted with tert-butyl methyl ether. The combined organic layers were dried over sodium sulfate, filtered, and concentrated in vacuo to provide a thick oil, which was stirred with methylcyclohexane (45 mL). The resulting solid was isolated via filtration and washed with methylcyclohexane to provide the product (3.1 g). The filtrate was concentrated, mixed with pentane (25 mL), heated to reflux, cooled with stirring and seeded with solid product. The resulting material was filtered and rinsed with pentane to provide the product as a solid (8.1 g). Total yield: 11.2 g, 50.1 mmol, 69%. $^1$H NMR (400 MHz, CDCl$_3$) δ 4.76 (br s, 1H), 3.77-3.87 (m, 1H), 3.69-3.76 (m, 1H), 3.65 (dd, half of ABX pattern, J=11.3, 3.9 Hz, 1H), 3.53 (dd, half of ABX pattern, J=11.3, 8.0 Hz, 1H), 2.95 (br s, 1H), 1.45 (s, 9H), 1.27 (d, J=6.8 Hz, 3H).

Alternative Step 2. Synthesis of tert-butyl [(2S,3R)-4-chloro-3-hydroxybutan-2-yl]carbamate (C44)

A 0.1 M potassium phosphate buffer, 2.0 mM in magnesium chloride, was prepared by combining potassium dihydrogenphosphate (9.86 g, 72.4 mmol), potassium hydrogenphosphate (22.2 g, 127 mmol) and magnesium chloride hexahydrate (0.812 g, 4.0 mmol) in water (2 L); the pH of the resulting solution was 7.05. To this phosphate buffer (1.8 L) was added nicotinamide adenine dinucleotide phosphate, disodium salt trihydrate (1.9 g, 2.4 mmol) and ketoreductase enzyme (Codexis, KRED-P1-E05) (8 g), and the mixture was stirred for 45 minutes at 22° C. to dissolve the ketoreductase. A solution of tert-butyl [(2S)-4-chloro-3-oxobutan-2-yl]carbamate (C43) (50.0 g, 226 mmol) in 2-propanol (200 mL) was added, and the resulting suspension was stirred for 46 hours at 30° C., under a nitrogen flow (10 mL/minute) from a sparge inlet containing 2-propanol and water (1:1, 300 mL). At this point, tert-butyl methyl ether (1 L) was added to the reaction mixture, which was swirled for 20 minutes. The resulting emulsion was filtered through diatomaceous earth (200 g), and the filter cake was broken and washed with tert-butyl methyl ether (3×400 mL). The combined organic layers from the filtrates were dried with sodium sulfate (625 g), filtered, and concentrated in vacuo to afford the crude product as a red oil (50 g). This material was mixed with ethyl acetate (80 mL) and treated with decolorizing carbon (5 g) over 10 minutes with gentle heating. After filtration through Celite, the solution was concentrated in vacuo and mixed with warm hexanes (40 mL) under stirring. After 18 hours, the resulting solid was collected via filtration and rinsed with pentane, providing the product as a white powder (14.14 g). The mother liquor was concentrated under reduced pressure to yield an oil (32 g), which was crystallized in the same way using warm hexanes (30 mL) to obtain additional product as a white powder (13.65 g). Total yield: 27.79 g, 124 mmol, 55%. $^1$H NMR (400 MHz, CDCl$_3$) δ 4.77 (br s, 1H), 3.77-3.87 (m, 1H), 3.69-3.76 (m, 1H), 3.65 (dd, half of ABX pattern, J=11.1, 3.9 Hz, 1H), 3.53 (dd, half of ABX pattern, J=11.3, 8.0 Hz, 1H), 3.00 (br s, 1H), 1.45 (s, 9H), 1.26 (d, J=6.8 Hz, 3H).

Step 3. Synthesis of (2R,3S)-3-[(tert-butoxycarbonyl)amino]-1-chlorobutan-2-yl 4-nitrobenzoate (C45)

A solution of C44 (15 g, 67 mmol) in dichloromethane (400 mL) was cooled to 0° C. and treated with triethylamine (11.7 mL, 83.9 mmol) and 4-(dimethylamino)pyridine (99%, 827 mg, 6.70 mmol). A solution of 4-nitrobenzoyl chloride (15.6 g, 84.1 mmol) in dichloromethane (100 mL) was then added, and the reaction mixture was allowed to slowly warm to room temperature over 18 hours. Dichloromethane (500 mL) was added, and the solution was washed with aqueous hydrochloric acid (1 M, 250 mL), dried over sodium sulfate, filtered and concentrated in vacuo. Purification via silica gel chromatography (Gradient: 0% to 3% ethyl acetate in dichloromethane) afforded the product as a pale yellow solid. Yield: 23 g, 62 mmol, 92%. $^1$H NMR (400 MHz, CDCl$_3$) δ 8.24-8.34 (m, 4H), 5.28-5.33 (m, 1H), 4.55 (br d, J=9 Hz, 1H), 4.19-4.30 (br m, 1H), 3.71-3.87 (m, 2H), 1.38 (br s, 9H), 1.25 (d, J=6.8 Hz, 3H).

Step 4. Synthesis of tert-butyl {(1S)-1-[(2R)-oxiran-2-yl]ethyl}carbamate (C46)

An aqueous solution of potassium hydroxide (23.9 g of 85% purity, 362 mmol, in 160 mL water) was added drop-wise to a 0° C. solution of C45 (27 g, 72 mmol) in ethanol (1 L), and the reaction mixture was stirred for 1 hour at 0° C. At that point, it was diluted with water (1 L) and extracted with tert-butyl methyl ether (2×500 mL). The combined organic layers were washed with aqueous sodium hydroxide solution (1 M, 2×250 mL), dried over sodium sulfate, filtered, and concentrated in vacuo. Silica gel chromatography (Gradient: 5% to 30% ethyl acetate in heptane) provided the product as a colorless oil. Yield: 11.9 g, 63.6 mmol, 88%. $^1$H NMR (400 MHz, CDCl$_3$) δ 4.41 (br s, 1H), 3.93-4.06 (br m, 1H), 2.99 (ddd, J=3.9, 2.5, 2.5 Hz, 1H), 2.74 (dd, J=4.7, 4.0 Hz, 1H), 2.61 (br dd, J=4.7, 2.7 Hz, 1H), 1.44 (s, 9H), 1.27 (d, J=6.9 Hz, 3H).

Step 5. Synthesis of tert-butyl [(2S,3S)-3-hydroxy-6-(trimethylsilyl)hex-5-yn-2-yl]carbamate (C47)

n-Butyllithium (2.5 M solution in hexanes, 39.7 mL, 99 mmol) was added drop-wise to a −20° C. solution of ethynyl(trimethyl)silane (15 mL, 110 mmol) in toluene (100 mL), at a rate that kept the reaction temperature below −15° C. The reaction mixture was stirred for 15 minutes at this temperature. Dimethylaluminum chloride (97%, 1.0 M solution in hexanes, 96 mL, 96 mmol) was added, and the reaction flask was immersed in an ice bath for 1 hour, then warmed to room temperature for 30 minutes. After cooling the reaction mixture to 0° C., a solution of C46 (6.2 g, 33 mmol) in toluene (50 mL) was added, and stirring was continued at 0° C. for 1 hour, at which time the reaction mixture was warmed to room temperature for 1 hour and subsequently cooled to 0° C. A mixture of saturated aqueous citric acid (100 mL) and water (100 mL) was added, and the ice bath was removed. tert-Butyl methyl ether (500 mL) was added, and the mixture was stirred for 15 minutes; the organic layer was then washed with water (100 mL), dried over sodium sulfate, filtered, and concentrated in vacuo, providing the product as a thick oil. Yield: 7.2 g, 25 mmol, 76%. $^1$H NMR (400 MHz, CDCl$_3$) δ 4.79 (br s, 1H), 3.64-3.74 (m, 2H), 2.48 (dd, half of ABX pattern, J=16.9, 7.4 Hz, 1H), 2.43 (dd, half of ABX pattern, J=16.9, 5.3 Hz, 1H), 2.36 (br s, 1H), 1.45 (s, 9H), 1.24 (d, J=6.6 Hz, 3H), 0.17 (s, 9H).

Step 6. Synthesis of tert-butyl [(2S,3S)-3-hydroxy-hex-5-yn-2-yl]carbamate (C48)

Potassium carbonate (6.97 g, 50.4 mmol) was added to a solution of C47 (7.2 g, 25 mmol) in methanol (50 mL). After stirring at room temperature for 1.5 hours, the reaction mixture was partitioned between water (50 mL) and tert-butyl methyl ether (400 mL). The aqueous layer was extracted with tert-butyl methyl ether (100 mL); the combined organic layers were dried over sodium sulfate, filtered, and concentrated in vacuo to give the product as a thick oil. Yield: 5.0 g, 23 mmol, 92%. $^1$H NMR (400 MHz, CDCl$_3$) δ 4.76 (br s, 1H), 3.67-3.80 (m, 2H), 2.74 (br s, 1H), 2.41-2.44 (m, 2H), 2.06 (dd, J=2.7, 2.6 Hz, 1H), 1.45 (s, 9H), 1.23 (d, J=6.8 Hz, 3H).

Step 7. Synthesis of tert-butyl {(2S,3S)-6-[4-chloro-2-(trifluoromethyl)phenyl]-3-hydroxyhex-5-yn-2-yl}carbamate (C49)

Compound C48 was reacted with 4-chloro-1-iodo-2-(trifluoromethyl)benzene using the general method described for synthesis of C39 in Example 8, except that tert-butyl methyl ether was used in place of diethyl ether, and no recrystallization was carried out in this case. The product was obtained as a thick oil. Yield: 19.2 g, 49.0 mmol, 100%. $^1$H NMR (400 MHz, CDCl$_3$) δ 7.63 (br d, J=2.0 Hz, 1H), 7.44-7.52 (m, 2H), 4.80 (br s, 1H), 3.73-3.84 (m, 2H), 2.63-2.75 (m, 2H), 1.45 (s, 9H), 1.27 (br d, J=6.6 Hz, 3H).

Step 8. Synthesis of tert-butyl [(1S)-1-{(2S)-5-[4-chloro-2-(trifluoromethyl)phenyl]-5-methoxytetrahydrofuran-2-yl}ethyl]carbamate (C50)

p-Toluenesulfonic acid monohydrate (96%, 1.55 g, 7.82 mmol) and di-μ-chlorodichlorobis(ethylene)diplatinum(II) (97%, 545 mg, 0.900 mmol) were added to a solution of C49 (33 g, 84 mmol) and trimethyl orthoformate (40 mL, 360 mmol) in methanol (400 mL), and the reaction mixture was stirred at room temperature for 3 hours. Additional di-μ-chlorodichlorobis(ethylene)diplatinum(II) (97%, 500 mg, 0.82 mmol) was introduced, and stirring was continued for 3 hours. The reaction mixture was poured into saturated aqueous sodium bicarbonate solution (400 mL) and extracted with tert-butyl methyl ether; the combined organic layers were dried over magnesium sulfate, filtered, and concentrated in vacuo to afford the product as a thick oil, which was taken directly to the following reaction.

Step 9. Synthesis of tert-butyl [(1S)-1-{(2S,5R)-5-[4-chloro-2-(trifluoromethyl)phenyl]tetrahydrofuran-2-yl}ethyl]carbamate (C51)

Compound C50 from the previous step was converted to the product using the general method for synthesis of C26 in Example 6. In this case, the quenched reaction was extracted with dichloromethane; the combined organic layers were dried over magnesium sulfate, filtered and concentrated in vacuo. Silica gel chromatography (Gradient: 0% to 10% ethyl acetate in heptane) afforded a solid (41.8 g), which was dissolved in methanol (50 mL) and treated with water (~7 mL) until the solution became cloudy. After stirring for 2 hours, the mixture was filtered, and the isolated solid was rinsed with a 3:7 mixture of methanol and water, providing the product as a solid (6.9 g). The filtrate was concentrated until a precipitate formed; this was isolated via filtration to provide 15 g of a solid, which was treated in the same way to provide additional product as a solid (9.5 g). Total yield over 2 steps: 16.4 g, 41.6 mmol, 50%. $^1$H NMR (400 MHz, CDCl$_3$) δ 7.77 (br d, J=8.4 Hz, 1H), 7.61 (br d, J=2.2 Hz, 1H), 7.53 (br dd, J=8.6, 2.2 Hz, 1H), 5.13 (br dd, J=8, 7 Hz, 1H), 4.67 (br s, 1H), 3.84-3.94 (m, 2H), 2.32-2.42 (m, 1H), 2.01-2.11 (m, 1H), 1.78-1.89 (m, 1H), 1.58-1.68 (m, 1H), 1.47 (s, 9H), 1.26 (d, J=6.5 Hz, 3H).

Step 10. Synthesis of (1S)-1-{(2S,5R)-5-[4-chloro-2-(trifluoromethyl)phenyl]tetrahydrofuran-2-yl}ethanamine (C52)

Trifluoroacetic acid (25 mL, 340 mmol) was added to a solution of C51 (16.4 g, 41.6 mmol) in dichloromethane (250 mL). The reaction mixture was stirred at room temperature for 18 hours, then poured into aqueous sodium hydroxide solution (1 M, 350 mL). Additional dichloromethane (500 mL) was added, and the aqueous layer was extracted with dichloromethane (2×200 mL). The combined organic layers were dried over sodium sulfate, filtered, and concentrated in vacuo to provide the product as a brown oil. Yield: 12 g, 41 mmol, 98%. $^1$H NMR (400 MHz, CDCl$_3$) δ 7.73 (br d, J=8.4 Hz, 1H), 7.60 (br d, J=2.2 Hz, 1H), 7.50-7.54 (m, 1H), 5.17-5.23 (m, 1H), 3.67-3.74 (m, 1H), 3.01-3.09 (m, 1H), 2.35-2.46 (m, 1H), 1.98-2.09 (m, 1H), 1.59-1.74 (m, 2H), 1.14 (d, J=6.5 Hz, 3H).

Step 11. Synthesis of N-[(1S)-1-{(2S,5R)-5-[4-chloro-2-(trifluoromethyl)phenyl]tetrahydrofuran-2-yl}ethyl]-1-(2-hydroxyethyl)-5-(4-methyl-1H-imidazol-1-yl)-6-oxo-1,6-dihydropyridine-2-carboxamide (C53)

Compound C52 was converted to the product using the general method employed for synthesis of C42 in Example 8, except that C53 was not stirred with diethyl ether. The product was obtained as an off-white solid. Yield: 21 g, 39 mmol, 95%. LCMS m/z 539.3 [M+H$^+$]. $^1$H NMR (400 MHz, CDCl$_3$) δ 8.12 (br d, J=9 Hz, 1H), 8.00-8.02 (m, 1H), 7.89 (br d, J=8.5 Hz, 1H), 7.62 (d, J=2.2 Hz, 1H), 7.56 (br dd, J=8.5, 2 Hz, 1H), 7.22 (d, J=7.5 Hz, 1H), 7.00-7.02 (m, 1H), 6.39 (d, J=7.6 Hz, 1H), 5.22 (br dd, J=8, 7 Hz, 1H), 4.36-4.46 (m, 1H), 4.27-4.31 (m, 2H), 3.93-4.07 (m, 2H), 3.72-3.78 (m, 1H), 2.40-2.49 (m, 1H), 2.16-2.26 (m, 1H), 2.14 (d, J=0.9 Hz, 3H), 1.7-1.9 (m, 2H), 1.36 (d, J=6.7 Hz, 3H).

Step 12. Synthesis of 2-[(1S)-1-{(2S,5R)-5-[4-chloro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione (9)

Compound C53 was converted to the product using the general method described for synthesis of 8 in Example 8, except for the purification. In this case, after silica gel chromatography (Gradient: 0% to 5% methanol in dichloromethane), material from the chromatography was recrystallized from ethyl acetate to provide the product. The filtrate from the recrystallization was concentrated, triturated with diethyl ether, and recrystallized from ethyl acetate to provide additional product. These two lots were combined (25 g), slurried in tert-butyl methyl ether (50 mL) and warmed to 50° C. for 15 minutes. Cooling and isolation via filtration afforded the product as an off-white solid. Yield: 24.7 g, 47.4 mmol, 72%. LCMS m/z 521.3 [M+H$^+$]. $^1$H NMR (400 MHz, CDCl$_3$) δ 8.30 (br s, 1H), 7.70 (br d, J=8.4 Hz, 1H), 7.57 (br d, J=2.2 Hz, 1H), 7.52 (dd, J=8.3, 2.1 Hz, 1H), 7.48 (d, J=7.8 Hz, 1H), 7.30 (d, J=7.8 Hz, 1H), 7.12-7.14 (m, 1H), 5.14-5.20 (m, 1H), 4.93 (dq, J=9.4, 6.8 Hz, 1H), 4.43 (ddd, half of ABXY pattern, J=14.1, 7.0, 3.9 Hz, 1H), 4.26 (ddd, half of ABXY pattern, J=14.1, 8.0, 4.1 Hz, 1H), 4.06 (ddd, J=9.3, 7.1, 6.6 Hz, 1H), 3.74 (ddd, half of ABXY pattern, J=13.4, 8.0, 4.0 Hz, 1H), 3.66 (ddd, half of ABX pattern, J=13.4, 7.1, 4.1 Hz, 1H), 2.38-2.48 (m, 1H), 2.31 (d, J=1.0 Hz, 3H), 2.17-2.27 (m, 1H), 1.70-1.88 (m, 2H), 1.31 (d, J=6.8 Hz, 3H).

Example 10

2-[(1S)-1-{(2S,5R)-5-[3,5-Difluoro-4-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione (10)

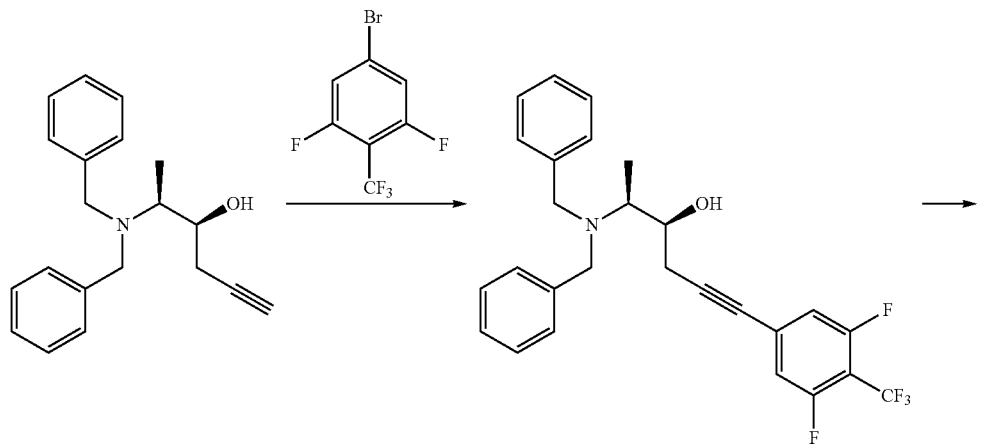

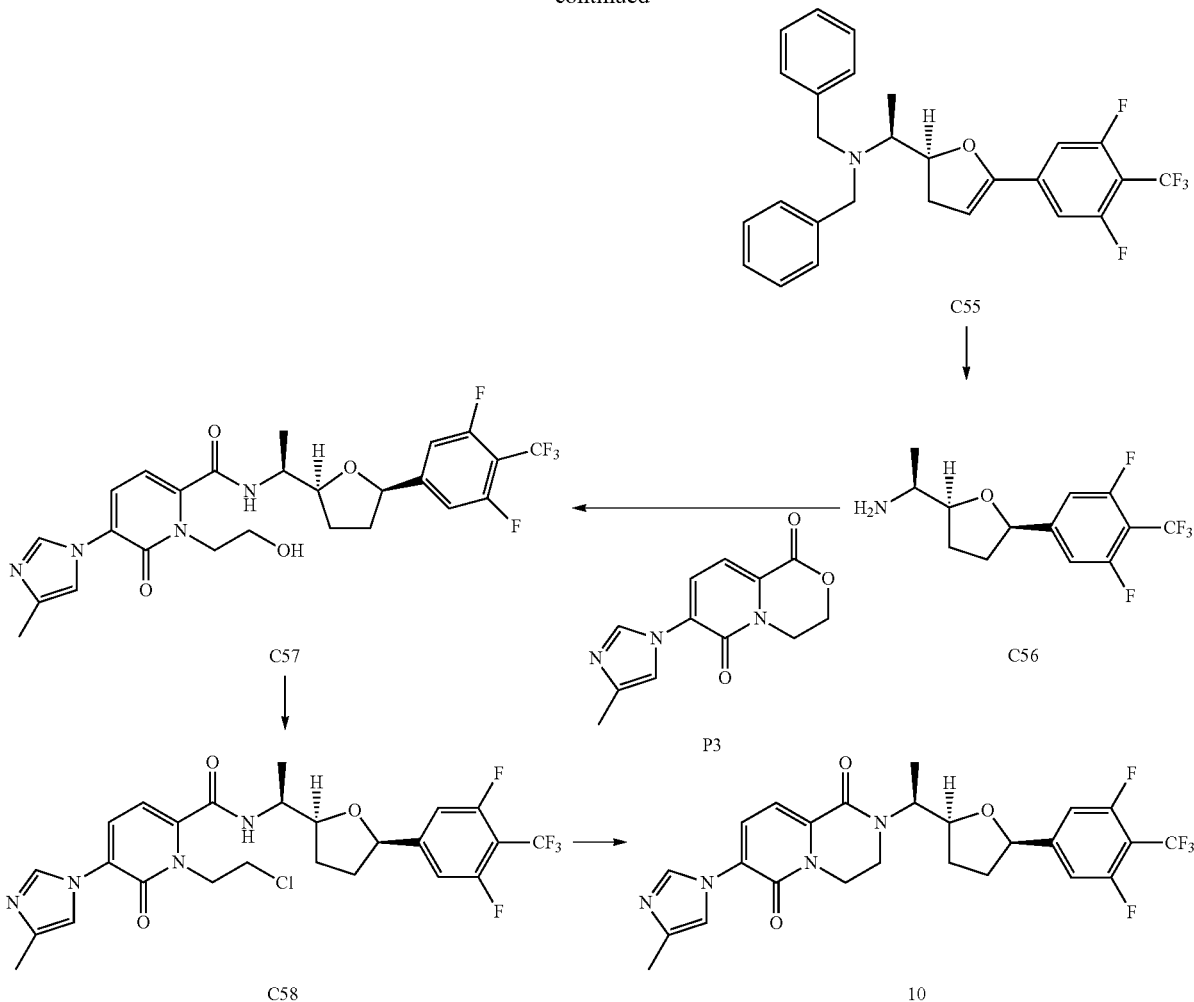

Step 1. Synthesis of (2S,3S)-2-(dibenzylamino)-6-[3,5-difluoro-4-(trifluoromethyl)phenyl]hex-5-yn-3-ol (C54)

Compound C38 was converted to the product via reaction with 5-bromo-1,3-difluoro-2-(trifluoromethyl)benzene, using the method described for synthesis of C49 in Example 9. The product was obtained as a solid. Yield: 3.10 g, 6.55 mmol, 96%. LCMS m/z 474.2 [M+H$^+$]. $^1$H NMR (400 MHz, CDCl$_3$) δ 7.22-7.35 (m, 10H), 6.74 (d, J=10.2 Hz, 2H), 4.56 (s, 1H), 3.86 (d, J=13.3 Hz, 2H), 3.68-3.76 (m, 1H), 3.34 (d, J=13.3 Hz, 2H), 2.85-2.96 (m, 1H), 2.79 (dd, J=17.4, 3.7 Hz, 1H), 2.47 (dd, J=17.4, 4.3 Hz, 1H), 1.11 (d, J=6.6 Hz, 3H).

Step 2. Synthesis of (1S)—N,N-dibenzyl-1-{(2S)-5-[3,5-difluoro-4-(trifluoromethyl)phenyl]-2,3-dihydrofuran-2-yl}ethanamine (C55)

Compound C54 was converted to the product using the general method described for synthesis of C40 in Example 8. In this case, the reaction was quenched with saturated aqueous sodium bicarbonate solution rather than aqueous sodium hydroxide solution. The product was isolated as a thick oil. Yield: 1.96 g, 4.14 mmol, 78%. LCMS m/z 474.2 [M+H$^+$]. $^1$H NMR (400 MHz, CDCl$_3$) δ 7.38 (br d, half of AB quartet, J=7.4 Hz, 4H), 7.25-7.30 (m, 4H), 7.15-7.23 (m, 4H), 5.50-5.53 (m, 1H), 4.78 (ddd, J=9.8, 9.8, 7.0 Hz, 1H), 3.91 (d, J=14.0 Hz, 2H), 3.58 (d, J=13.7 Hz, 2H), 2.92-3.01 (m, 1H), 2.68-2.83 (m, 2H), 1.19 (d, J=7.0 Hz, 3H).

Step 3. Synthesis of (1S)-1-{(2S,5R)-5-[3,5-difluoro-4-(trifluoromethyl)phenyl]tetrahydrofuran-2-yl}ethanamine (C56)

The product was prepared from C55 according to the general procedure for the synthesis of C41 in Example 8, except that tert-butyl methyl ether was used in the work-up rather than ethyl acetate. The product was obtained as an oil. Yield: 629 mg, 2.10 mmol, 90%. $^1$H NMR (400 MHz, CDCl$_3$) δ 7.00 (d, J=10.2 Hz, 2H), 4.91 (dd, J=7.2, 6.8 Hz, 1H), 3.70-3.77 (m, 1H), 2.93-3.01 (m, 1H), 2.34-2.44 (m, 1H), 1.99-2.09 (m, 1H), 1.73-1.87 (m, 3H), 1.61-1.71 (m, 1H), 1.11 (d, J=6.6 Hz, 3H).

Step 4. Synthesis of N-[(1S)-1-{(2S,5R)-5-[3,5-difluoro-4-(trifluoromethyl)phenyl]tetrahydrofuran-2-yl}ethyl]-1-(2-hydroxyethyl)-5-(4-methyl-1H-imidazol-1-yl)-6-oxo-1,6-dihydropyridine-2-carboxamide (C57)

Conversion of C56 to the product employed the general method described for synthesis of C42 in Example 8. In this case, the cooled reaction mixture was quenched with aqueous sodium hydroxide solution (1 M, 25 mL), then extracted three times with ethyl acetate. The combined organic layers were dried over sodium sulfate, filtered, and concentrated in vacuo. The residue was triturated with tert-butyl methyl ether to afford the product as a white solid. Yield: 730 mg, 1.35 mmol, 65%. $^1$H NMR (400 MHz, CDCl$_3$) δ 8.61 (br d, J=9 Hz, 1H), 7.96 (br s, 1H), 7.17 (d, J=7.6 Hz, 1H), 7.11 (br d, J=10.3 Hz, 2H), 6.98-7.00 (m, 1H), 6.41 (d, J=7.4 Hz, 1H), 4.95 (dd, J=7.2, 6.6 Hz, 1H), 4.30-4.46 (m, 3H), 4.07-4.18 (m, 2H), 3.94-4.02 (m, 1H), 2.41-2.50 (m, 1H), 2.12-2.22 (m, 1H), 2.08 (br s, 3H), 1.74-1.93 (m, 2H), 1.35 (d, J=6.6 Hz, 3H).

Step 5. Synthesis of 1-(2-chloroethyl)-N-[(1S)-1-{(2S,5R)-5-[3,5-difluoro-4-(trifluoromethyl)phenyl]tetrahydrofuran-2-yl}ethyl]-5-(4-methyl-1H-imidazol-1-yl)-6-oxo-1,6-dihydropyridine-2-carboxamide (C58)

Thionyl chloride (1.0 mL, 14 mmol) was added to a 0° C. mixture of C57 (1.00 g, 1.85 mmol) in dichloromethane (20 mL). The ice bath was removed, and the reaction mixture was stirred at room temperature for 2 hours, then cooled to 0° C. and quenched with saturated aqueous sodium bicarbonate solution. The aqueous layer was extracted with ethyl acetate, and the combined organic layers were dried over sodium sulfate, filtered, and concentrated in vacuo to provide the product as a sticky yellow foam, which was taken directly to the following step. Yield: 1.00 g, 1.79 mmol, 97%. LCMS m/z 559.1 [M+H$^+$].

Step 6. Synthesis of 2-[(1S)-1-{(2S,5R)-5-[3,5-difluoro-4-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione (10)

Lithium bis(trimethylsilyl)amide (1 M solution in THF, 2.24 mL, 2.24 mmol) was added drop-wise to a 0° C. solution of C58 (from the preceding step, 1.00 g, 1.79 mmol) in tetrahydrofuran (20 mL), and the reaction mixture was stirred at 0° C. for 15 minutes. The ice bath was removed, and stirring was continued for 1 hour. After cooling to 0° C., the reaction was quenched with saturated aqueous ammonium chloride solution and extracted with ethyl acetate. The combined organic layers were dried over sodium sulfate, filtered, and concentrated in vacuo. Silica gel chromatography (Gradient: 0% to 20% methanol in ethyl acetate) provided a pale yellow foam (709 mg), which was recrystallized from tert-butyl methyl ether to afford the product as a white solid. Yield (two crops): 404 mg, 0.773 mmol, 43%. LCMS m/z 523.3 [M+H$^+$]. $^1$H NMR (400 MHz, CDCl$_3$) δ 8.30 (br s, 1H), 7.49 (d, J=7.8 Hz, 1H), 7.34 (d, J=7.8 Hz, 1H), 7.13-7.15 (m, 1H), 6.98 (br d, J=10.3 Hz, 2H), 4.81-4.89 (m, 2H), 4.51 (ddd, J=14.2, 6.2, 4.1 Hz, 1H), 4.21 (ddd, J=14.2, 8.2, 4.1 Hz, 1H), 4.07-4.14 (m, 1H), 3.63-3.77 (m, 2H), 2.38-2.47 (m, 1H), 2.31 (s, 3H), 2.17-2.26 (m, 1H), 1.76-1.92 (m, 2H), 1.31 (d, J=6.8 Hz, 3H).

Examples 11 and 12

7-(4-Methyl-1H-imidazol-1-yl)-2-({(2S,5R)-5-methyl-5-[4-(trifluoromethyl)phenyl]tetrahydrofuran-2-yl}methyl)-3,4-dihydro-2H-pyrido[1,2-a]pyrazine-1,6-dione (11) and 7-(4-Methyl-1H-imidazol-1-yl)-2-({(2R,5S)-5-methyl-5-[4-(trifluoromethyl)phenyl]tetrahydrofuran-2-yl}methyl)-3,4-dihydro-2H-pyrido[1,2-a]pyrazine-1,6-dione (12)

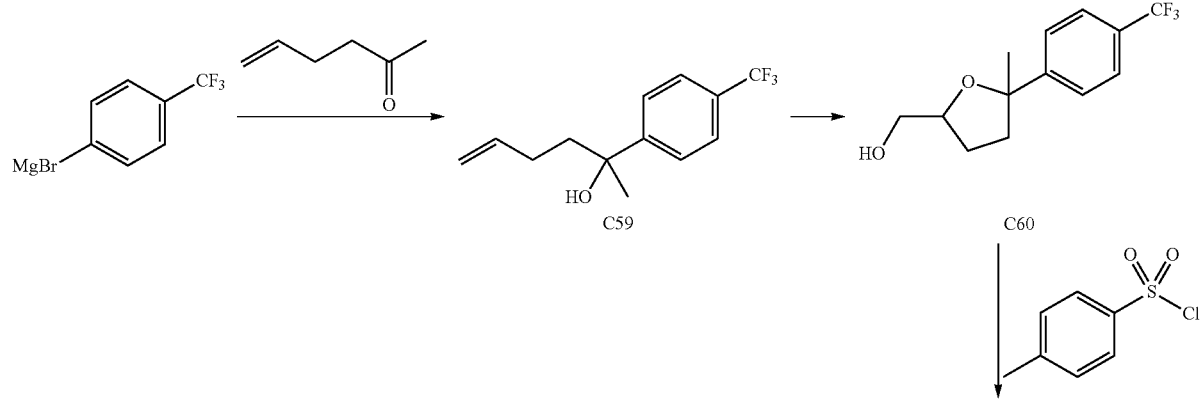

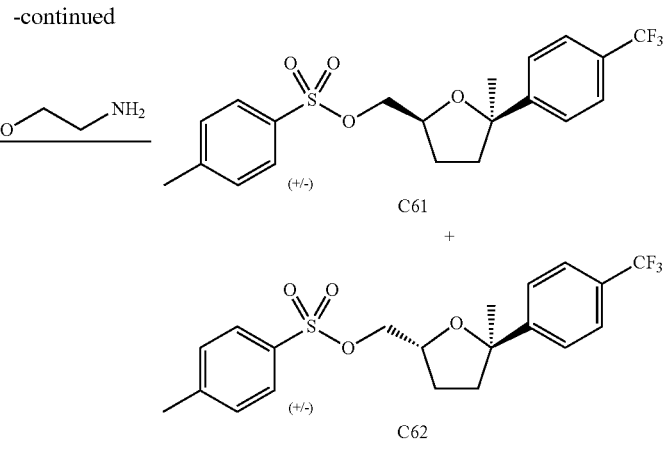

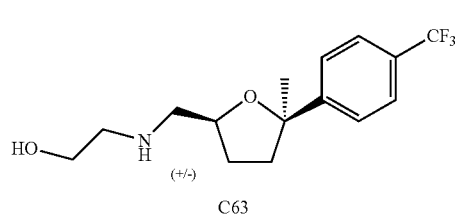

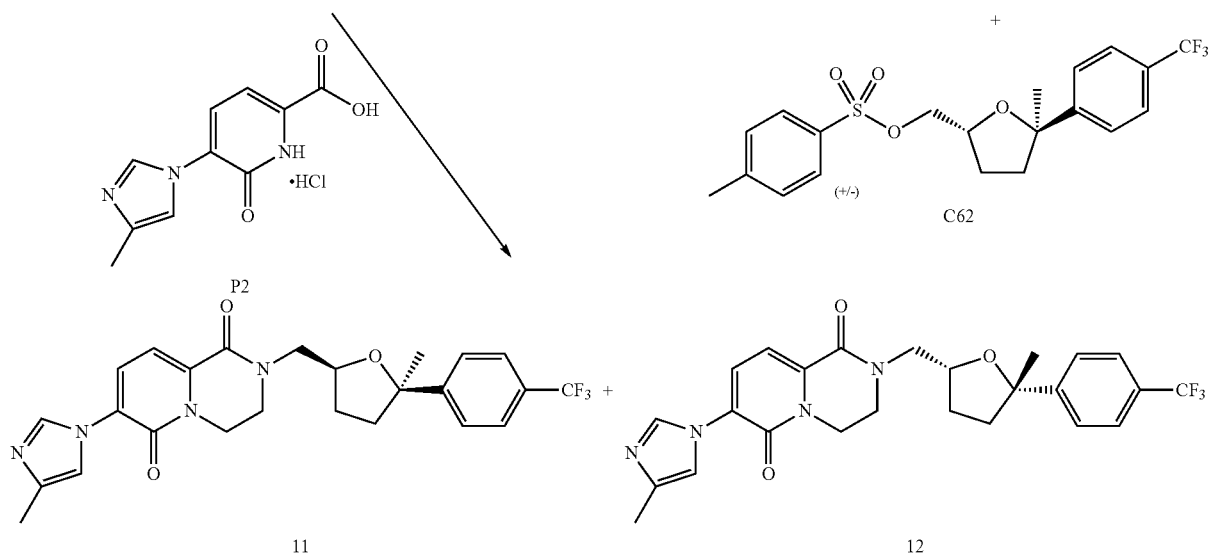

Step 1. Synthesis of 2-[4-(trifluoromethyl)phenyl]hex-5-en-2-ol (C59)

A solution of hex-5-en-2-one (1.00 g, 10.2 mmol) in tetrahydrofuran (3 mL) was added to [4-(trifluoromethyl)phenyl]magnesium bromide (0.26 M solution in tetrahydrofuran, 50 mL, 13 mmol) at 0° C. After 15 minutes at 0° C., the reaction mixture was heated at 70° C. for 18 hours, then cooled to room temperature, diluted with ethyl acetate, and washed with saturated aqueous ammonium chloride solution, with water, and with saturated aqueous sodium chloride solution. The organic layer was dried over magnesium sulfate, filtered, and concentrated in vacuo. Purification via silica gel chromatography (Gradient: 10% to 30% ethyl acetate in heptane) afforded the product as a dark gold oil. Yield: 1.86 g, 7.61 mmol, 75%. $^1$H NMR of crude product (400 MHz, CDCl$_3$), characteristic peaks: δ 7.59 (br AB quartet, $J_{AB}$=8 Hz, $\Delta v_{AB}$=19 Hz, 4H), 5.74-5.85 (m, 1H), 4.93-5.01 (m, 2H), 1.59 (s, 3H).

Step 2. Synthesis of {5-methyl-5-[4-(trifluoromethyl)phenyl]tetrahydrofuran-2-yl}methanol (C60)

3-Chloroperoxybenzoic acid (70%, 3.73 g, 15.1 mmol) was added to a solution of C59 (1.85 g, 7.57 mmol) in dichloromethane (50 mL). After 3 hours, the reaction mixture was washed with 10% aqueous sodium sulfite solution, with saturated aqueous sodium bicarbonate solution, and with water. The organic layer was dried over magnesium sulfate, filtered, and concentrated in vacuo. By $^1$H NMR, this crude product contained a minor amount of the intermediate epoxide [characteristic epoxide peaks at 400 MHz, in CDCl$_3$: 2.87-2.92 (m, 1H), 2.75 (dd, J=4.7, 4.1 Hz, 1H), 2.45 (dd, J=4.9, 2.7 Hz, 1H)]. The crude product was therefore dissolved in dichloromethane (30 mL), treated with p-toluenesulfonic acid monohydrate (142 mg, 0.746 mmol) and allowed to stir at room temperature for 18 hours. The reaction mixture was then washed with saturated aqueous sodium bicarbonate solution and with water, dried over magnesium sulfate, filtered, and concentrated under reduced pressure. Purification via silica gel chromatography (Gradient: 20% to 40% ethyl acetate in heptane) provided the product as a yellow oil, which by $^1$H NMR analysis consisted of a roughly 1:1 mixture of diastereomers. Yield: 1.65 g, 6.34 mmol, 84%. $^1$H NMR (400 MHz, CDCl$_3$), characteristic peaks: δ 7.49-7.61 (m, 4H), [4.29-4.37 (m) and 4.13-4.20 (m), total 1H], [3.78 (br dd, J=11.6, 2.4 Hz) and 3.71 (br dd, J=11.4, 2.8 Hz), total 1H], 3.54-3.64 (m, 1H), 2.03-2.28 (m, 3H), 1.55 and 1.53 (2 s, total 3H).

Step 3. Synthesis of {cis-5-methyl-5-[4-(trifluoromethyl)phenyl]tetrahydrofuran-2-yl}methyl 4-methylbenzenesulfonate (C61)

4-Methylbenzenesulfonyl chloride (98%, 1.60 g, 8.22 mmol) was added to a solution of C60 (1.65 g, 6.34 mmol) and triethylamine (1.32 mL, 9.47 mmol) in dichloromethane (25 mL) at 0° C., and the reaction mixture was allowed to slowly warm to room temperature as the ice bath melted. After 18 hours, the solution was washed with saturated aqueous sodium bicarbonate solution and with water. The organic layer was concentrated in vacuo and purified via silica gel chromatography (Gradient: 10% to 40% ethyl acetate in heptane). The product, which was the more polar isomer, was obtained as a white solid. Yield: 830 mg, 2.00 mmol, 32%. $^1$H NMR (400 MHz, CDCl$_3$) δ 7.79 (br d, J=8.4 Hz, 2H), 7.44 (br AB quartet, $J_{AB}$=8.2 Hz, $\Delta v_{AB}$=31.0 Hz, 4H), 7.34 (br d, J=8 Hz, 2H), 4.37-4.44 (m, 1H), 4.05 (dd, half of ABX pattern, J=10.1, 4.4 Hz, 1H), 4.00 (dd, half of ABX pattern, J=10.1, 5.8 Hz, 1H), 2.47 (s, 3H), 2.08-2.22

(m, 3H), 1.62-1.71 (m, 1H), 1.48 (s, 3H). Also obtained was the less polar isomer {trans-5-methyl-5-[4-(trifluoromethyl)phenyl]tetrahydrofuran-2-yl}methyl 4-methylbenzenesulfonate (C62), as a thick, colorless gum (878 mg). $^1$H NMR (400 MHz, CDCl$_3$) δ 7.84 (br d, J=8.4 Hz, 2H), 7.56 (br d, J=8.5 Hz, 2H), 7.44 (br d, J=8.5 Hz, 2H), 7.35-7.39 (m, 2H), 4.19-4.26 (m, 1H), 4.06-4.14 (m, 2H), 2.46 (s, 3H), 2.16-2.24 (m, 1H), 2.04-2.12 (m, 1H), 1.82-1.89 (m, 2H), 1.47 (s, 3H). The indicated relative stereochemistries of C61 and C62 were assigned based on NOE studies.

Step 4. Synthesis of 2-[({cis-5-methyl-5-[4-(trifluoromethyl)phenyl]tetrahydrofuran-2-yl}methyl)amino]ethanol (C63)

A mixture of 2-aminoethanol (856 mg, 14.0 mmol) and C61 (830 mg, 2.00 mmol) in acetonitrile (10 mL) was heated at 90° C. for 18 hours, then cooled to room temperature, diluted with ethyl acetate, and washed with water and with saturated aqueous sodium chloride solution. The organic layer was dried over magnesium sulfate, filtered, and concentrated in vacuo to provide the product as a light yellow oil. Yield: 559 mg, 1.84 mmol, 92%. LCMS m/z 304.1 [M+H$^+$]. $^1$H NMR (400 MHz, CDCl$_3$) δ 7.56 (br AB quartet, J$_{AB}$=8.4 Hz, Δv$_{AB}$=15.9 Hz, 4H), 4.29-4.37 (m, 1H), 3.65 (t, J=5.3 Hz, 2H), 2.79-2.91 (m, 2H), 2.74 (d, J=5.9 Hz, 2H), 2.06-2.25 (m, 3H), 1.54-1.64 (m, 1H), 1.52 (s, 3H).

Step 5. Synthesis of 7-(4-methyl-1H-imidazol-1-yl)-2-({(2S,5R)-5-methyl-5-[4-(trifluoromethyl)phenyl]tetrahydrofuran-2-yl}methyl)-3,4-dihydro-2H-pyrido[1,2-a]pyrazine-1,6-dione (11) and 7-(4-methyl-1H-imidazol-1-yl)-2-({(2R,5S)-5-methyl-5-[4-(trifluoromethyl)phenyl]tetrahydrofuran-2-yl}methyl)-3,4-dihydro-2H-pyrido[1,2-a]pyrazine-1,6-dione (12)

Compound C63 was converted to the products using the general method described for synthesis of 6 in Example 6. In this case, silica gel chromatography was carried out using a gradient of 0% to 20% methanol in ethyl acetate. The racemic product was separated into its enantiomers via supercritical fluid chromatography (Column: Chiralcel OJ-H, 5 μm; Eluent: 4:1 carbon dioxide/methanol containing 0.2% isopropylamine). The first-eluting peak was Example 11, obtained as a solid. Yield: 47 mg, 97 μmol, 5%. LCMS m/z 487.2 [M+H$^+$]. $^1$H NMR (400 MHz, CDCl$_3$) δ 8.23 (d, J=1.4 Hz, 1H), 7.57 (br AB quartet, J$_{AB}$=8.2 Hz, Δv$_{AB}$=36.4 Hz, 4H), 7.46 (d, J=7.6 Hz, 1H), 7.28 (d, J=7.6 Hz, 1H, assumed; partially obscured by solvent peak), 7.14-7.15 (m, 1H), 4.39-4.51 (m, 2H), 4.28 (ddd, half of ABXY pattern, J=14.3, 8.0, 4.1 Hz, 1H), 4.10 (dd, J=13.9, 3.1 Hz, 1H), 4.01 (ddd, J=13.5, 8.0, 4.1 Hz, 1H), 3.80 (ddd, J=13.5, 7.2, 4.1 Hz, 1H), 3.34 (dd, J=14.0, 8.1 Hz, 1H), 2.30 (d, J=1.0 Hz, 3H), 2.17-2.25 (m, 3H), 1.63-1.73 (m, 1H), 1.50 (s, 3H). The second-eluting peak was Example 12, obtained as a solid. Yield: 39 mg, 80 μmol, 4%. LCMS m/z 487.2 [M+H$^+$]. $^1$H NMR (400 MHz, CDCl$_3$) δ 8.22 (d, J=1.2 Hz, 1H), 7.59-7.63 (m, 2H), 7.50-7.54 (m, 2H), 7.46 (d, J=7.6 Hz, 1H), 7.28 (d, J=7 Hz, 1H, assumed; partially obscured by solvent peak), 7.13-7.15 (m, 1H), 4.39-4.50 (m, 2H), 4.28 (ddd, half of ABXY pattern, J=14.2, 7.9, 4.0 Hz, 1H), 4.10 (dd, J=13.9, 3.1 Hz, 1H), 4.01 (ddd, J=13.5, 7.9, 4.0 Hz, 1H), 3.80 (ddd, J=13.5, 7.2, 4.1 Hz, 1H), 3.33 (dd, J=14.0, 8.1 Hz, 1H), 2.29 (d, J=1.0 Hz, 3H), 2.17-2.25 (m, 3H), 1.63-1.73 (m, 1H), 1.50 (s, 3H). The absolute stereochemistries of these compounds were assigned on the basis of the difference in their IC$_{50}$ values (see Table 1); compounds with the (2S,5R) configuration around the tetrahydrofuran ring are generally more potent than their (2R,5S) enantiomers.

Examples 13 and 14

7-(4-Methyl-1H-imidazol-1-yl)-2-({cis-2-methyl-5-[4-(trifluoromethyl)phenyl]tetrahydrofuran-2-yl}methyl)-3,4-dihydro-2H-pyrido[1,2-a]pyrazine-1,6-dione, formate salt (13) and 7-(4-Methyl-1H-imidazol-1-yl)-2-({trans-2-methyl-5-[4-(trifluoromethyl)phenyl]tetrahydrofuran-2-yl}methyl)-3,4-dihydro-2H-pyrido[1,2-a]pyrazine-1,6-dione, formate salt (14)

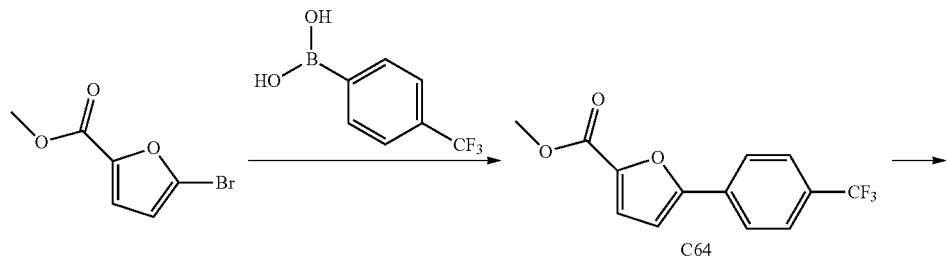

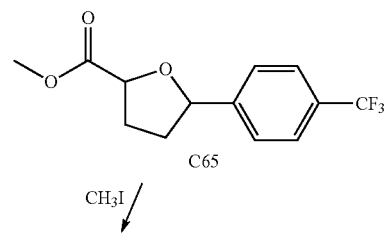

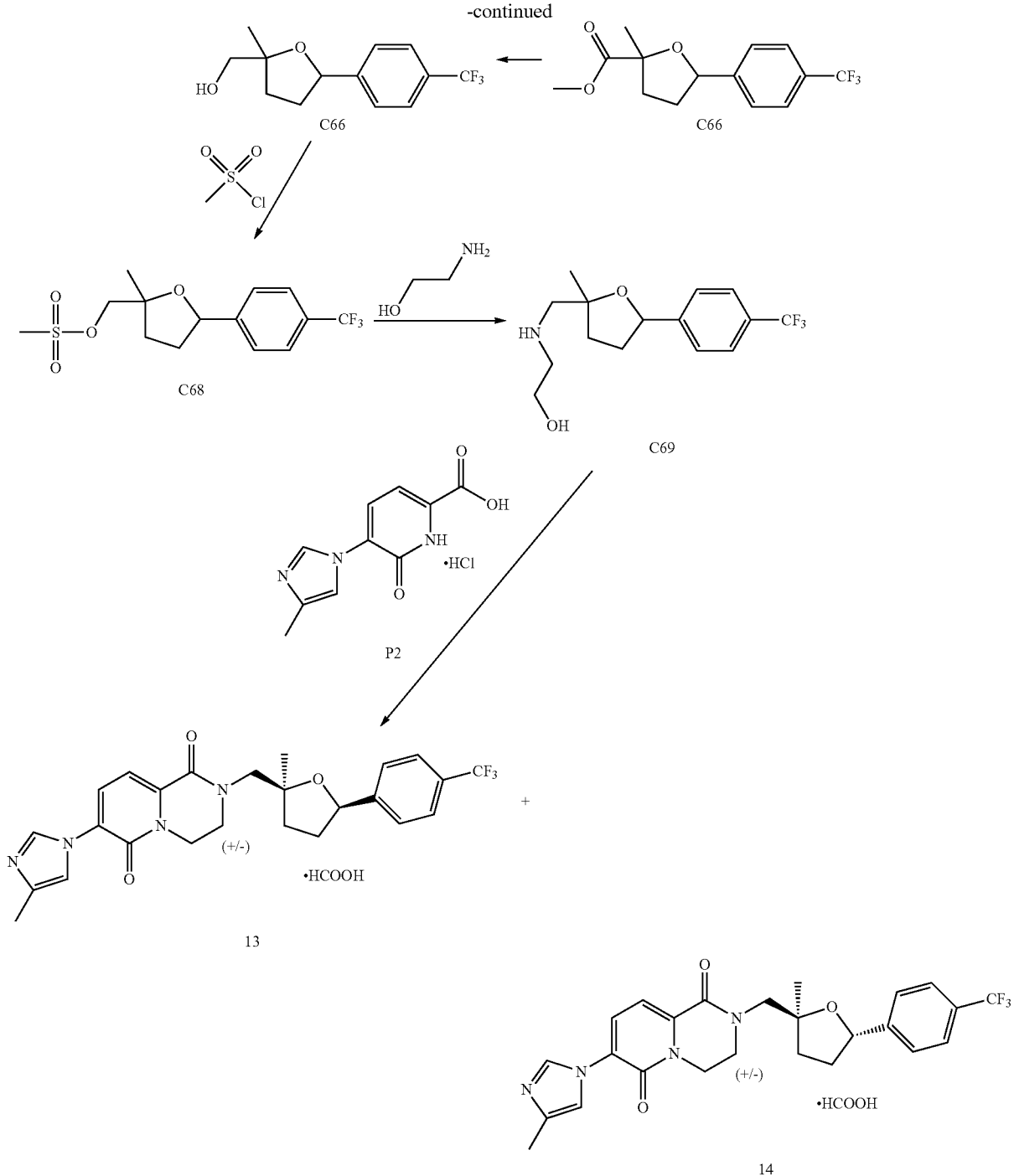

Step 1. Synthesis of methyl 5-[4-(trifluoromethyl)phenyl]furan-2-carboxylate (C64)

Methyl 5-bromofuran-2-carboxylate (497 mg, 2.42 mmol) and 4-(trifluoromethyl)phenyl]boronic acid (472 mg, 2.48 mmol) were combined in 1,4-dioxane (5 mL). Saturated aqueous sodium bicarbonate solution (5.0 mL) was added, followed by tetrakis(triphenylphosphine)palladium (0) (140 mg, 0.121 mmol), and the reaction mixture was heated in a microwave reactor at 150° C. for 20 minutes. After dilution with dichloromethane (20 mL) and water (20 mL), the layers were separated and the aqueous layer was extracted with dichloromethane (10 mL). The combined organic layers were dried over magnesium sulfate, filtered, and concentrated in vacuo. Purification via silica gel chromatography (Gradient: 0% to 50% ethyl acetate in heptane) afforded the product as a pale off-white solid. Yield: 298 mg, 1.10 mmol, 45%. LCMS m/z 271.0 [M+H⁺]. $^1$H NMR (500 MHz, CDCl$_3$) δ 7.90 (br d, J=8.3 Hz, 2H), 7.68 (br d, J=8.4 Hz, 2H), 7.28 (d, J=3.7 Hz, 1H), 6.86 (d, J=3.7 Hz, 1H), 3.94 (s, 3H).

Step 2. Synthesis of methyl 5-[4-(trifluoromethyl)phenyl]tetrahydrofuran-2-carboxylate (C65)

Palladium hydroxide on carbon (~50% water, 10 wt % palladium, 650 mg, 0.46 mmol) was added to a solution of C64 (6.5 g, 32 mmol) in ethanol (170 mL), and the reaction mixture was hydrogenated for 3 hours at room temperature. The catalyst was removed via filtration; the filtrate was concentrated in vacuo and purified via supercritical fluid chromatography (Column: Chiralpak AD-H, 5 µm; Eluent: 9:1 carbon dioxide/methanol), providing the product as an oil. Starting material C64 was also recovered (2 g). Yield: 3.0 g, 11 mmol, 34% (44% based on recovered starting material). $^1$H NMR (400 MHz, CDCl$_3$) δ 7.63 (br AB quartet, J$_{AB}$=8.5 Hz, Δv$_{AB}$=15 Hz, 4H), 5.09 (dd, J=8.9, 5.8 Hz, 1H), 4.65-4.69 (m, 1H), 3.81 (s, 3H), 2.33-2.45 (m, 2H), 2.18-2.27 (m, 1H), 1.84-1.95 (m, 1H).

Step 3. Synthesis of methyl 2-methyl-5-[4-(trifluoromethyl)phenyl]tetrahydrofuran-2-carboxylate (C66)

A −100° C. solution of potassium bis(trimethylsilyl)amide (1 M in tetrahydrofuran, 9.1 mL, 9.1 mmol) was added to a solution of C65 (1.25 g, 4.56 mmol) and iodomethane (98%, 2.90 mL, 45.6 mmol) in diethyl ether (5 mL) at −100° C., and the reaction mixture was allowed to gradually warm to room temperature. Upon reaction completion, aqueous citric acid solution (1 M, 5 mL) was added. The aqueous layer was extracted with diethyl ether (2×10 mL), and the combined organic layers were washed with saturated aqueous sodium chloride solution, dried over magnesium sulfate, filtered, and concentrated in vacuo. Silica gel chromatography (Eluent: 4:1 heptane/ethyl acetate) provided the product. By $^1$H NMR, this material appeared to be a roughly 1:1 mixture, presumed to consist of the cis and trans isomers of the product. Yield: 560 mg, 1.94 mmol, 42%. $^1$H NMR (400 MHz, CDCl$_3$) δ {7.60 (s) and [7.60 (br d, J=8 Hz) and 7.45-7.49 (m)], total 4H}, [5.20 (dd, J=7.0, 7.0 Hz) and 5.14 (dd, J=9.4, 5.8 Hz), total 1H], 3.80 and 3.79 (2 s, total 3H), 2.34-2.58 (m, 2H), 1.82-2.07 (m, 2H), 1.65 and 1.60 (2 s, total 3H).

Step 4. Synthesis of {2-methyl-5-[4-(trifluoromethyl)phenyl]tetrahydrofuran-2-yl}methanol (C67)

Lithium aluminum hydride (2 M solution in tetrahydrofuran, 0.26 mL, 0.52 mmol) was added to a solution of C66 (125 mg, 0.434 mmol) in diethyl ether (2 mL), and the reaction mixture was stirred at room temperature for 1 hour. After acidification with aqueous hydrochloric acid, the mixture was extracted with ethyl acetate, and the combined organic layers were dried over magnesium sulfate, filtered, and concentrated in vacuo to afford the product as an oil, presumed to be a ~1:1 mixture of stereoisomers. Yield: 85 mg, 0.33 mmol, 76%. $^1$H NMR (400 MHz, CDCl$_3$) δ 7.59 (br d, J=8.2 Hz, 2H), 7.43-7.49 (m, 2H), 4.97-5.08 (m, 1H), 3.51-3.63 (m, 2H), 2.32-2.44 (m, 1H), 2.08-2.19 (m, 1H), 1.76-1.95 (m, 2H), 1.34 and 1.33 (2 s, total 3H).

Step 5. Synthesis of {2-methyl-5-[4-(trifluoromethyl)phenyl]tetrahydrofuran-2-yl}methyl methanesulfonate (C68)

Compound C67 was converted to the product using the general method described for synthesis of C17 in Example 3. The product, isolated as a roughly 1:1 mixture of stereoisomers, was used without additional purification. $^1$H NMR (400 MHz, CDCl$_3$), characteristic peaks: δ 7.60 (br d, J=8.6 Hz, 2H), 7.44-7.50 (m, 2H), 5.04-5.10 (m, 1H), [4.21 (AB quartet, J$_{AB}$=10.4 Hz, Δv$_{AB}$=17.5 Hz) and 4.19 (s), total 2H], 3.08 and 3.03 (2 s, total 3H), 1.44 and 1.41 (2 s, total 3H).

Step 6. Synthesis of 2-[({2-methyl-5-[4-(trifluoromethyl)phenyl]tetrahydrofuran-2-yl}methyl)amino]ethanol (C69)

The product was prepared from C68 using the general method described for synthesis of C9 in Example 1. In this case, the product was used in the next step without HPLC purification. Yield: 295 mg, 0.973 mmol, 94%.

Step 7. Synthesis of 7-(4-methyl-1H-imidazol-1-yl)-2-({cis-2-methyl-5-[4-(trifluoromethyl)phenyl]tetrahydrofuran-2-yl}methyl)-3,4-dihydro-2H-pyrido[1,2-a]pyrazine-1,6-dione, formate salt (13) and 7-(4-methyl-1H-imidazol-1-yl)-2-({trans-2-methyl-5-[4-(trifluoromethyl)phenyl]tetrahydrofuran-2-yl}methyl)-3,4-dihydro-2H-pyrido[1,2-a]pyrazine-1,6-dione, formate salt (14)

Compound C69 was reacted with P2 according to the method described for synthesis of 1 in Example 1. In this case, the crude reaction mixture was simply concentrated in vacuo and the isomers were separated via HPLC (Column: Phenomenex Luna C-18(2), 5 µm; Mobile phase A: 0.1% formic acid in water; Mobile phase B: 0.1% formic acid in methanol; Gradient: 5% to 95% B). Example 13 was the first-eluting isomer, isolated as a glass. Yield: 38 mg, 71 µmol, 7%. LCMS m/z 487.3 [M+H$^+$]. $^1$H NMR (400 MHz, CDCl$_3$) δ 8.39 (s, 1H), 8.23 (br s, 1H), 7.62 (br d, J=8 Hz, 2H), 7.51 (d, J=7.8 Hz, 1H), 7.43 (br d, J=8 Hz, 2H), 7.29 (d, J=7.7 Hz, 1H), 7.14-7.18 (m, 1H), 5.07 (dd, J=7.6, 7.2 Hz, 1H), 4.20-4.35 (m, 2H), 4.11 (d, J=14.0 Hz, 1H), 3.97-4.05 (m, 1H), 3.78-3.86 (m, 1H), 3.50 (d, J=14.0 Hz, 1H), 2.44-2.53 (m, 1H), 2.30 (s, 3H), 2.04-2.13 (m, 1H), 1.92-2.01 (m, 1H), 1.80-1.91 (m, 1H), 1.36 (s, 3H). The second-eluting isomer was Example 14, obtained as a glass. Yield: 26 mg, 49 µmol, 5%. LCMS m/z 487.3 [M+H$^+$]. $^1$H NMR (400 MHz, CDCl$_3$) δ 8.46 (s, 1H), 8.23 (br s, 1H), 7.61 (br d, J=8 Hz, 2H), 7.55 (d J=7.6 Hz, 1H), 7.44 (br d, J=8 Hz, 2H), 7.32 (d, J=7.8 Hz, 1H), 7.16-7.20 (m, 1H), 5.02 (dd, J=9.4, 5.8 Hz, 1H), 4.28-4.43 (m, 2H), 4.03 (ddd, half of ABXY pattern, J=13.7, 7.3, 4.2 Hz, 1H), 3.94 (d, J=14.2 Hz, 1H), 3.85-3.93 (m, 1H), 3.62 (d, J=14.1 Hz, 1H), 2.35-2.44 (m, 1H), 2.32 (s, 3H), 1.85-2.10 (m, 3H), 1.38 (s, 3H). The indicated stereochemistries were assigned on the basis of NOE studies carried out on both isomers.

Examples 15 and 16
7-(4-Methyl-1H-imidazol-1-yl)-2-({trans-6-[4-(trifluoromethyl)phenyl]tetrahydro-2H-pyran-2-yl}methyl)-3,4-dihydro-2H-pyrido[1,2-a]pyrazine-1,6-dione, formate salt (15) and 7-(4-Methyl-1H-imidazol-1-yl)-2-({cis-6-[4-(trifluoromethyl)phenyl]tetrahydro-2H-pyran-2-yl}methyl)-3,4-dihydro-2H-pyrido[1,2-a]pyrazine-1,6-dione, formate salt (16)
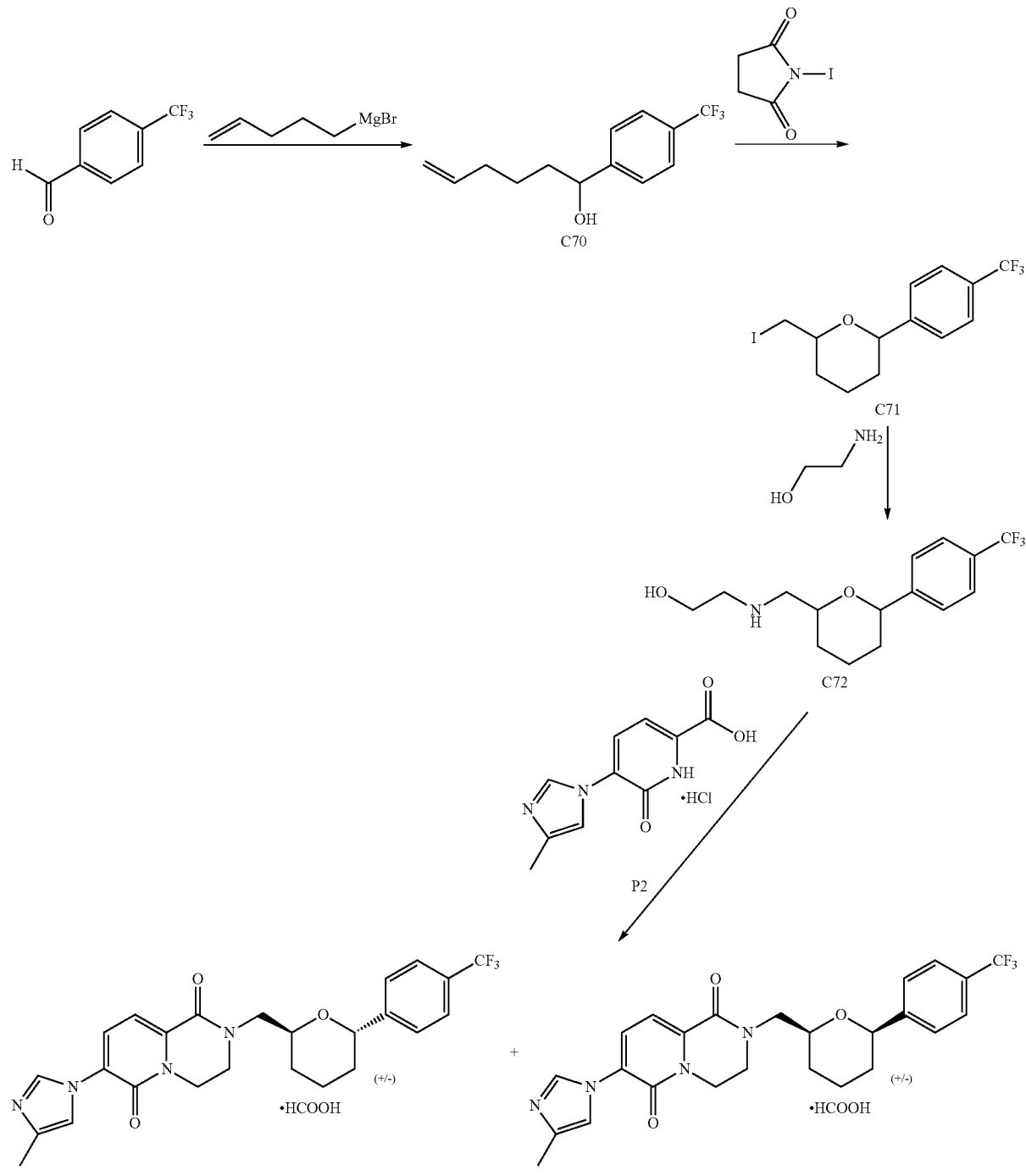

Step 1. Synthesis of
1-[4-(trifluoromethyl)phenyl]hex-5-en-1-ol (C70)

A mixture of 5-bromopent-1-ene (6.0 g, 40 mmol) and magnesium (1.44 g, 59.2 mmol) in tetrahydrofuran (40 mL) was stirred at 0° C. for 30 minutes. 4-(Trifluoromethyl) benzaldehyde (4.6 g, 26 mmol) was added drop-wise, and the reaction mixture was stirred at room temperature for 4 hours, then quenched by addition of water (30 mL). After extraction with ethyl acetate (3×15 mL), the combined organic layers were washed with saturated aqueous sodium chloride solution (10 mL), dried over sodium sulfate, filtered, and concentrated in vacuo to afford the product as a yellow oil. This was used without additional purification. Yield: 2.6 g, 11 mmol, 42%. $^1$H NMR (400 MHz, CDCl$_3$) δ 7.58-7.64 (m, 2H), 7.44-7.50 (m, 2H), 5.72-5.84 (m, 1H), 4.93-5.04 (m, 2H), 4.73-4.79 (m, 1H), 2.05-2.13 (m, 2H), 1.64-1.85 (m, 2H), 1.47-1.60 (m, 1H), 1.34-1.47 (m, 1H).

Step 2. Synthesis of 2-(iodomethyl)-6-[4-(trifluoromethyl)phenyl]tetrahydro-2H-pyran (C71)

To a solution of C70 (2.3 g, 9.4 mmol) in acetonitrile (25 mL) was added N-iodosuccinimide (95%, 5.0 g, 21 mmol), and the reaction mixture was stirred at room temperature for 18 hours. After quenching with water (15 mL), the mixture was extracted with ethyl acetate (3×15 mL), and the combined organic layers were washed with saturated aqueous sodium chloride solution (15 mL), dried over sodium sulfate, filtered, and concentrated in vacuo. Purification via silica gel chromatography (Gradient: 1% to 10% ethyl acetate in petroleum ether) provided the product as a yellow oil. By $^1$H NMR, this consisted of a roughly 2:1 mixture of isomers. Yield: 1.8 g, 4.9 mmol, 52%. $^1$H NMR (400 MHz, CDCl$_3$), characteristic peaks: δ [7.51 (d, J=8.5 Hz) and 7.56-7.67 (m), total 4H], [4.51 (br d, J=11 Hz) and 4.93 (br dd, J=5, 5 Hz), total 1H], [3.48-3.57 (m) and 3.78-3.86 (m), total 1H], 3.26-2.42 (m, 2H).

Step 3. Synthesis of 2-[({6-[4-(trifluoromethyl)phenyl]tetrahydro-2H-pyran-2-yl}methyl)amino]ethanol (C72)

Compound C71 was converted to the product using the method described for synthesis of C29 in Example 6. The product was obtained as a yellow oil, which by $^1$H NMR was estimated to be a roughly 3:1 mixture of isomers. Yield: 1.1 g, 3.6 mmol, 73%. $^1$H NMR (400 MHz, CDCl$_3$), characteristic peaks: δ 7.41-7.66 (m, 4H), [4.43 (br d, J=10.5 Hz) and 4.88 (br dd, J=5, 5 Hz), total 1H].

Step 4. Synthesis of 7-(4-methyl-1H-imidazol-1-yl)-2-({trans-6-[4-(trifluoromethyl)phenyl]tetrahydro-2H-pyran-2-yl}methyl)-3,4-dihydro-2H-pyrido[1,2-a]pyrazine-1,6-dione, formate salt (15) and 7-(4-methyl-1H-imidazol-1-yl)-2-({cis-6-[4-(trifluoromethyl)phenyl]tetrahydro-2H-pyran-2-yl}methyl)-3,4-dihydro-2H-pyrido[1,2-a]pyrazine-1,6-dione, formate salt (16)

Compound C72 was reacted with P2 using the method described for synthesis of 1 in Example 1. In this case, the separation of stereoisomers was carried out via reversed phase HPLC (Column: Boston Analytics, Boston Symmetrix ODS-H, 5 μm; Mobile phase A: 0.225% formic acid in water; Mobile phase B: 0.225% formic acid in acetonitrile; Gradient: 24% to 44% B). Example 16 came off the column before Example 15; both were obtained as white solids. The indicated relative stereochemistry was assigned on the basis of NOE studies. Example 15: Yield, 4.7 mg, 8.8 μmol, 1.3%. LCMS m/z 487.0 [M+H]$^+$. $^1$H NMR (400 MHz, CD$_3$OD) δ 8.57 (br s, 1H), 7.82 (d, J=8.0 Hz, 1H), 7.57 (br AB quartet, J$_{AB}$=8 Hz, Δν$_{AB}$=21 Hz, 4H), 7.39-7.42 (m, 1H), 7.23 (d, J=8.0 Hz, 1H), 5.01-5.06 (m, 1H), 4.30-4.36 (m, 2H), 4.17-4.27 (m, 2H), 3.83-3.88 (m, 2H), 3.48-3.57 (m, 1H), 2.28 (br s, 3H), 1.70-2.0 (m, 5H), 1.56-1.66 (m, 1H). Example 16: 32.8 mg, 61.6 μmol, 9%. $^1$H NMR (400 MHz, CD$_3$OD) δ 9.05 (br s, 1H), 7.93 (d, J=7.5 Hz, 1H), 7.58 (br AB quartet, J$_{AB}$=8.5 Hz, Δν$_{AB}$=31 Hz, 4H), 7.58 (br s, 1H), 7.28 (d, J=7.5 Hz, 1H), 4.52 (br d, J=10.5 Hz, 1H), 4.30-4.38 (m, 1H), 4.21-4.29 (m, 1H), 3.85-3.98 (m, 4H), 3.62 (dd, J=13.8, 8.3 Hz, 1H), 2.36 (s, 3H), 1.97-2.05 (m, 1H), 1.72-1.93 (m, 3H), 1.34-1.52 (m, 2H).

Example 17

7-(4-Methyl-1H-imidazol-1-yl)-2-({(2S,4S,5R)-4-methyl-5-[4-(trifluoromethyl)phenyl]tetrahydrofuran-2-yl}methyl)-3,4-dihydro-2H-pyrido[1,2-a]pyrazine-1,6-dione, trifluoroacetate salt (17)

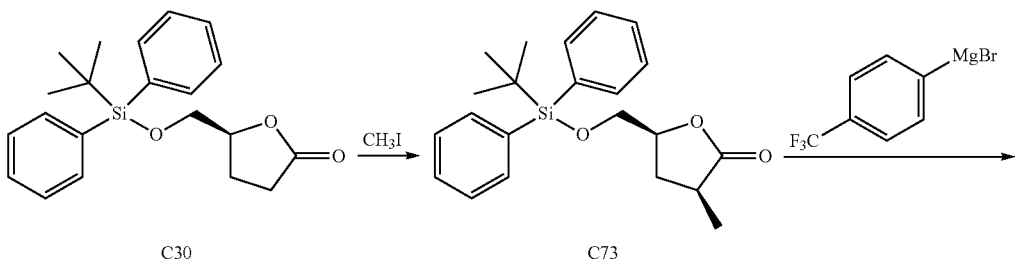

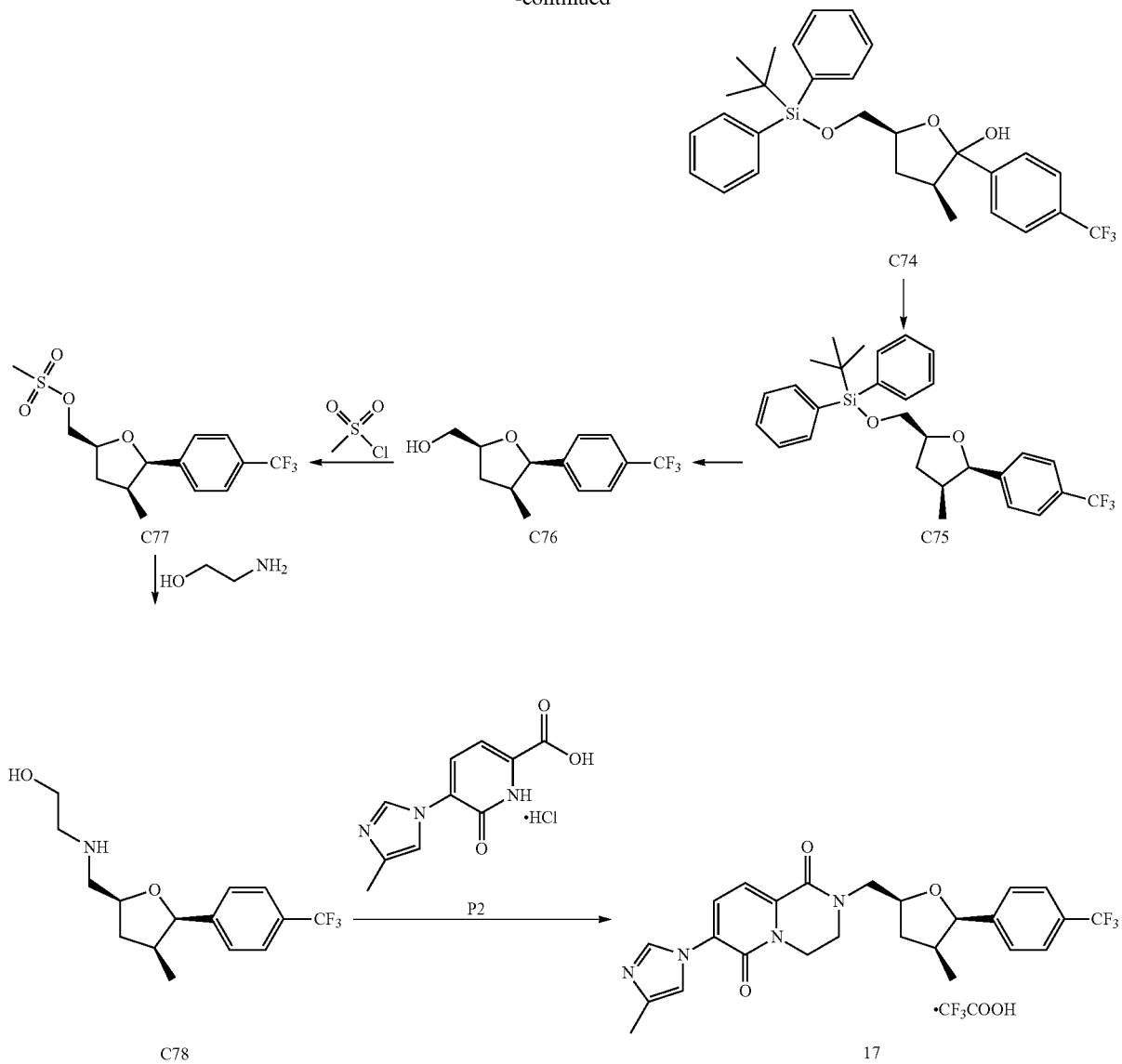

Step 1. Synthesis of (3S,5S)-5-({[tert-butyl(diphenyl)silyl]oxy}methyl)-3-methyldihydrofuran-2(3H)-one (C73)

A solution of C30 (1.02 g, 2.88 mmol) in tetrahydrofuran (15 mL) was added drop-wise to a −78° C. solution of lithium bis(trimethylsilyl)amide (1.0 M in heptane, 3.45 mL, 3.45 mmol) in tetrahydrofuran (12 mL); after 30 minutes, iodomethane (0.215 mL, 3.45 mmol) was added to the cold solution, which was then stirred at −78° C. for 30 minutes, warmed to −50° C. and stirred at that temperature for 3 hours. After quenching with aqueous ammonium chloride solution (50% saturated, 20 mL), diethyl ether (20 mL) was added, and the aqueous layer was extracted with diethyl ether (2×20 mL). The combined organic layers were washed with saturated aqueous sodium chloride solution, dried over sodium sulfate, filtered, and concentrated in vacuo. The resulting oil (1.27 g) was dissolved in tetrahydrofuran (15 mL) and added drop-wise to a −78° C. solution of lithium bis(trimethylsilyl)amide (1.0 M in heptane, 5.0 mL, 5.0 mmol) in tetrahydrofuran (10 mL). After the reaction mixture had stirred at −78° C. for 1 hour, it was allowed to warm briefly to −50° C., then cooled back to −78° C. Saturated aqueous sodium sulfate solution (10 mL) was added, and the mixture was allowed to slowly thaw. Water (10 mL) and diethyl ether (20 mL) were added, and the aqueous layer was extracted with diethyl ether (2×20 mL). The combined organic layers were washed with saturated aqueous sodium chloride solution, dried over sodium sulfate, filtered, and concentrated under reduced pressure. Purification using silica gel chromatography (0% to 50% ethyl acetate in heptane) afforded the product as a colorless oil, which subsequently solidified. The indicated stereochemistry was assigned in accordance with the work of S. F. Martin et al., *J. Org. Chem.* 2000, 65, 1305-1318. Yield: 558 mg, 1.51 mmol, 52%. $^1$H NMR (400 MHz, CDCl$_3$) δ 7.66-7.70 (m, 4H), 7.38-7.48 (m, 6H), 4.44-4.51 (m, 1H), 3.87 (dd, half of ABX pattern, J=11.3, 3.7 Hz, 1H), 3.74 (dd, half of ABX pattern, J=11.5, 4.3 Hz, 1H), 2.71 (ddq, J=11.6, 9.1, 7.1 Hz, 1H), 2.39 (ddd, J=12.5, 9.2, 6.2 Hz, 1H), 1.86 (ddd, J=12.5, 11.7, 10.0 Hz, 1H), 1.30 (d, J=7.2 Hz, 3H), 1.07 (s, 9H).

Step 2. Synthesis of (3S,5S)-5-({[tert-butyl(diphenyl)silyl]oxy}methyl)-3-methyl-2-(4-(trifluoromethyl)phenyl)tetrahydrofuran-2-ol (C74)

Compound C73 was converted to the product using the method for synthesis of C25 in Example 6. The product, obtained as an orange oil, was taken directly to the following step.

Step 3. Synthesis of tert-butyl({(2S,4S,5R)-4-methyl-5-[4-(trifluoromethyl)phenyl]tetrahydrofuran-2-yl}methoxy)diphenylsilane (C75)

Compound C74 (≤1.51 mmol) was converted to the product, obtained as an oil, using the method described for synthesis of C26 in Example 6. Yield: 336 mg, 0.674 mmol, 45% over 2 steps. $^1$H NMR (400 MHz, CDCl$_3$) δ 7.73-7.78 (m, 4H), 7.53 (br d, J=8.2 Hz, 2H), 7.37-7.48 (m, 8H), 5.06 (d, J=7.4 Hz, 1H), 4.14-4.21 (m, 1H), 3.95 (dd, half of ABX pattern, J=10.9, 4.1 Hz, 1H), 3.86 (dd, half of ABX pattern, J=10.9, 4.7 Hz, 1H), 2.59-2.71 (m, 1H), 2.17 (ddd, J=12.4, 7, 7 Hz, 1H), 1.66 (ddd, J=12.4, 8.8, 7.5 Hz, 1H), 1.11 (s, 9H), 0.58 (d, J=7.0 Hz, 3H).

Step 4. Synthesis of {(2S,4S,5R)-4-methyl-5-[4-(trifluoromethyl)phenyl]tetrahydrofuran-2-yl}methanol (C76)

Deprotection of C75 was carried out using the method described for synthesis of C27 in Example 6. The product was obtained as an oil. The indicated stereochemistry for the aryl group was assigned on the basis of NOE experiments. Yield: 139 mg, 0.534 mmol, 81%. GCMS m/z 260 [M$^+$]. $^1$H NMR (400 MHz, CDCl$_3$) δ 7.60 (br d, J=8.2 Hz, 2H), 7.39-7.43 (m, 2H), 5.06 (d, J=7.0 Hz, 1H), 4.14-4.21 (m, 1H), 3.90 (dd, half of ABX pattern, J=11.7, 3.3 Hz, 1H), 3.77 (dd, half of ABX pattern, J=11.7, 6.2 Hz, 1H), 2.62-2.73 (m, 1H), 2.24 (ddd, J=12.5, 7.6, 7.0 Hz, 1H), 1.49 (ddd, J=12.5, 8.6, 6.6 Hz, 1H), 0.60 (d, J=7.0 Hz, 3H).

Step 5. Synthesis of {(2S,4S,5R)-4-methyl-5-[4-(trifluoromethyl)phenyl]tetrahydrofuran-2-yl}methyl methanesulfonate (C77)

Compound C76 was converted to the product using the method described for synthesis of C8 in Example 1; the product was obtained as an oil. Yield: 176 mg, 0.520 mmol, 100%. $^1$H NMR (400 MHz, CDCl$_3$) δ 7.61 (br d, J=8 Hz, 2H), 7.38-7.42 (m, 2H), 5.09 (d, J=7.2 Hz, 1H), 4.41-4.49 (m, 2H), 4.30-4.37 (m, 1H), 3.11 (s, 3H), 2.63-2.75 (m, 1H), 2.34 (ddd, J=12.7, 7.4, 7.4 Hz, 1H), 1.53 (ddd, J=12.7, 8.4, 6.6 Hz, 1H), 0.62 (d, J=7.0 Hz, 3H).

Step 6. Synthesis of 2-[({(2S,4S,5R)-4-methyl-5-[4-(trifluoromethyl)phenyl]tetrahydrofuran-2-yl}methyl)amino]ethanol (C78)

The product, obtained as an oil, was prepared from C77 using the method employed for synthesis of C29 in Example 6. Yield: 132 mg, 0.435 mmol, 86%. LCMS m/z 304.4 [M+H$^+$]. $^1$H NMR (400 MHz, CDCl$_3$) δ 7.59 (br d, J=8 Hz, 2H), 7.36-7.41 (m, 2H), 5.03 (d, J=7.4 Hz, 1H), 4.15-4.23 (m, 1H), 3.67-3.71 (m, 2H), 2.82-3.00 (m, 4H), 2.59-2.71 (m, 1H), 2.29 (ddd, J=12.3, 7.6, 6.8 Hz, 1H), 1.38 (ddd, J=12.5, 8.6, 7.0 Hz, 1H), 0.59 (d, J=7.0 Hz, 3H).

Step 7. Synthesis of 7-(4-methyl-1H-imidazol-1-yl)-2-({(2S,4S,5R)-4-methyl-5-[4-(trifluoromethyl)phenyl]tetrahydrofuran-2-yl}methyl)-3,4-dihydro-2H-pyrido[1,2-a]pyrazine-1,6-dione, trifluoroacetate salt (17)

Conversion of C78 to the product was carried out using the method described for synthesis of 6 in Example 6. After the chromatography on silica gel, the product was purified by reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 5% to 100% B), affording the product as a solid. Yield: 12 mg, 20 μmol, 4%. LCMS m/z 487.3 [M+H$^+$]. $^1$H NMR (600 MHz, DMSO-d$_6$) δ 9.37 (br s, 1H), 8.05 (br d, J=7.5 Hz, 1H), 7.81 (br s, 1H), 7.70 (br d, J=7.9 Hz, 2H), 7.52 (br d, J=7.9 Hz, 2H), 7.20 (d, J=7.5 Hz, 1H), 5.04 (d, J=7.0 Hz, 1H), 4.21-4.31 (m, 3H), 3.83-3.96 (m, 3H), 3.70 (dd, J=13.8, 8.1 Hz, 1H), 2.62-2.68 (m, 1H), 2.31 (s, 3H), 2.28-2.36 (m, 1H), 1.36-1.42 (m, 1H), 0.52 (d, J=7.0 Hz, 3H).

Example 18

2-({(2S,5R)-5-[3,5-Difluoro-4-(trifluoromethyl)phenyl]tetrahydrofuran-2-yl}methyl)-7-(4-methyl-1H-imidazol-1-yl)-3,4-dihydro-2H-pyrido[1,2-a]pyrazine-1,6-dione (18)

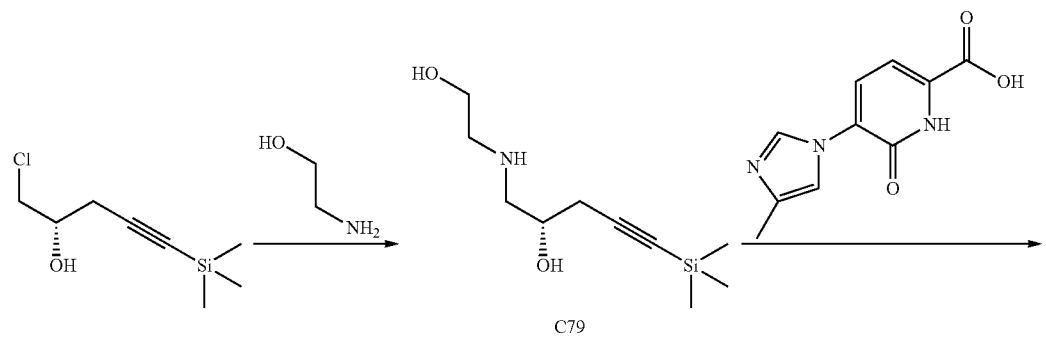

C79

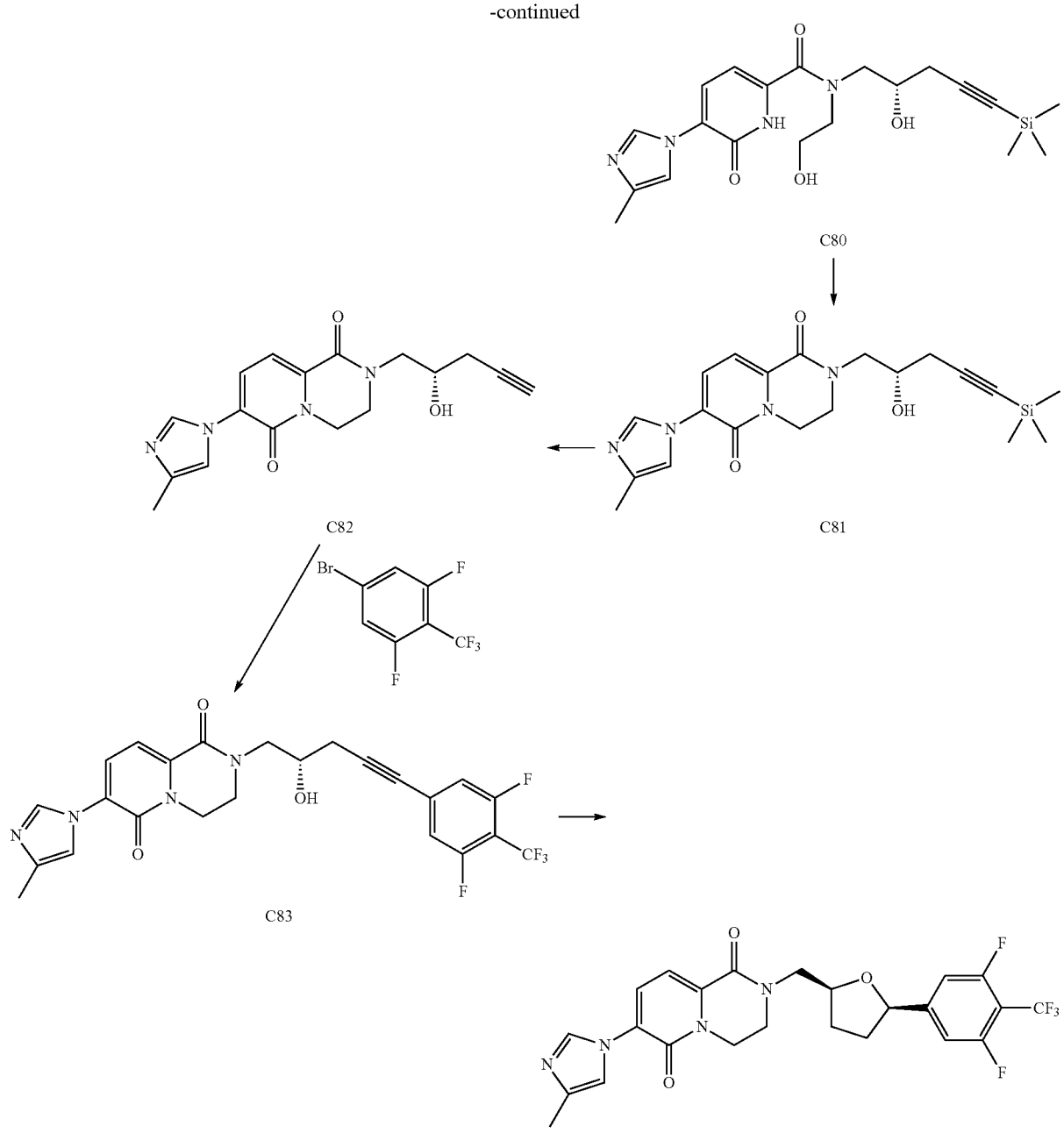

Step 1. Synthesis of (2S)-1-[(2-hydroxyethyl)amino]-5-(trimethylsilyl)pent-4-yn-2-ol (C79)

A mixture of (2S)-1-chloro-5-(trimethylsilyl)pent-4-yn-2-ol (80 g, 420 mmol) and 2-aminoethanol (110 g, 1.8 mol) was stirred at 80° C. for 18 hours. Silica gel chromatography (Gradient: 1% to 10% methanol in dichloromethane) provided the product as a yellow oil. Yield: 30 g, 140 mmol, 33%. $^1$H NMR (400 MHz, CD$_3$OD) δ 3.80-3.88 (m, 1H), 3.61-3.72 (m, 2H), 2.84 (dd, J=12.3, 3.3 Hz, 1H), 2.69-2.81 (m, 2H), 2.64 (dd, J=12.0, 8.5 Hz, 1H), 2.45 (dd, half of ABX pattern, J=16.6, 5.5 Hz, 1H), 2.37 (dd, half of ABX pattern, J=16.6, 7.0 Hz, 1H), 0.12 (s, 9H).

Step 2. Synthesis of N-(2-hydroxyethyl)-N-[(2S)-2-hydroxy-5-(trimethylsilyl)pent-4-yn-1-yl]-5-(4-methyl-1H-imidazol-1-yl)-6-oxo-1,6-dihydropyridine-2-carboxamide (C80)

Compound C79 was converted to the product using the general method described for preparation of 1 in Example 1. In this synthesis, slightly less than one equivalent of HATU was employed, the reaction was carried out in acetonitrile, and the extractions were done with ethyl acetate. The crude product solution was dried over sodium sulfate in this case, and the crude product was taken directly on to the following step.

Step 3. Synthesis of 2-[(2S)-2-hydroxy-5-(trimethylsilyl)pent-4-yn-1-yl]-7-(4-methyl-1H-imidazol-1-yl)-3,4-dihydro-2H-pyrido[1,2-a]pyrazine-1,6-dione (C81)

Diisopropyl azodicarboxylate (14 g, 69 mmol) was added drop-wise to a 0° C. mixture of crude C80 (60 mmol) and triphenylphosphine (18.9 g, 72.0 mmol) in tetrahydrofuran (500 mL). After being stirred at 0° C. for 2.5 hours, the reaction mixture was concentrated in vacuo; purification by silica gel chromatography (Gradient: 1% to 6% methanol in dichloromethane) afforded the product as a yellow solid. Yield: 7.0 g, 18 mmol, 30% over two steps.

Step 4. Synthesis of 2-[(2S)-2-hydroxypent-4-yn-1-yl]-7-(4-methyl-1H-imidazol-1-yl)-3,4-dihydro-2H-pyrido[1,2-a]pyrazine-1,6-dione (C82)

A mixture of C81 (6.5 g, 16 mmol) and potassium carbonate (2.25 g, 16.3 mmol) in methanol (150 mL) was stirred at room temperature for 5 hours. The reaction mixture was concentrated in vacuo and purified by silica gel chromatography (Gradient: 1% to 2.5% methanol in dichloromethane) to provide the product as a yellow solid. Yield: 2.5 g, 7.7 mmol, 48%. $^1$H NMR (400 MHz, CD$_3$OD) δ 8.31 (d, J=1.2 Hz, 1H), 7.78 (d, J=7.8 Hz, 1H), 7.31-7.33 (m, 1H), 7.25 (d, J=7.8 Hz, 1H), 4.33-4.39 (m, 2H), 4.04-4.12 (m, 1H), 3.82-3.96 (m, 3H), 3.50 (dd, J=13.7, 8.4 Hz, 1H), 2.41-2.46 (m, 2H), 2.37 (t, J=2.8 Hz, 1H), 2.24 (d, J=1.0 Hz, 3H).

Step 5. Synthesis of 2-{(2S)-5-[3,5-difluoro-4-(trifluoromethyl)phenyl]-2-hydroxypent-4-yn-1-yl}-7-(4-methyl-1H-imidazol-1-yl)-3,4-dihydro-2H-pyrido[1,2-a]pyrazine-1,6-dione (C83)

Compound C82 was reacted with 5-bromo-1,3-difluoro-2-(trifluoromethyl)benzene using the general procedure described for synthesis of C39 in Example 8. In this case, the reaction solvent was a 1.6:1 mixture of N,N-dimethylformamide and triethylamine, and the catalyst employed was dichlorobis(triphenylphosphine)palladium(II). Extraction was carried out with ethyl acetate, and the product, obtained as a light orange solid, was purified via silica gel chromatography (Gradient: 0% to 100% [10% (2 M ammonium in methanol) in ethyl acetate] in ethyl acetate). Yield: 505 mg, 0.997 mmol, 65%. $^1$H NMR (400 MHz, CDCl$_3$) δ 8.28 (d, J=1.2 Hz, 1H), 7.40 (d, J=7.8 Hz, 1H), 7.22 (d, J=7.6 Hz, 1H), 7.06-7.08 (m, 1H), 7.04 (d, J=9.8 Hz, 2H), 4.41 (ddd, half of ABXY pattern, J=14.3, 7.2, 4.2 Hz, 1H), 4.26-4.36 (m, 2H), 3.92-4.00 (m, 2H), 3.83 (ddd, half of ABXY pattern, J=13.5, 7.3, 4.2 Hz, 1H), 3.55 (dd, J=14.0, 8.3 Hz, 1H), 2.68-2.80 (m, 2H), 2.28 (br s, 3H).

Step 6. Synthesis of 2-({(2S,5R)-5-[3,5-difluoro-4-(trifluoromethyl)phenyl]tetrahydrofuran-2-yl}methyl)-7-(4-methyl-1H-imidazol-1-yl)-3,4-dihydro-2H-pyrido[1,2-a]pyrazine-1,6-dione (18)

Di-µ-chlorodichlorobis(ethylene)diplatinum(II) (97%, 60 mg, 99 µmol), trifluoroacetic acid (380 µL, 5.0 mmol) and water (89 µL, 5.0 mmol) were added to a solution of C83 (250 mg, 0.494 mmol) in dichloromethane (5 mL), and the reaction mixture was stirred at room temperature until analysis by thin layer chromatography indicated consumption of starting material. The reaction mixture was cooled to −20° C. and treated with trifluoroacetic acid (0.958 mL, 12.4 mmol) followed by drop-wise addition of triethylsilane (99%, 1.19 mL, 7.39 mmol) over 5 minutes. After slowly warming to room temperature, the reaction was allowed to proceed for 1.5 hours, whereupon dichloromethane (50 mL) was added, and the mixture was washed with water (25 mL) and with saturated aqueous sodium chloride solution (25 mL). The organic layer was dried over magnesium sulfate, filtered, and concentrated in vacuo; purification via silica gel chromatography (Gradient: 0% to 70% [10% (2 M ammonium in methanol) in ethyl acetate] in ethyl acetate) was followed by HPLC (Column: Phenomenex Lux Cellulose-1, 5 µm; Gradient: 70% to 100% ethanol in heptane) to provide the product as a solid. Yield: 40 mg, 79 µmol, 16%. LCMS m/z 509.0 [M+H$^+$]. $^1$H NMR (400 MHz, CDCl$_3$) δ 8.35 (br s, 1H), 7.49 (d, J=7.6 Hz, 1H), 7.29 (d, J=7.6 Hz, 1H), 7.16 (br s, 1H), 6.98 (d, J=10.4 Hz, 2H), 4.86-4.92 (m, 1H), 4.31-4.41 (m, 3H), 4.14 (dd, J=13.9, 2.7 Hz, 1H), 3.92-4.01 (m, 1H), 3.78-3.86 (m, 1H), 3.47 (dd, J=14.0, 8.5 Hz, 1H), 2.37-2.48 (m, 1H), 2.31 (s, 3H), 2.16-2.26 (m, 1H), 1.69-1.87 (m, 2H).

Method A

Preparation of 2-substituted 7-(4-methyl-1H-imidazol-1-yl)-3,4-dihydro-2H-pyrido[1,2-a]pyrazine-1,6-diones M1 via initial reductive amination

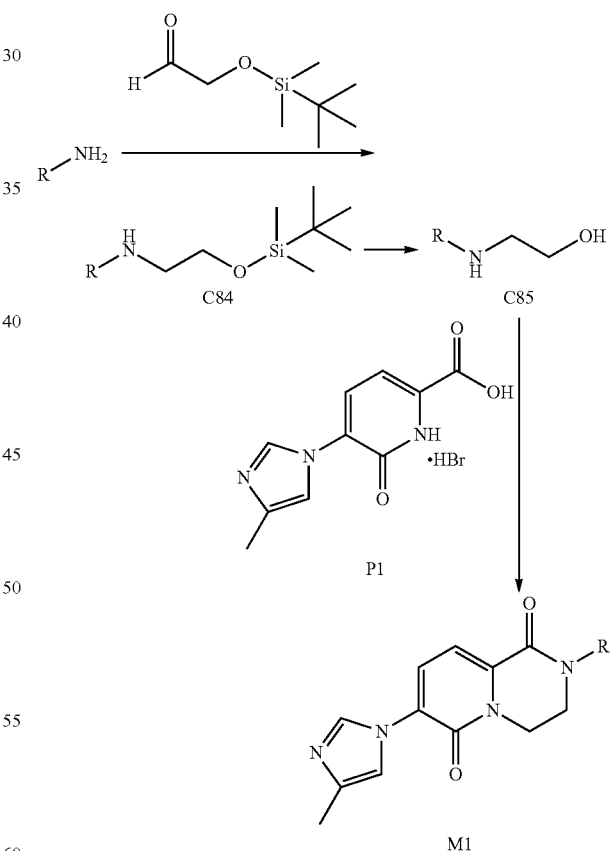

Step 1. Synthesis of N-substituted 2-{[tert-butyl(dimethyl)silyl]oxy}ethanamine C84

A solution of the primary amine (300 µmol) in methanol (1 mL) was treated with {[tert-butyl(dimethyl)silyl]

oxy}acetaldehyde (28 μL, 150 μmol) and shaken at 30° C. for 40 minutes. The reaction vial was cooled to 0° C., sodium borohydride (17 mg, 450 μmol) was added, and the reaction was shaken at 30° C. for 100 minutes. The solvent was removed in vacuo, water (1 mL) was added and the mixture was extracted with ethyl acetate (3×1 mL). The combined organic layers were dried over sodium sulfate, filtered, concentrated in vacuo, and purified via preparative thin layer chromatography.

Step 2. Synthesis of N-substituted 2-aminoethanol C85

A solution of C84 in methanol (500 μL) was treated with a solution of acetyl chloride (188 μL) in methanol (312 μL) at 30° C. for 16 hours. The solvent was removed in vacuo.

Step 3. Synthesis of 2-substituted 7-(4-methyl-1H-imidazol-1-yl)-3,4-dihydro-2H-pyrido[1,2-a]pyrazine-1,6-dione M1

Compound C85 was treated with P1 (34.4 mg, 125 μmol), dichloromethane (2 mL), diisopropylethylamine (217 μL, 1.25 mmol) and O-(7-azabenzotriazol-1-yl)-N,N,N',N'-tetramethyluronium hexafluorophosphate (HATU, 97%, 122 mg, 320 μmol), then shaken at 30° C. for 16 hours. The solvent was removed in vacuo and the residue was treated with saturated aqueous sodium bicarbonate solution (2 mL) and extracted with ethyl acetate (3×1 mL). The combined organic layers were dried over sodium sulfate, filtered, concentrated in vacuo, and purified via reversed phase HPLC. Purifications were carried out using a Phenomenex Gemini C18 column (8-10 μm), with the non-aqueous mobile phase consisting of ammonium hydroxide in acetonitrile (pH 10) and employing an appropriate gradient.

TABLE 1

| Ex. # | R = | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 19 | 3-(3,4-difluorophenyl)-4,5-dihydroisoxazol-4-yl | Example 1[1] | 2.20 minutes[2]; 426.2 |
| 20 | (±)-trans-3-[3-(trifluoromethyl)phenoxy]cyclopentyl | Example 1[3] | characteristic peaks: 2.33 (br s, 3H), 3.65 (br dd, J = 6, 6 Hz, 2H), 4.31-4.43 (m, 2H), 4.93-4.98 (m, 1H), 5.17-5.27 (m, 1H), 7.05 (br dd, J = 8, 2 Hz, 1H), 7.08-7.11 (m, 1H), 7.18-7.23 (m, 2H), 7.30 (d, J = 7.8 Hz, 1H), 7.40 (br dd, J = 8, 8 Hz, 1H), 7.56 (d, J = 7.8 Hz, 1H), 8.43 (br s, 1H); 473.3 |

TABLE 1-continued

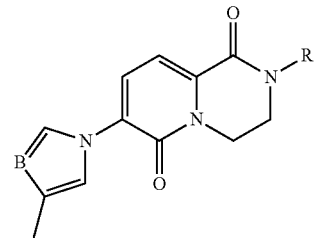

| Ex. # | R = 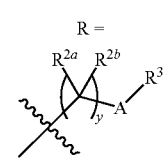 | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 21 | 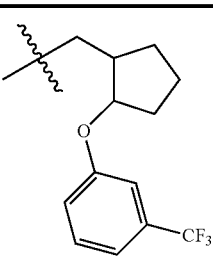 | Example 1[4] | 1.37-1.48 (m, 1H), 1.71-1.89 (m, 3H), 1.97-2.07 (m, 1H), 2.12-2.22 (m, 1H), 2.29 (s, 3H), 2.50-2.61 (m, 1H), 3.43 (dd, J = 13.7, 6.4 Hz, 1H), 3.65 (ddd, J = 13.3, 6.6, 4.1 Hz, 1H), 3.80 (ddd, J = 13.3, 8.4, 3.9 Hz, 1H), 4.00 (dd, J = 13.7, 9.6 Hz, 1H), 4.21 (ddd, J = 14.2, 8.5, 4.1 Hz, 1H), 4.44 (ddd, J = 14.2, 6.5, 4.0 Hz, 1H), 4.60-4.65 (m, 1H), 6.93-6.98 (m, 2H), 7.03 (d, J = 7.7 Hz, 1H), 7.11 (br s, 1H), 7.15 (br d, J = 7.7 Hz, 1H), 7.32 (br dd, J = 8.1, 7.7 Hz, 1H), 7.34 (d, J = 7.7 Hz, 1H), 8.21 (br s, 1H); 487.3 |
| 22 | 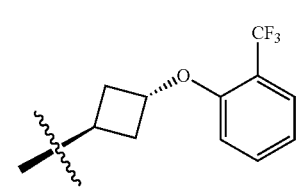 | Example 1[5] | 2.55 minutes[2]; 459.2 |
| 23 | 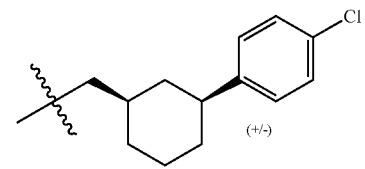 | Example 1; P5 | 1.03-1.49 (m, 4H), 1.75-2.00 (m, 5H), 2.27 (d, J = 0.8 Hz, 3H), 2.47-2.56 (m, 1H), 3.44-3.48 (m, 2H), 3.68 (dd, J = 5.8, 5.7 Hz, 2H), 4.28-4.40 (m, 2H), 7.09-7.13 (m, 3H), 7.22-7.26 (m, 3H), 7.43 (d, J = 7.6 Hz, 1H), 8.21 (d, J = 1.2 Hz, 1H); 451.1 |
| 24 | 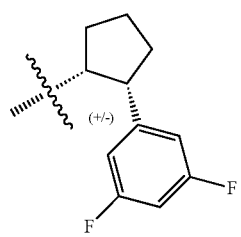 | Method A[6] | 2.72 minutes[7]; 425 |
| 25 | 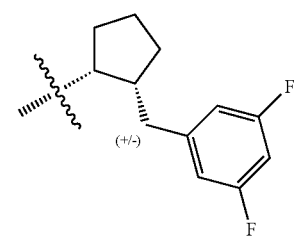 | Method A[9] | 2.85 minutes[7]; 439 |

TABLE 1-continued

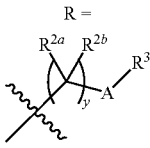

| Ex. # | R = 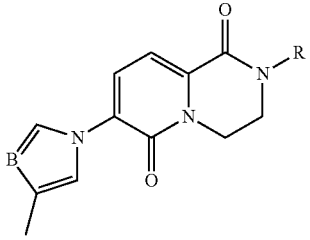 | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 26 | 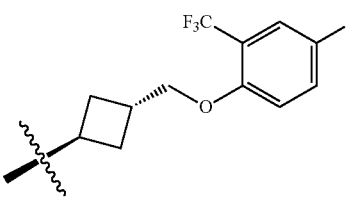 | Example 1[10] | 2.65 minutes[2]; 491.1 |
| 27 | 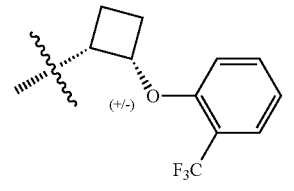 | Example 1; P4 | 2.44 minutes[2]; 459.2 |
| 28 | 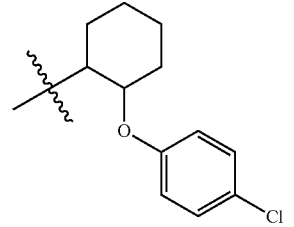 [SMILES: *C1CCCCC1Oc1ccc(Cl)cc1] | Example 1[12] | 2.26 minutes[2]; 453.0, 455.0 |
| 29 | 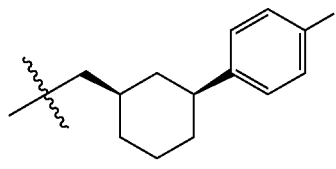 | Example 1; P5[13] | 1.04-1.28 (m, 2H), 1.31-1.50 (m, 2H), 1.76-2.01 (m, 5H), 2.29 (br s, 3H), 2.48-2.58 (m, 1H), 3.45-3.49 (m, 2H), 3.67-3.72 (m, 2H), 4.29-4.42 (m, 2H), 7.11-7.15 (m, 1H), 7.12 (d, J = 8.4 Hz, 2H), 7.25 (d, J = 8.4 Hz, 2H), 7.24-7.28 (m, 1H, assumed; obscured by solvent peak), 7.44 (d, J = 7.4 Hz, 1H), 8.22 (br s, 1H); 451 |
| 30 | 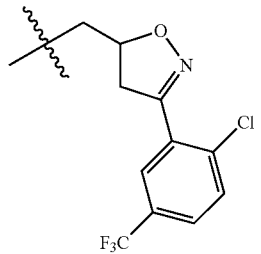 [SMILES: *CC1CC(c2cc(C(F)(F)F)ccc2Cl)=NO1] | Example 4 | 2.49 minutes[2]; 506.3, 508.3 |

TABLE 1-continued
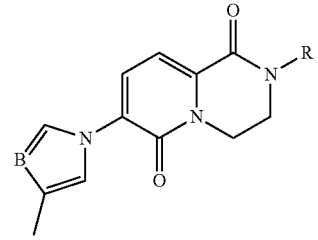
| Ex. # | R = 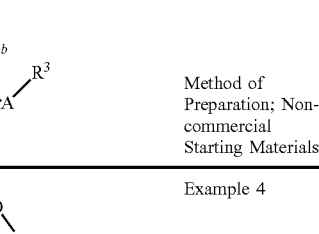 | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 31 | 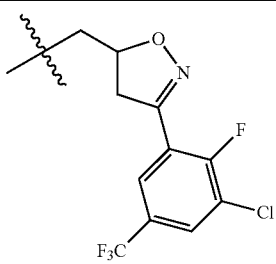 | Example 4 | 2.60 minutes[2]; 524.3, 526.3 |
| 32 | 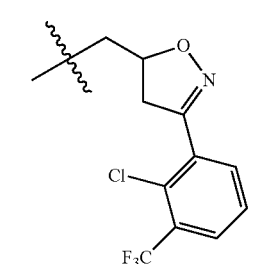 | Example 4 | 2.46 minutes[2]; 506.3, 508.3 |
| 33 | 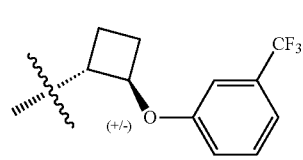 | Example 3 | 2.58 minutes[2]; 459.3 |
| 34 | 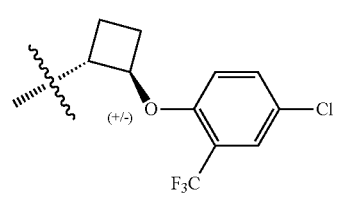 | Example 3 | 2.60 minutes[2]; 493.0, 493.5 |
| 35 | 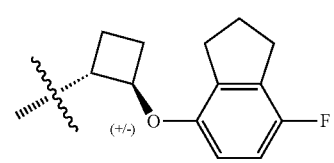 | Example 3 | 2.48 minutes[2]; 449.0 |
| 36 | 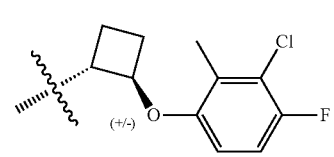 | Example 3[14] | 2.61 minutes[2]; 457.0, 459.0 |

TABLE 1-continued
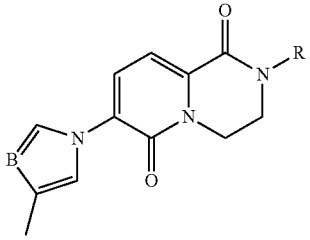
| Ex. # | R = 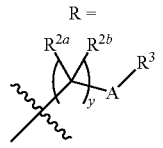 | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 37 | 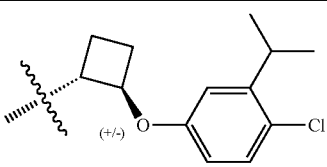 | Example 3[15] | 2.85 minutes[2]; 467.1, 469.0 |
| 38 | 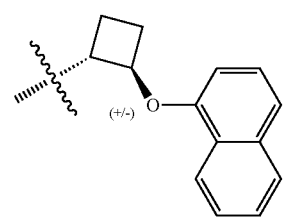 | Example 3 | 2.57 minutes[2]; 441.1 |
| 39 | 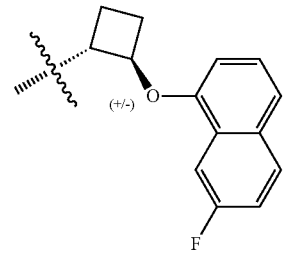 | Example 3[16] | 2.62 minutes[2]; 459.1 |
| 40 | 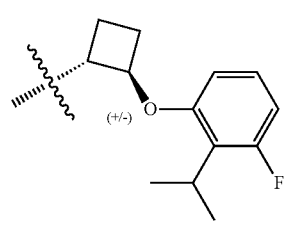 | Example 3[17] | 2.69 minutes[2]; 451.2 |
| 41 | 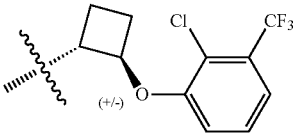 | Example 3 | 2.65 minutes[2]; 493.0, 495.0 |
| 42 | 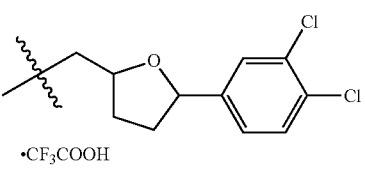 [SMILES: "·CF3COOH" ; *CC1CCC(c2ccc(Cl)c(Cl)c2)O1] ·CF$_3$COOH | Example 1[18] | 2.63 minutes[2]; 473.1, 475.1 |

TABLE 1-continued

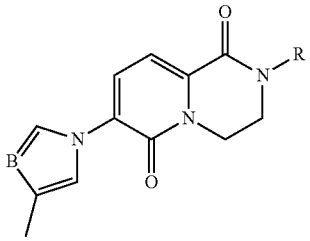

| Ex. # | R = 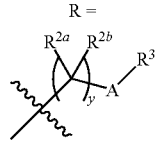 | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 43 | 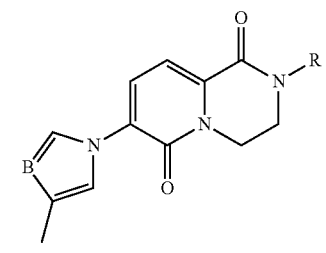 | Example 7 | 8.29 (d, J = 1.2 Hz, 1H), 7.62 (br d, J = 8.2 Hz, 2H), 7.47 (d, J = 7.8 Hz, 1H), 7.42-7.46 (m, 2H), 7.29 (d, J = 7.8 Hz, 1H), 7.14-7.16 (m, 1H), 4.92-4.97 (m, 1H), 4.28-4.43 (m, 3H), 4.19 (dd, J = 14.0, 3.0 Hz, 1H), 4.00 (ddd, half of ABXY pattern, J = 13.5, 7.6, 4.3 Hz, 1H), 3.82 (ddd, half of ABXY pattern, J = 13.5, 7.2, 4.1 Hz, 1H), 3.44 (dd, J = 14.0, 8.2 Hz, 1H), 2.37-2.46 (m, 1H), 2.31 (d, J = 1.0 Hz, 3H), 2.16-2.26 (m, 1H), 1.73-1.89 (m, 2H); 473.2 |
| 44 | 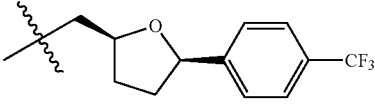 [SMILES: *C[C@@H]1CC[C@H](c2ccc(C(F)(F)F)cc2)O1] | Example 7[19,20] | 8.51 (br s, 1H), 7.55 (d, J = 7.6 Hz, 1H), 7.33 (br d, half of AB quartet, J = 8.4 Hz, 2H), 7.29 (d, J = 7.8 Hz, 1H), 7.24-7.28 (m, 2H, assumed; partially obscured by solvent peak), 7.17-7.20 (m, 1H), 4.86 (dd, J = 7.4, 6.8 Hz, 1H), 4.26-4.42 (m, 3H), 4.17 (dd, J = 14.0, 2.9 Hz, 1H), 3.98 (ddd, half of ABXY pattern, J = 13.5, 7.5, 4.2 Hz, 1H), 3.81 (ddd, half of ABXY pattern, J = 13.5, 7.3, 4.2 Hz, 1H), 3.42 (dd, J = 14.0, 8.2 Hz, 1H), 2.35 (d, J = 0.8 Hz, 3H), 2.31-2.40 (m, 1H), 2.14-2.23 (m, 1H), 1.72-1.87 (m, 2H); 439.1 |
| 45 | 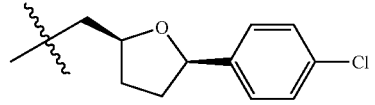 [SMILES: *C[C@@H]1CC[C@H](c2ccc(Cl)cc2)O1] | Example 7[21,22] | 8.22 (d, J = 1.2 Hz, 1H), 7.75 (br d, J = 8.8 Hz, 2H), 7.45 (d, J = 7.6 Hz, 1H), 7.42 (br d, J = 8.2 Hz, 2H), 7.28 (d, J = 7.8 Hz, 1H), 7.13-7.15 (m, 1H), 4.91-4.96 (m, 1H), 4.29-4.43 (m, 3H), 4.18 (dd, J = 14.1, 2.9 Hz, 1H), 3.99 (ddd, half of ABXY pattern, J = 13.5, 7.3, 4.5 Hz, 1H), 3.82 (ddd, half of ABXY pattern, J = 13.4, 7.1, 4.4 Hz, 1H), 3.45 (dd, J = 14.0, 8.5 Hz, 1H), 2.38-2.47 (m, 1H), 2.29 (br s, 3H), 2.16-2.25 (m, 1H), 1.72-1.88 (m, 2H); 531.2 |
| 46 | 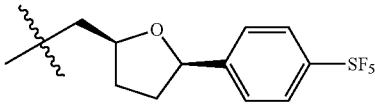 | Example 6[23,24] | 8.22 (d, J = 1.2 Hz, 1H), 7.45 (d, J = 7.8 Hz, 1H), 7.33-7.38 (m, 2H), 7.27-7.30 (m, 1H, assumed; partially obscured by solvent peak), 7.19-7.24 (m, 2H), 7.13-7.15 (m, 1H), 4.87-4.92 (m, 1H), 4.27-4.43 (m, 3H), 4.18 (dd, J = 13.9, 2.9 Hz, 1H), 3.94-4.02 (m, 1H), 3.77-3.84 (m, 1H), 3.43 (dd, J = 13.9, 8.2 Hz, 1H), 2.34-2.42 (m, 1H), 2.28-2.31 (m, 3H), 2.15-2.24 (m, 1H), 1.73-1.89 (m, 2H); 489.2 |

TABLE 1-continued

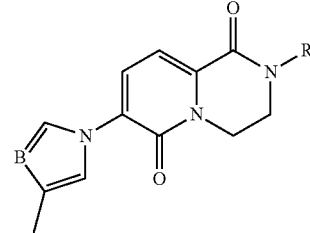

| Ex. # | R = 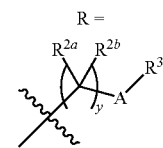 | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 47 | 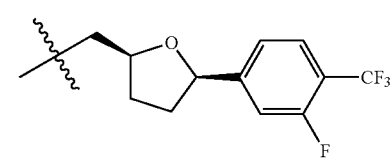 [SMILES: *C[C@@H]1CC[C@H](c2ccc(C(F)(F)F)c(F)c2)O1] | Example 7 | 9.45 (d, J = 1.6 Hz, 1H), 7.89 (d, J = 7.8 Hz, 1H), 7.59 (dd, J = 7.6, 7.6 Hz, 1H), 7.38 (d, J = 7.6 Hz, 1H), 7.32-7.36 (m, 1H), 7.16-7.21 (m, 2H), 4.90-4.96 (m, 1H), 4.32-4.42 (m, 3H), 4.15-4.21 (m, 1H), 3.98-4.06 (m, 1H), 3.82-3.90 (m, 1H), 3.47 (dd, J = 14.1, 8.6 Hz, 1H), 2.55 (d, J = 1.0 Hz, 3H), 2.38-2.48 (m, 1H), 2.18-2.27 (m, 1H), 1.71-1.89 (m, 2H); 491.0 |
| 48 | 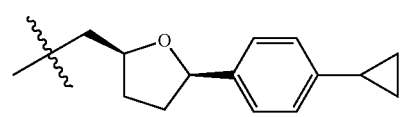 [SMILES: *C[C@@H]1CC[C@H](c2ccc(C3CC3)cc2)O1] | Example 7 | 8.22 (br s, 1H), 7.45 (d, J = 7.6 Hz, 1H), 7.27 (d, J = 7.8 Hz, 1H), 7.21 (br d, J = 8.2 Hz, 2H), 7.12-7.15 (m, 1H), 7.06 (br d, J = 8.0 Hz, 2H), 4.82-4.88 (m, 1H), 4.21-4.41 (m, 3H), 4.16 (dd, J = 14.0, 2.6 Hz, 1H), 3.93-4.02 (m, 1H), 3.76-3.84 (m, 1H), 3.41 (dd, J = 14, 8 Hz, 1H), 2.29 (br s, 3H), 2.26-2.37 (m, 1H), 2.12-2.22 (m, 1H), 1.73-1.94 (m, 3H), 0.94-1.00 (m, 2H), 0.67-0.72 (m, 2H); 7.45 minutes$^{25}$ |
| 49 | 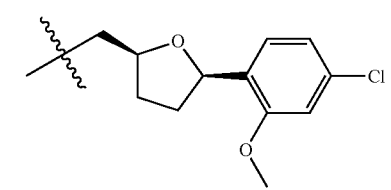 [SMILES: *C[C@@H]1CC[C@H](c2ccc(Cl)cc2OC)O1] | Example 7$^{26}$ | 8.21 (br s, 1H), 7.44 (d, J = 7.8 Hz, 1H), 7.31 (br d, J = 8.2 Hz, 1H), 7.26 (d, J = 7.6 Hz, 1H), 7.11-7.15 (m, 1H), 6.94 (dd, J = 8.1, 1.9 Hz, 1H), 6.84 (d, J = 1.8 Hz, 1H), 5.05-5.10 (m, 1H), 4.23-4.42 (m, 3H), 4.18 (dd, J = 13.9, 2.9 Hz, 1H), 4.00 (ddd, J = 13.5, 7.5, 4.4 Hz, 1H), 3.81 (s, 3H), 3.78-3.87 (m, 1H), 3.40-3.51 (m, 1H), 2.34-2.45 (m, 1H), 2.28 (br s, 3H), 2.08-2.18 (m, 1H), 1.61-1.73 (m, 2H); 469.2 |
| 50 | 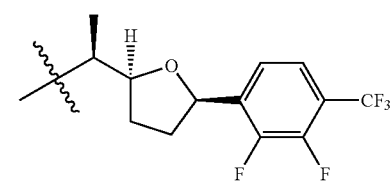 [SMILES: *[C@@H](C)[C@@H]1CC[C@H](c2ccc(C(F)(F)F)c(F)c2F)O1] | Example 8 | 8.23 (br s, 1H), 7.46 (d, J = 7.6 Hz, 1H), 7.33-7.41 (m, 2H), 7.29 (d, J = 7.6 Hz, 1H), 7.11-7.14 (m, 1H), 5.12-5.19 (m, 1H), 4.83-4.93 (m, 1H), 4.35-4.44 (m, 1H), 4.26-4.35 (m, 1H), 4.05-4.13 (m, 1H), 3.71-3.79 (m, 1H), 3.62-3.71 (m, 1H), 2.45-2.57 (m, 1H), 2.28 (s, 3H), 2.15-2.25 (m, 1H), 1.84-1.95 (m, 1H), 1.71-1.82 (m, 1H), 1.30 (d, J = 6.9 Hz, 3H); 523.3 |

TABLE 1-continued

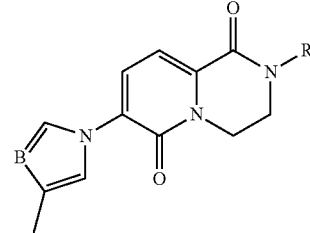

| Ex. # | R = 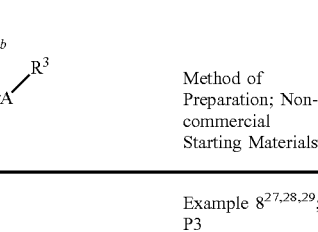 | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 51 | 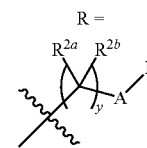 | Example 8[27,28,29]; P3 | 8.25 (br s, 1H), 7.55 (br dd, J = 8, 7 Hz, 1H), 7.47 (d, J = 7.7 Hz, 1H), 7.32 (d, J = 7.7 Hz, 1H), 7.12-7.21 (m, 3H), 4.81-4.93 (m, 2H), 4.44 (ddd, J = 14.1, 6.9, 4.0 Hz, 1H), 4.24 (ddd, J = 14.1, 8.1, 4.0 Hz, 1H), 4.08-4.15 (m, 1H), 3.76 (ddd, half of ABXY pattern, J = 13.4, 8.2, 3.9 Hz, 1H), 3.67 (ddd, half of ABXY pattern, J = 13.4, 6.9, 4.1 Hz, 1H), 2.38-2.46 (m, 1H), 2.30 (d, J = 0.9 Hz, 3H), 2.16-2.25 (m, 1H), 1.77-1.91 (m, 2H), 1.32 (d, J = 6.9 Hz, 3H); 505.0 |
| 52 | 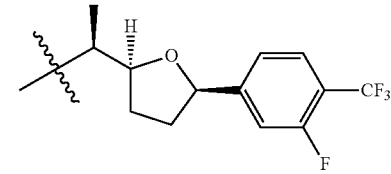 [SMILES: *[C@@H](C)[C@@H]1CC[C@H](c2ccc(C(F)(F)F)c(F)c2)O1] | Example 9[29] | 8.42 (br s, 1H), 7.53 (br d, J = 7.9 Hz, 1H), 7.51 (d, J = 7.7 Hz, 1H), 7.33 (d, J = 7.7 Hz, 1H), 7.23 (br d, J = 8 Hz, 1H), 7.14-7.16 (m, 1H), 7.02 (br s, 1H), 5.12-5.17 (m, 1H), 4.85-4.93 (m, 1H), 4.40 (ddd, half of ABXY pattern, J = 14, 7, 4 Hz, 1H), 4.31 (ddd, half of ABXY pattern, J = 14, 7.5, 4 Hz, 1H), 4.03-4.10 (m, 1H), 3.86 (s, 3H), 3.82 (ddd, J = 13, 7.5, 4 Hz, 1H), 3.69 (ddd, J = 13, 7, 4 Hz, 1H), 2.43-2.53 (m, 1H), 2.34 (d, J = 0.8 Hz, 3H), 2.10-2.19 (m, 1H), 1.67-1.79 (m, 2H), 1.33 (d, J = 6.9 Hz, 3H); 517.3 |
| 53 | 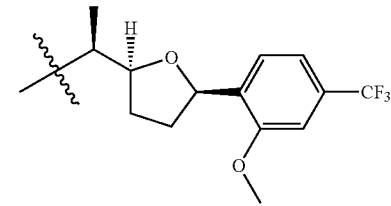 [SMILES: *[C@@H](C)[C@@H]1CC[C@H](c2ccc(C(F)(F)F)cc2OC)O1] | Example 9[30,29] | 8.31 (br s, 1H), 7.71 (br d, J = 8 Hz, 1H), 7.52-7.59 (m, 2H), 7.49 (d, J = 7.7 Hz, 1H), 7.33 (d, J = 7.7 Hz, 1H), 7.13-7.15 (m, 1H), 5.20-5.25 (m, 1H), 4.94 (dq, J = 9.0, 6.9 Hz, 1H), 4.44 (ddd, half of ABXY pattern, J = 14.2, 7.2, 4.0 Hz, 1H), 4.31 (ddd, half of ABXY pattern, J = 14.1, 7.7, 4.1 Hz, 1H), 4.06-4.14 (m, 1H), 3.77 (ddd, half of ABXY pattern, J = 13.3, 7.7, 4.0 Hz, 1H), 3.69 (ddd, half of ABXY pattern, J = 13.4, 7.2, 4.1 Hz, 1H), 2.56-2.65 (m, 1H), 2.31 (d, J = 1.0 Hz, 3H), 2.15-2.24 (m, 1H), 1.69-1.87 (m, 2H), 1.32 (d, J = 6.9 Hz, 3H); 521.2 |

TABLE 1-continued

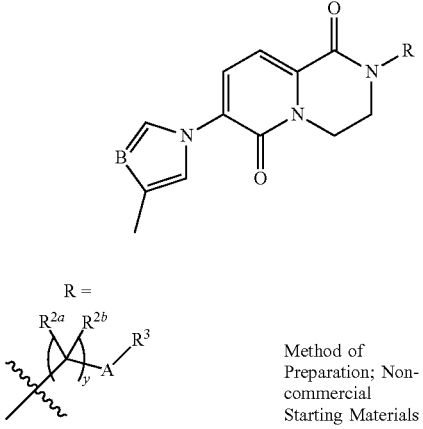

| Ex. # | R = 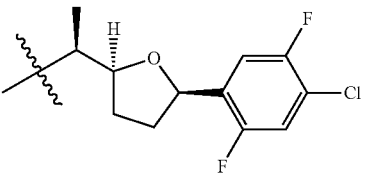 [SMILES: *[C@@H](C)[C@@H]1CC[C@H](c2cc(F)c(Cl)cc2F)O1] | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 54 | 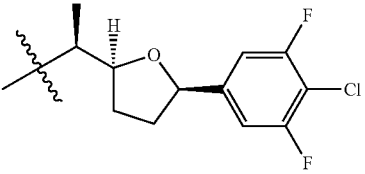 | Example 10[31,32] | 8.23 (br s, 1H), 7.47 (d, J = 7.4 Hz, 1H), 7.34 (d, J = 7.4 Hz, 1H), 7.27-7.33 (m, 1H, assumed; partially obscured by solvent peak), 7.13-7.15 (m, 1H), 7.07 (dd, J = 9.2, 6.0 Hz, 1H), 5.01-5.06 (m, 1H), 4.82-4.91 (m, 1H), 4.49 (ddd, J = 14.0, 6.2, 4.3 Hz, 1H), 4.23 (ddd, J = 14, 8, 4 Hz, 1H), 4.03-4.10 (m, 1H), 3.63-3.79 (m, 2H), 2.40-2.49 (m, 1H), 2.29 (s, 3H), 2.15-2.24 (m, 1H), 1.75-1.88 (m, 2H), 1.32 (d, J = 7.0 Hz, 3H); 489.2 |
| 55 | 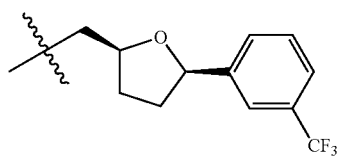 [SMILES: *C[C@@H]1CC[C@H](c2cccc(C(F)(F)F)c2)O1] | Example 10[31,32] | 8.26 (br s, 1H), 7.48 (d, J = 7.8 Hz, 1H), 7.33 (d J = 7.6 Hz, 1H), 7.12-7.15 (m, 1H), 6.96 (br d, J = 7.8 Hz, 2H), 4.78-4.88 (m, 2H), 4.48 (ddd, J = 14.2, 6.4, 4.0 Hz, 1H), 4.20 (ddd, J = 14.1, 8.4, 4.1 Hz, 1H), 4.05-4.12 (m, 1H), 3.62-3.77 (m, 2H), 2.33-2.42 (m, 1H), 2.30 (s, 3H), 2.15-2.26 (m, 1H), 1.76-1.88 (m, 2H), 1.31 (d, J = 6.8 Hz, 3H); 489.2 |
| 56 | 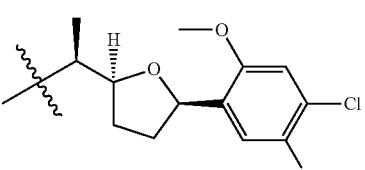 | Example 6[33,34] | 8.24 (br s, 1H), 7.46-7.60 (m, 4H), 7.46 (d, J = 7.6 Hz, 1H), 7.28 (d, J = 7.8 Hz, 1H), 7.13-7.16 (m, 1H), 4.91-4.97 (m, 1H), 4.26-4.42 (m, 3H), 4.17 (dd, J = 14.0, 2.9 Hz, 1H), 3.98 (ddd, J = 13.5, 7.6, 4.3 Hz, 1H), 3.82 (ddd, J = 13.5, 7.3, 4.2 Hz, 1H), 3.46 (dd, J = 14.0, 8.1 Hz, 1H), 2.37-2.46 (m, 1H), 2.29 (d, J = 0.8 Hz, 3H), 2.17-2.25 (m, 1H), 1.74-1.90 (m, 2H); 473.2 |
| 57 |  | Example 8[32,29,35] | 8.35 (br s, 1H), 7.50 (d, J = 7.8 Hz, 1H), 7.36 (d, J = 7.4 Hz, 1H), 7.23 (d, J = 9.8 Hz, 1H), 7.12-7.18 (m, 1H), 6.80 (d, J = 5.8 Hz, 1H), 5.00-5.06 (m, 1H), 4.81-4.90 (m, 1H), 4.50 (ddd, J = 14.1, 6.6, 3.9 Hz, 1H), 4.21 (ddd, J = 14.1, 8.6, 3.9 Hz, 1H), 3.99-4.07 (m, 1H), 3.78 (s, 3H), 3.73-3.82 (m, 1H), 3.68 (ddd, half of ABXY pattern, J = 13.3, 6.6, 3.9 Hz, 1H), 2.38-2.47 (m, 1H), 2.32 (br s, 3H), 2.12-2.21 (m, 1H), 1.63-1.80 (m, 2H), 1.31 (d, J = 7.0 Hz, 3H); 501.2 |

TABLE 1-continued

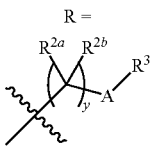

| Ex. # | R = 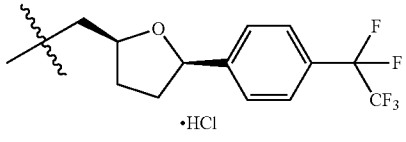 [SMILES: *C[C@@H]1CC[C@H](c2ccc(C(F)(F)C(F)(F)F)cc2)O1 ; Cl] | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 58 | 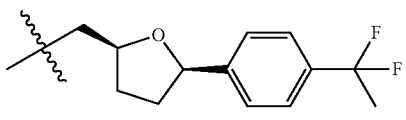 | Example 8[32,29,36] | 8.34 (br s, 1H), 7.47-7.53 (m, 2H), 7.31 (d, J = 7.8 Hz, 1H), 7.25-7.29 (m, 1H, assumed; partially obscured by solvent peak), 7.20-7.23 (m, 1H), 7.13-7.16 (m, 1H), 5.09 (br dd, J = 7.4, 7.0 Hz, 1H), 4.83-4.92 (m, 1H), 4.40 (ddd, half of ABXY pattern, J = 14.1, 7.0, 3.9 Hz, 1H), 4.29 (ddd, half of ABXY pattern, J = 14.1, 7.8, 4.3 Hz, 1H), 4.02-4.10 (m, 1H), 3.76 (ddd, half of ABXY pattern, J = 13.5, 7.4, 3.7 Hz, 1H), 3.67 (ddd, half of ABXY pattern, J = 13.5, 7.2, 3.9 Hz, 1H), 2.39-2.49 (m, 1H), 2.32 (s, 3H), 2.15-2.26 (m, 1H), 1.72-1.83 (m, 2H), 1.31 (d, J = 7.0 Hz, 3H); 537.2 |
| 59 | ·HCl | Example 13[37] | 9.49 (d, J = 1.5 Hz, 1H), 8.06 (d, J = 7.8 Hz, 1H), 7.76 (br s, 1H), 7.63 (s, 4H), 7.33 (br d, J = 7.8 Hz, 1H), 5.01 (br dd, J = 7, 7 Hz, 1H), 4.30-4.47 (m, 3H), 3.89-4.04 (m, 3H), 3.75 (dd, J = 13.9, 8.4 Hz, 1H), 2.40-2.50 (m, 1H), 2.44 (s, 3H), 2.18-2.28 (m, 1H), 1.78-1.90 (m, 2H); 523.3 |
| 60 | | Example 7[38,39] | characteristic peaks: 8.23 (d, J = 1.2 Hz, 1H), 7.50 (br d, J = 8.4 Hz, 2H), 7.45 (d, J = 7.8 Hz, 1H), 7.38 (br d, J = 8.3 Hz, 2H), 7.27 (d, J = 7.8 Hz, 1H), 7.12-7.15 (m, 1H), 4.88-4.94 (m, 1H), 4.25-4.42 (m, 3H), 4.18 (dd, J = 13.9, 2.9 Hz, 1H), 3.99 (ddd, J = 13.5, 7.7, 4.2 Hz, 1H), 3.81 (ddd, J = 13.5, 7.2, 4.2 Hz, 1H), 3.43 (dd, J = 14.0, 8.1 Hz, 1H), 2.34-2.45 (m, 1H), 2.29 (s, 3H), 2.14-2.25 (m, 1H), 1.93 (t, J = 18.2 Hz, 3H); 469.3 |

TABLE 1-continued

| Ex. # | R = | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 61 | | Example 9[40,41,29] | $^1$H NMR (600 MHz, DMSO-d$_6$), d 8.24 (br s, 1H), 7.80 (d, J = 7.4 Hz, 1H), 7.52 (d, J = 2.6 Hz, 1H), 7.38-7.40 (m, 1H), 7.36 (dd, J = 8.8, 2.6 Hz, 1H), 7.19 (t, J = 73.7 Hz, 1H), 7.17 (d, J = 8.8 Hz, 1H), 7.16 (d, J = 7.9 Hz, 1H), 5.00 (dd, J = 7.4, 7.0 Hz, 1H), 4.67-4.73 (m, 1H), 4.34 (ddd, J = 14.0, 6.1, 4.0 Hz, 1H), 4.06-4.14 (m, 2H), 3.77 (ddd, J = 13.6, 6.1, 4.0 Hz, 1H), 3.64 (ddd, J = 13.6, 8.8, 3.5 Hz, 1H), 2.33-2.40 (m, 1H), 2.15 (s, 3H), 2.10-2.17 (m, 1H), 1.73-1.79 (m, 1H), 1.62-1.70 (m, 1H), 1.23 (d, J = 7.0 Hz, 3H); 519.0, 521.0 |
| 62 | | Example 18[42] | 8.26 (br s, 1H), 7.46 (d, J = 7.8 Hz, 1H), 7.28 (d, J = 7.8 Hz, 1H), 7.15 (br s, 1H), 6.96 (d, J = 7.4 Hz, 2H), 4.82-4.87 (m, 1H), 4.29-4.40 (m, 3H), 4.15 (dd, J = 14.0, 2.7 Hz, 1H), 3.93-4.01 (m, 1H), 3.77-3.85 (m, 1H), 3.44 (dd, J = 13.8, 8.4 Hz, 1H), 2.34-2.43 (m, 1H), 2.30 (s, 3H), 2.14-2.24 (m, 1H), 1.70-1.85 (m, 2H); 475.2 |
| 63 | ·CF$_3$COOH | Example 7[43] | $^1$H NMR (600 MHz, DMSO-d$_6$), δ 9.29 (br s, 1H), 8.02 (d, J = 7.5 Hz, 1H), 7.87 (d, J = 7.5 Hz, 1H), 7.77 (br s, 1H), 7.66-7.75 (m, 2H), 7.50 (dd, J = 7.9, 7.5 Hz, 1H), 7.19 (d, J = 7.9 Hz, 1H), 5.11 (br dd, J = 7, 7 Hz, 1H), 4.24-4.32 (m, 3H), 3.82-3.90 (m, 3H), 3.78 (dd, half of ABX pattern, J = 13.6, 7.9 Hz, 1H), 2.30 (s, 3H), 2.3-2.35 (m, 1H), 2.10-2.17 (m, 1H), 1.75-1.82 (m, 1H), 1.63-1.71 (m, 1H); 473.2 |
| 64 | ·CF$_3$COOH | Example 17[44] | 2.62 minutes[2]; 487.3 |

TABLE 1-continued

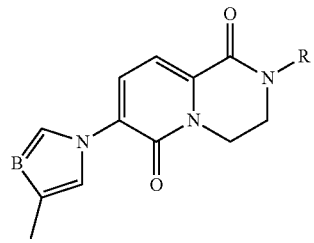

| Ex. # | R = | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 65 | [structure with tetrahydrofuran and 2,4-dichloro-trifluoromethylphenyl; •CF$_3$COOH] | Example 18 | $^1$H NMR (600 MHz, DMSO-d$_6$), δ 9.21 (br s, 1H), 8.00 (d, J = 7.9 Hz, 1H), 7.89 (d, J = 8.3 Hz, 1H), 7.79 (dd, J = 8.3, 2.2 Hz, 1H), 7.73-7.76 (m, 2H), 7.19 (d, J = 7.9 Hz, 1H), 5.06-5.11 (m, 1H), 4.25-4.32 (m, 3H), 3.83-3.88 (m, 3H), 3.78 (dd, half of ABX pattern, J = 14.0, 7.9 Hz, 1H), 2.30 (s, 3H), 2.3-2.36 (m, 1H), 2.11-2.18 (m, 1H), 1.75-1.82 (m, 1H), 1.64-1.71 (m, 1H); 507.2, 509.2 |
| 66 | [structure with tetrahydrofuran and 2-CF$_3$-4,5-difluorophenyl] | Example 8 | 2.67 minutes$^2$; 523.2 |
| 67 | [structure with tetrahydrofuran and 3-F,4,5-dichlorophenyl] | Example 9 | 8.36 (br s, 1H), 7.50 (d, J = 7.8 Hz, 1H), 7.35 (d, J = 7.6 Hz, 1H), 7.21-7.24 (m, 1H), 7.13-7.16 (m, 1H), 7.06 (br dd, J = 9.5, 1.5 Hz, 1H), 4.77-4.88 (m, 2H), 4.49 (ddd, J = 14.2, 6.4, 4.0 Hz, 1H), 4.20 (ddd, J = 14.2, 8.5, 4.2 Hz, 1H), 4.05-4.12 (m, 1H), 3.62-3.78 (m, 2H), 2.33 (br s, 3H), 2.3-2.42 (m, 1H), 2.16-2.26 (m, 1H), 1.77-1.90 (m, 2H), 1.31 (d, J = 7.0 Hz, 3H); 505.3 |
| 68 | [structure with tetrahydrofuran and 2-CF$_3$-4-F-phenyl] | Example 9$^{32}$ | 8.33 (br s, 1H), 7.73 (dd, J = 8.8, 5.7 Hz, 1H), 7.48 (d, J = 7.8 Hz, 1H), 7.22-7.32 (m, 3H, assumed; partially obscured by solvent peak), 7.12-7.15 (m, 1H), 5.14-5.20 (m, 1H), 4.88-4.97 (m, 1H), 4.43 (ddd, J = 14.0, 7.0, 3.9 Hz, 1H), 4.26 (ddd, J = 14.1, 8.1, 4.0 Hz, 1H), 4.02-4.09 (m, 1H), 3.75 (ddd, half of ABXY pattern, J = 13.4, 7.9, 3.9 Hz, 1H), 3.66 (ddd, half of ABXY pattern, J = 13.3, 7.0, 4.0 Hz, 1H), 2.37-2.46 (m, 1H), 2.32 (d, J = 1 Hz, 3H), 2.17-2.27 (m, 1H), 1.70-1.89 (m, 2H), 1.32 (d, J = 6.8 Hz, 3H); 505.3 |

TABLE 1-continued

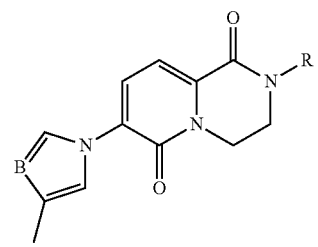

| Ex. # | R = 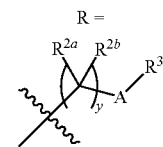 | Method of Preparation; Non-commercial Starting Materials | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |
|---|---|---|---|
| 69 | 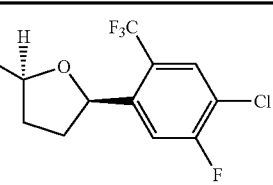 | Example 9[45] | 8.28 (br s, 1H), 7.65 (d, J = 7.0 Hz, 1H), 7.61 (d, J = 10.2 Hz, 1H), 7.48 (d, J = 7.8 Hz, 1H), 7.36 (d, J = 7.4 Hz, 1H), 7.12-7.15 (m, 1H), 5.10-5.16 (m, 1H), 4.94 (dq, J = 9.0, 7.0 Hz, 1H), 4.52-4.60 (m, 1H), 4.12-4.20 (m, 1H), 4.02-4.09 (m, 1H), 3.63-3.75 (m, 2H), 2.38-2.48 (m, 1H), 2.31 (s, 3H), 2.20-2.3 (m, 1H), 1.82-1.91 (m, 1H), 1.70-1.81 (m, 1H), 1.31 (d, J = 7.0 Hz, 3H); 539.3 |
| 70 | 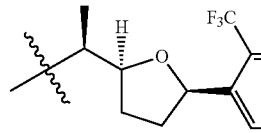 | Example 9[45] | 8.27 (br s, 1H), 7.54-7.62 (m, 2H), 7.47 (d, J = 7.8 Hz, 1H), 7.30 (d, J = 7.8 Hz, 1H), 7.12-7.15 (m, 1H), 5.22-5.28 (m, 1H), 4.90-4.99 (m, 1H), 4.44 (ddd, J = 14, 7, 4 Hz, 1H), 4.29 (ddd, J = 14, 8, 4 Hz, 1H), 4.02-4.09 (m, 1H), 3.63-3.77 (m, 2H), 2.45-2.55 (m, 1H), 2.31 (s, 3H), 2.13-2.21 (m, 1H), 1.69-1.86 (m, 2H), 1.30 (d, J = 7.0 Hz, 3H); 539.3 |
| 71 |  | Example 9 | $^1$H NMR (600 MHz, DMSO-d$_6$), δ 8.24 (d, J = 1.1 Hz, 1H), 7.78 (d, J = 7.9 Hz, 1H), 7.53-7.55 (m, 1H), 7.38-7.40 (m, 1H), 7.09-7.11 (m, 1H), 7.08 (d, J = 7.7 Hz, 1H), 5.14-5.18 (m, 1H), 4.56-4.62 (m, 1H), 4.16-4.24 (m, 2H), 4.10-4.15 (m, 1H), 3.65-3.75 (m, 2H), 2.37-2.43 (m, 1H), 2.15 (d, J = 1 Hz, 3H), 2.07-2.14 (m, 1H), 1.84-1.91 (m, 1H), 1.75-1.82 (m, 1H), 1.22 (d, J = 7.0 Hz, 3H); 493.4 |

1. 3,4-Difluoro-N-hydroxybenzenecarboximidoyl chloride (M. R. Barbachyn et al., *J. Med. Chem.* 2003, 46, 284-302) was subjected to a cycloaddition with ethylene, and the product was acylated according to the method of A. Corsaro et al., *J. Heterocyclic Chem.* 1989, 26, 1691-9, to afford methyl 3-(3,4-difluorophenyl)-4,5-dihydro-1,2-oxazole-4-carboxylate. After ammonolysis, the resulting primary amide was converted to the tert-butoxycarbonyl-protected amine via a Hofmann rearrangement. Deprotection and resolution with (−)-anicyphos[(4S)-2-hydroxy-4-(2-methoxyphenyl)-5,5-dimethyl-1,3,2-dioxaphosphorinane-2-oxide] yielded (4R)-3-(3,4-difluorophenyl)-4,5-dihydro-1,2-oxazol-4-amine. This was converted to the requisite 2-aminoethanol using the general procedure described in Method A.

2. HPLC conditions. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; Flow rate: 2 mL/minute.

3. The reaction of tert-butyl [cis-3-hydroxycyclopentyl] carbamate (see M. Pineschi et al., *Org. Lett.* 2005, 7, 3605-3607) and 3-(trifluoromethyl)phenol under Mitsunobu conditions provided tert-butyl {trans-3-[3-(trifluoromethyl) phenoxy]cyclopentyl}carbamate. Deprotection using acidic conditions afforded trans-3-[3-(trifluoromethyl)phenoxy]cyclopentanamine. This was converted to the requisite 2-aminoethanol using the general procedure described in Method A.

4. tert-Butyl[(2-hydroxycyclopentyl)methyl]carbamate was subjected to Mitsunobu reaction and deprotection as described in footnote 3 to afford 1-{2-[3-(trifluoromethyl) phenoxy]cyclopentyl}methanamine. This was converted to the requisite 2-aminoethanol using the general method described in Method A. Supercritical fluid chromatography was carried out on the final product (Column: Chiralpak AD-H; Eluant: 7:3 carbon dioxide/propanol) and the second-eluting enantiomer was collected. The absolute and relative configuration of this compound were not determined.

5. tert-Butyl(trans-3-hydroxycyclobutyl)carbamate (P. Liu, PCT Int. Appl. 2007, WO 2007062332 A2) was treated with carbon tetrabromide and triphenylphosphine to produce tert-butyl(cis-3-bromocyclobutyl)carbamate, which was subjected to reaction with 2-(trifluoromethyl)phenol, then deprotected with acid to yield trans-3-[2-(trifluoromethyl)phenoxy]cyclobutanamine. This was converted to the requisite 2-aminoethanol using the general method described in Method A.

6. The requisite amine may be prepared according to T. A. Shepherd et al., *J. Med. Chem.* 2002, 45, 2101-2111.

7. HPLC conditions. Column: Waters XBridge C18, 2.1× 50 mm, 5 μm; Mobile phase A: 0.0375% trifluoroacetic acid in water (v/v); Mobile phase B: 0.01875% trifluoroacetic acid in acetonitrile (v/v); Gradient: 1% to 5% B over 0.6 minutes, then 5% to 100% B over 3.4 minutes; Flow rate: 0.8 mL/minute.

8. Cyclobutanecarbonitrile was alkylated with 1-(bromomethyl)-4-fluorobenzene, and the product was reduced with lithium aluminum hydride to generate 1-[1-(4-fluorobenzyl)cyclobutyl]methanamine.

9. Reaction of the Grignard reagent prepared from 1-(bromomethyl)-3,5-difluorobenzene with 6-oxabicyclo[3.1.0]hexane gave trans-2-(3,5-difluorobenzyl)cyclopentanol. Conversion to the mesylate, followed by displacement with sodium azide and reduction with triphenylphosphine afforded cis-2-(3,5-difluorobenzyl)cyclopentanamine.

10. tert-Butyl[trans-3-(hydroxymethyl)cyclobutyl]carbamate and 4-fluoro-2-(trifluoromethyl)phenol were used in a preparation similar to footnote 3.

11. The commercially available amine was converted to the requisite 2-aminoethanol using the general method described in Method A.

12. 2-Chlorocyclohexanone was reacted with 4-chlorophenol, followed by reductive amination with 2-aminoethanol to provide the requisite 2-aminoethanol derivative.

13. Supercritical fluid chromatography was carried out on the final product (Column: Chiralpak OJ-H; Eluant: 7:3 carbon dioxide/methanol) and the first eluting enantiomer was collected. NOE studies indicated cis stereochemistry. The indicated absolute stereochemistry was arbitrarily assigned.

14. Directed metallation of 2-chloro-1-fluoro-4-methoxybenzene with n-butyllithium and tetramethylethylenediamine allowed regiospecific introduction of a methyl group. Subsequent methyl ether cleavage with boron tribromide afforded 3-chloro-4-fluoro-2-methylphenol.

15. 3-(Propan-2-yl)phenol was chlorinated using oxone and potassium chloride to give the requisite phenol.

16. The requisite naphthalenol was prepared as described by J. T. Repine et al., *Tetrahedron Lett.* 2007, 48, 5539-5541.

17. Methyl 2-fluoro-6-hydroxybenzoate was treated with methylmagnesium bromide to afford the tertiary alcohol, which was hydrogenated over palladium on carbon to give the requisite phenol.

18. 5-(3,4-Dichlorophenyl)dihydrofuran-2(3H)-one (see G. J. Quallich et al., *J. Org. Chem.* 1990, 55, 4971-4973) was reduced with diisobutylaluminum hydride, treated with acetic anhydride, and converted to 5-(3,4-dichlorophenyl)tetrahydrofuran-2-carbonitrile by treatment with trimethylsilyl cyanide and boron trifluoride diethyl etherate. Reduction with diisobutylaluminum hydride afforded 1-[5-(3,4-dichlorophenyl)tetrahydrofuran-2-yl]methanamine, which was converted to the requisite 2-aminoethanol using the general approach described in Method A.

19. The requisite [cis-5-(4-chlorophenyl)tetrahydrofuran-2-yl]methanol was prepared by hydrogenation of 5-(4-chlorophenyl)furan-2-carbaldehyde in the presence of ruthenium (IV) oxide hydrate.

20. Example 46 was isolated from the racemic mixture via supercritical fluid chromatography (Column: Chiralcel OJ-H, 5 μm; Eluent: 4:1 carbon dioxide/methanol containing 0.2% isopropylamine), and was the second of the enantiomers that eluted from the column. The first-eluting material was the enantiomer of Example 46, and exhibited an $IC_{50}$ of 511 nM. The absolute stereochemistry of Example 46 was assigned on the basis of its lower $IC_{50}$ (see Table 1), in analogy to the other compounds described herein.

21. The requisite {cis-5-[4-(pentafluoro-$\lambda^6$-sulfanyl)phenyl]tetrahydrofuran-2-yl}methanol was prepared via Suzuki reaction of (5-formylfuran-2-yl)boronic acid with 1-bromo-4-(pentafluoro-$\lambda^6$-sulfanyl)benzene, followed by hydrogenation in the presence of ruthenium(IV) oxide hydrate.

22. Example 47 was isolated from the racemic mixture via supercritical fluid chromatography (Column: Chiralcel OJ-H, 5 μm; Eluent: 65:35 carbon dioxide/propanol containing 0.2% isopropylamine), and was the second of the enantiomers that eluted from the column. The first-eluting material was the enantiomer of Example 47, and exhibited an $IC_{50}$ of 329 nM. The absolute stereochemistry of Example 47 was assigned on the basis of its lower $IC_{50}$ (see Table 1), in analogy to the other compounds described herein.

23. {cis-5-[4-(Trifluoromethoxy)phenyl]tetrahydrofuran-2-yl}methanol was prepared from 5-bromofuran-2-carbaldehyde and [4-(trifluoromethoxy)phenyl]boronic acid using a method analogous to that described in footnote 21.

24. Example 48 was isolated from the racemic mixture via supercritical fluid chromatography (Column: Chiralcel OJ-H, 5 μm; Eluent: 3:1 carbon dioxide/methanol containing 0.2% isopropylamine), and was the second of the enantiomers that eluted from the column. The first-eluting material was the enantiomer of Example 48, and exhibited an $IC_{50}$ of 1230 nM. The absolute stereochemistry of Example 48 was assigned on the basis of its lower $IC_{50}$ (see Table 1), in analogy to the other compounds described herein.

25. tert-Butyl{[(2S,5R)-5-(4-chloro-2-methoxyphenyl)tetrahydrofuran-2-yl]methoxy}diphenylsilane was prepared from (2S)-1-{[tert-butyl(diphenyl)silyl]oxy}-5-(4-chloro-2-methoxyphenyl)pent-4-yn-2-ol using the general method of T. X. M. Nguyen et al., *Letters in Organic Chemistry* 2009, 6, 630-636. This alkyne was prepared via reaction of tert-butyl[(2S)-oxiran-2-ylmethoxy]diphenylsilane with 4-chloro-1-ethynyl-2-methoxybenzene, using n-butyllithium and boron trifluoride diethyl etherate.

26. In this case, reaction with di-μ-chlorodichlorobis(ethylene)diplatinum(II) yielded (4S,5S)-5-(dibenzylamino)-1-[3-fluoro-4-(trifluoromethyl)phenyl]-4-hydroxyhexan-1-one rather than the corresponding 2,3-dihydrofuran. Reaction with p-toluenesulfonic acid and trimethyl orthoformate, followed by subjection to triethylsilane and boron trifluoride diethyl etherate, afforded (1S)—N,N-dibenzyl-1-{(2S)-5-[3-fluoro-4-(trifluoromethyl)phenyl]-2,3-dihydrofuran-2-yl}ethanamine.

27. The final ring closure was carried out via a Mitsunobu reaction using diisopropyl azodicarboxylate.

28. The Sonogashira product in this case was converted to the next intermediate using aqueous platinum(II) chloride.

29. The final ring closure was effected with cesium carbonate in N,N-dimethylformamide rather than lithium bis(trimethylsilyl)amide.

30. The requisite (1S)-1-[(2S,5R)-5-aryltetrahydrofuran-2-yl]ethanamine was prepared from C48 according to Example 9, except that the Sonogashira product in this case was converted to intermediate tert-butyl {(1S)-1-[(2S)-5-hydroxy-5-aryltetrahydrofuran-2-yl]ethyl}carbamate or tert-butyl {(1S)-1-[(2S)-5-methoxy-5-aryltetrahydrofuran-2-yl]ethyl}carbamate using, respectively, aqueous platinum (II) chloride or platinum(II) chloride and trimethyl orthoformate.

31. 2-[({cis-5-[3-(Trifluoromethyl)phenyl]tetrahydrofuran-2-yl}methyl)amino]ethanol was prepared via reaction of cis-2-(bromomethyl)-5-[3-(trifluoromethyl)phenyl]tetrahydrofuran (see H. Ebel et al., PCT Int. Appl., 2010070032, Jun. 24, 2010) with 2-aminoethanol.

32. Example 58 was isolated from the racemic mixture via supercritical fluid chromatography (Column: Chiralcel OJ-H, 5 μm; Eluent: 4:1 carbon dioxide/methanol containing 0.2% isopropylamine), and was the second of the enantiomers that eluted from the column. The first-eluting material was the enantiomer of Example 58, and exhibited an $IC_{50}$ of 1040 nM. The absolute stereochemistry of Example 58 was assigned on the basis of its lower $IC_{50}$ (see Table 1), in analogy to the other compounds described herein.

33. 1-Chloro-2-fluoro-4-iodo-5-methoxybenzene was used as starting material; see J. M. Blaney et al., PCT Int. Appl., 2008150914, Dec. 11, 2008.

34. Sandmeyer reaction of 4-chloro-2-(trifluoromethoxy) aniline afforded the requisite 5-chloro-2-iodophenyl trifluoromethyl ether.

35. The requisite {cis-5-[4-(pentafluoroethyl)phenyl]tetrahydrofuran-2-yl}methanol was prepared via Suzuki reaction of (5-formylfuran-2-yl)boronic acid with 1-bromo-4-(pentafluoroethyl)benzene, followed by hydrogenation over palladium on carbon. 1-Bromo-4-(pentafluoroethyl)benzene was prepared according to the method of W. Lambert et al., PCT Int. Appl., 2011017513, Feb. 10, 2011.

36. The requisite {cis-5-[4-(1,1-difluoroethyl)phenyl]tetrahydrofuran-2-yl}methanol was prepared via Suzuki reaction of 5-bromofuran-2-carbaldehyde with 2-[4-(1,1-difluoroethyl)phenyl]-4,4,5,5-tetramethyl-1,3,2-dioxaborolane, followed by hydrogenation in the presence of ruthenium(IV) oxide hydrate.

37. Example 62 was isolated from the racemic mixture via HPLC (Column: Phenomenex Lux Cellulose-3, 5 μm; Gradient: 50% to 100% ethanol in heptane), and was the second of the enantiomers that eluted from the column. The first-eluting material was the enantiomer of Example 62, and exhibited an $IC_{50}$ of 723 nM. The absolute stereochemistry of Example 62 was assigned on the basis of its lower $IC_{50}$ (see Table 1), in analogy to the other compounds described herein.

38. 1-Bromo-4-chloro-2-(difluoromethoxy)benzene was prepared according to M. Ge et al., U.S. Pat. Appl. Publ., 20070265332, Nov. 15, 2007.

39. In this case, reaction was carried out with di-μ-chlorodichlorobis(ethylene)diplatinum(II) and water, to yield intermediate tert-butyl [(1S)-1-{(2S)-5-[4-chloro-2-(difluoromethoxy)phenyl]-5-hydroxytetrahydrofuran-2-yl}ethyl]carbamate.

40. The trans isomer of Example 64 (2-{[(2S,5S)-5-(4-chloro-3,5-difluorophenyl)tetrahydrofuran-2-yl]methyl}-7-(4-methyl-1H-imidazol-1-yl)-3,4-dihydro-2H-pyrido[1,2-a]pyrazine-1,6-dione) was also isolated from the final step. This compound had an $IC_{50}$ of 184 nM.

41. (2S)-1-{[tert-Butyl(dimethyl)silyl]oxy}-5-[2-(trifluoromethyl)phenyl]pent-4-yn-2-ol (prepared in analogous fashion to the alkyne described in footnote 26) was converted to {(2S,5R)-5-[2-(trifluoromethyl)phenyl]tetrahydrofuran-2-yl}methanol using boron trifluoride diethyl etherate and triethylsilane.

42. Example 66 was a minor diastereomer isolated during purification of Example 17, and was presumed to have the stereochemistry shown.

43. The requisite aryl starting material was prepared from the appropriate fluorinated aniline via halogenation with an N-halosuccinimide, followed by Sandmeyer reaction.

TABLE 2

| Ex. # | Structure | Method of Preparation | HPLC retention time (minutes); Mass spectrum m/z (M + 1) |
|---|---|---|---|
| 72 | 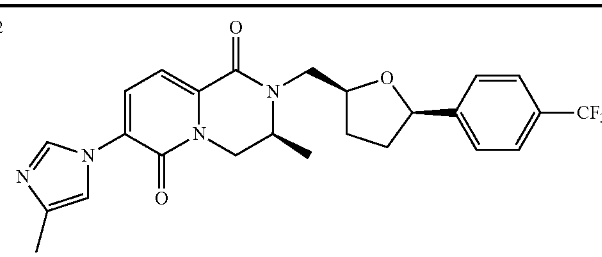 | Example 7[1] | 2.16 minutes[2]; 487.3 |
| 73 | 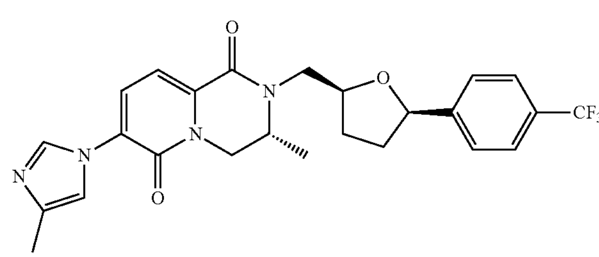 [SMILES: Cc1cn(-c2ccc3n(c2=O)C[C@@H](C)N(C[C@@H]2CC[C@H](c4ccc(C(F)(F)F)cc4)O2)C3=O)cn1] | Example 7[1] | 2.20 minutes[2]; 487.3 |

1. The appropriate homochiral 2-aminopropan-1-ol was used in place of 2-aminoethanol.
2. HPLC conditions. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; Flow rate: 2 mL/minute.

Cell-Based γ-Secretase Assay with ELISA Readout

The ability of compounds to modulate production of amyloid beta protein Aβ(1-42) was determined using human WT-APP overexpressing CHO cells. Cells were plated at 22,000 cells/100 μL well in 96 well tissue culture treated, clear plates (Falcon) in DMEM/F12 based medium and incubated for 24 hours at 37° C. Compounds for testing were diluted in 100% DMSO to achieve an eleven points, half log, dose response for IC$_{50}$ determinations. Compounds were added in fresh medium to achieve 1% final DMSO. Appropriate vehicle or inhibitor controls were added into control wells individually to obtain minimum or maximum inhibition values, respectively, for the assay signal window before the plates were incubated for ~24 hours at 37° C. This procedure produces conditioned media in each well which is tested for Aβ(1-42) levels in the ELISA detection step described next. The remaining cell cultures in each well are also tested for cell toxicity as described below.

Coating of ELISA assay plates was initiated by addition of 50 μL/well of an in-house Aβ(1-42) specific antibody at (3 μg/mL) in 0.1 M NaHCO$_3$ (pH 9.0) into black 384-well Maxisorp® plates (Nunc) and incubated overnight at 4° C. The capture antibody was then aspirated from the ELISA assay plates and plates were washed via (2×100 μL to 4×100 μL) washes with Wash Buffer (Dulbecco's PBS, 0.05% Tween 20). 90 μL/well of Blocking Buffer (Dulbecco's PBS, 1.0% BSA (Sigma A7030)) was then added to plates. Ambient temperature incubation was allowed to proceed for a minimum of two hours. Blocking buffer was then removed and 20 μL/well Assay Buffer (Dulbecco's PBS, 1.0% BSA (Sigma A7030), 0.05% Tween 20) was then added. At this point, 40 μL (in duplicate) of experimental conditioned media (described above) were transferred into wells of the blocked ELISA plates containing the capture antibody, followed by overnight incubation at 4° C. Cell toxicity was also measured in the corresponding remaining cells after removal of the conditioned media for the Aβ(1-42) assay by a colorimetric cell proliferation assay (CellTiter 96®AQ$_{ueous}$ One Solution Cell Proliferation Assay, Promega) according to the manufacturer's instructions.

After overnight incubation of the ELISA assay plates at 4° C., unbound AR peptides were removed via (2×100 μL to 4×100 μL) washes with Wash Buffer. Europium (Eu) labeled (custom labeled, Perkin Elmer) Aβ(1-16) 6e10 Monoclonal Antibody (Covance #SIG-39320) was added, (50 μL/well Eu-6e10 @ 1:10,000, 20 uM EDTA) in Assay Buffer. Incubation at ambient temperature for a minimum of 2 hours was followed by (2×100 μL to 4×100 μL) washes with Wash Buffer, before 30 μL/well of Delfia Enhancement Solution (Perkin Elmer) was added. Following a one hour ambient temperature incubation, the plates were read on an EnVision plate reader (Perkin Elmer) using standard DELFIA TRF settings. Data analysis including inhibitory IC$_{50}$ determination was performed using nonlinear regression fit analysis (in-house software) and the appropriate plate mean values for the maximum and minimum inhibition controls.

TABLE 3

Biological Data for Examples 1-73

| Ex. # | Aβ 42B IC$_{50}$ (nM)[a] | IUPAC Name |
|---|---|---|
| 1 | 211[b] | 7-(4-methyl-1H-imidazol-1-yl)-2-{trans-2-[2-(trifluoromethyl)phenoxy]cyclobutyl}-3,4-dihydro-2H-pyrido[1,2-a]pyrazine-1,6-dione, trifluoroacetate salt |
| 2 | 300[b] | 7-(4-methyl-1H-imidazol-1-yl)-2-{trans-2-[2-(trifluoromethyl)phenoxy]cyclopentyl}-3,4-dihydro-2H-pyrido[1,2-a]pyrazine-1,6-dione |
| 3 | 60.6[b] | 2-{trans-2-[(6,7-difluoronaphthalen-1-yl)oxy]cyclobutyl}-7-(4-methyl-1H-imidazol-1-yl)-3,4-dihydro-2H-pyrido[1,2-a]pyrazine-1,6-dione |
| 4 | 483 | 2-({3-[4-chloro-3-(trifluoromethyl)phenyl]-4,5-dihydro-1,2-oxazol-5-yl}methyl)-7-(4-methyl-1H-imidazol-1-yl)-3,4-dihydro-2H-pyrido[1,2-a]pyrazine-1,6-dione |
| 5 | 140 | 2-{cis-2-[4-fluoro-2-(trifluoromethyl)phenoxy]cyclopentyl}-7-(4-methyl-1H-imidazol-1-yl)-3,4-dihydro-2H-pyrido[1,2-a]pyrazine-1,6-dione |
| 6 | 25 | 7-(4-methyl-1H-imidazol-1-yl)-2-({(2S,3S,5R)-3-methyl-5-[4-(trifluoromethyl)phenyl]tetrahydrofuran-2-yl}methyl)-3,4-dihydro-2H-pyrido[1,2-a]pyrazine-1,6-dione |
| 7 | 73.5 | 2-({(2S,4R,5S)-4-Fluoro-5-[4-(trifluoromethyl)phenyl]tetrahydrofuran-2-yl}methyl)-7-(4-methyl-1H-imidazol-1-yl)-3,4-dihydro-2H-pyrido[1,2-a]pyrazine-1,6-dione |
| 8 | 14.3[c] | 7-(4-methyl-1H-imidazol-1-yl)-2-[(1S)-1-{(2S,5R)-5-[4-(trifluoromethyl)phenyl]tetrahydrofuran-2-yl}ethyl]-3,4-dihydro-2H-pyrido[1,2-a]pyrazine-1,6-dione |
| 9 | 9.1[c] | 2-[(1S)-1-{(2S,5R)-5-[4-chloro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 10 | 3.34 | 2-[(1S)-1-{(2S,5R)-5-[3,5-difluoro-4-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |

TABLE 3-continued

Biological Data for Examples 1-73

| Ex. # | Aβ 42B IC$_{50}$ (nM)[a] | IUPAC Name |
|---|---|---|
| 11 | 40.5 | 7-(4-methyl-1H-imidazol-1-yl)-2-({(2S,5R)-5-methyl-5-[4-(trifluoromethyl)phenyl]tetrahydrofuran-2-yl}methyl)-3,4-dihydro-2H-pyrido[1,2-a]pyrazine-1,6-dione |
| 12 | 725 | 7-(4-methyl-1H-imidazol-1-yl)-2-({(2R,5S)-5-methyl-5-[4-(trifluoromethyl)phenyl]tetrahydrofuran-2-yl}methyl)-3,4-dihydro-2H-pyrido[1,2-a]pyrazine-1,6-dione |
| 13 | 236 | 7-(4-methyl-1H-imidazol-1-yl)-2-({cis-2-methyl-5-[4-(trifluoromethyl)phenyl]tetrahydrofuran-2-yl}methyl)-3,4-dihydro-2H-pyrido[1,2-a]pyrazine-1,6-dione, formate salt |
| 14 | 1040[b] | 7-(4-methyl-1H-imidazol-1-yl)-2-({trans-2-methyl-5-[4-(trifluoromethyl)phenyl]tetrahydrofuran-2-yl}methyl)-3,4-dihydro-2H-pyrido[1,2-a]pyrazine-1,6-dione, formate salt |
| 15 | 29.9 | 7-(4-methyl-1H-imidazol-1-yl)-2-({trans-6-[4-(trifluoromethyl)phenyl]tetrahydro-2H-pyran-2-yl}methyl)-3,4-dihydro-2H-pyrido[1,2-a]pyrazine-1,6-dione, formate salt |
| 16 | 96.6 | 7-(4-methyl-1H-imidazol-1-yl)-2-({cis-6-[4-(trifluoromethyl)phenyl]tetrahydro-2H-pyran-2-yl}methyl)-3,4-dihydro-2H-pyrido[1,2-a]pyrazine-1,6-dione, formate salt |
| 17 | 38.4 | 7-(4-methyl-1H-imidazol-1-yl)-2-({(2S,4S,5R)-4-methyl-5-[4-(trifluoromethyl)phenyl]tetrahydrofuran-2-yl}methyl)-3,4-dihydro-2H-pyrido[1,2-a]pyrazine-1,6-dione, trifluoroacetate salt |
| 18 | 16 | 2-({(2S,5R)-5-[3,5-difluoro-4-(trifluoromethyl)phenyl]tetrahydrofuran-2-yl}methyl)-7-(4-methyl-1H-imidazol-1-yl)-3,4-dihydro-2H-pyrido[1,2-a]pyrazine-1,6-dione |
| 19 | 1460 | 2-[(4R)-3-(3,4-difluorophenyl)-4,5-dihydroisoxazol-4-yl]-7-(4-methyl-1H-imidazol-1-yl)-3,4-dihydro-2H-pyrido[1,2-a]pyrazine-1,6-dione |
| 20 | 1360[b] | 7-(4-methyl-1H-imidazol-1-yl)-2-{trans-3-[3-(trifluoromethyl)phenoxy]cyclopentyl}-3,4-dihydro-2H-pyrido[1,2-a]pyrazine-1,6-dione |
| 21 | 188 | 7-(4-methyl-1H-imidazol-1-yl)-2-({2-[3-(trifluoromethyl)phenoxy]cyclopentyl}methyl)-3,4-dihydro-2H-pyrido[1,2-a]pyrazine-1,6-dione |
| 22 | 789[b] | 7-(4-methyl-1H-imidazol-1-yl)-2-{trans-3-[2-(trifluoromethyl)phenoxy]cyclobutyl}-3,4-dihydro-2H-pyrido[1,2-a]pyrazine-1,6-dione |
| 23 | 98 | 2-{[3-(4-chlorophenyl)cyclohexyl]methyl}-7-(4-methyl-1H-imidazol-1-yl)-3,4-dihydro-2H-pyrido[1,2-a]pyrazine-1,6-dione |
| 24 | 563 | 2-[cis-2-(3,5-difluorophenyl)cyclopentyl]-7-(4-methyl-1H-imidazol-1-yl)-3,4-dihydro-2H-pyrido[1,2-a]pyrazine-1,6-dione |
| 25 | 561 | 2-[cis-2-(3,5-difluorobenzyl)cyclopentyl]-7-(4-methyl-1H-imidazol-1-yl)-3,4-dihydro-2H-pyrido[1,2-a]pyrazine-1,6-dione |
| 26 | 303 | 2-(trans-3-{[4-fluoro-2-(trifluoromethyl)phenoxy]methyl}cyclobutyl)-7-(4-methyl-1H-imidazol-1-yl)-3,4-dihydro-2H-pyrido[1,2-a]pyrazine-1,6-dione |
| 27 | 469 | 7-(4-methyl-1H-imidazol-1-yl)-2-{cis-2-[2-(trifluoromethyl)phenoxy]cyclobutyl}-3,4-dihydro-2H-pyrido[1,2-a]pyrazine-1,6-dione |
| 28 | 591 | 2-[2-(4-chlorophenoxy)cyclohexyl]-7-(4-methyl-1H-imidazol-1-yl)-3,4-dihydro-2H-pyrido[1,2-a]pyrazine-1,6-dione |
| 29 | 80 | 2-{[(1R,3S)-3-(4-chlorophenyl)cyclohexyl]methyl}-7-(4-methyl-1H-imidazol-1-yl)-3,4-dihydro-2H-pyrido[1,2-a]pyrazine-1,6-dione |
| 30 | 711[c] | 2-({3-[2-chloro-5-(trifluoromethyl)phenyl]-4,5-dihydroisoxazol-5-yl}methyl)-7-(4-methyl-1H-imidazol-1-yl)-3,4-dihydro-2H-pyrido[1,2-a]pyrazine-1,6-dione |
| 31 | 353 | 2-({3-[3-chloro-2-fluoro-5-(trifluoromethyl)phenyl]-4,5-dihydro-1,2-oxazol-5-yl}methyl)-7-(4-methyl-1H-imidazol-1-yl)-3,4-dihydro-2H-pyrido[1,2-a]pyrazine-1,6-dione |
| 32 | 429 | 2-({3-[2-chloro-3-(trifluoromethyl)phenyl]-4,5-dihydro-1,2-oxazol-5-yl}methyl)-7-(4-methyl-1H-imidazol-1-yl)-3,4-dihydro-2H-pyrido[1,2-a]pyrazine-1,6-dione |
| 33 | 217[b] | 7-(4-methyl-1H-imidazol-1-yl)-2-{trans-2-[3-(trifluoromethyl)phenoxy]cyclobutyl}-3,4-dihydro-2H-pyrido[1,2-a]pyrazine-1,6-dione |
| 34 | 120 | 2-{trans-2-[4-chloro-2-(trifluoromethyl)phenoxy]cyclobutyl}-7-(4-methyl-1H-imidazol-1-yl)-3,4-dihydro-2H-pyrido[1,2-a]pyrazine-1,6-dione |

TABLE 3-continued

Biological Data for Examples 1-73

| Ex. # | Aβ 42B IC$_{50}$ (nM)$^a$ | IUPAC Name |
|---|---|---|
| 35 | 162 | 2-{trans-2-[(7-fluoro-2,3-dihydro-1H-inden-4-yl)oxy]cyclobutyl}-7-(4-methyl-1H-imidazol-1-yl)-3,4-dihydro-2H-pyrido[1,2-a]pyrazine-1,6-dione |
| 36 | 146$^b$ | 2-[trans-2-(3-chloro-4-fluoro-2-methylphenoxy)cyclobutyl]-7-(4-methyl-1H-imidazol-1-yl)-3,4-dihydro-2H-pyrido[1,2-a]pyrazine-1,6-dione |
| 37 | 158 | 2-{trans-2-[4-chloro-3-(propan-2-yl)phenoxy]cyclobutyl}-7-(4-methyl-1H-imidazol-1-yl)-3,4-dihydro-2H-pyrido[1,2-a]pyrazine-1,6-dione |
| 38 | 164 | 7-(4-methyl-1H-imidazol-1-yl)-2-[trans-2-(naphthalen-1-yloxy)cyclobutyl]-3,4-dihydro-2H-pyrido[1,2-a]pyrazine-1,6-dione |
| 39 | 112 | 2-{trans-2-[(7-fluoronaphthalen-1-yl)oxy]cyclobutyl}-7-(4-methyl-1H-imidazol-1-yl)-3,4-dihydro-2H-pyrido[1,2-a]pyrazine-1,6-dione |
| 40 | 153 | 2-{trans-2-[3-fluoro-2-(propan-2-yl)phenoxy]cyclobutyl}-7-(4-methyl-1H-imidazol-1-yl)-3,4-dihydro-2H-pyrido[1,2-a]pyrazine-1,6-dione |
| 41 | 157 | 2-{trans-2-[2-chloro-3-(trifluoromethyl)phenoxy]cyclobutyl}-7-(4-methyl-1H-imidazol-1-yl)-3,4-dihydro-2H-pyrido[1,2-a]pyrazine-1,6-dione |
| 42 | 117 | 2-{[5-(3,4-dichlorophenyl)tetrahydrofuran-2-yl]methyl}-7-(4-methyl-1H-imidazol-1-yl)-3,4-dihydro-2H-pyrido[1,2-a]pyrazine-1,6-dione, trifluoroacetate salt |
| 43 | 27.6$^c$ | 7-(4-methyl-1H-imidazol-1-yl)-2-({(2S,5R)-5-[4-(trifluoromethyl)phenyl]tetrahydrofuran-2-yl}methyl)-3,4-dihydro-2H-pyrido[1,2-a]pyrazine-1,6-dione |
| 44 | 52.1 | 2-{[(2S,5R)-5-(4-chlorophenyl)tetrahydrofuran-2-yl]methyl}-7-(4-methyl-1H-imidazol-1-yl)-3,4-dihydro-2H-pyrido[1,2-a]pyrazine-1,6-dione |
| 45 | 26.6$^c$ | 7-(4-methyl-1H-imidazol-1-yl)-2-({(2S,5R)-5-[4-(pentafluoro-lambda~6~-sulfanyl)phenyl]tetrahydrofuran-2-yl}methyl)-3,4-dihydro-2H-pyrido[1,2-a]pyrazine-1,6-dione |
| 46 | 60.3 | 7-(4-methyl-1H-imidazol-1-yl)-2-({(2S,5R)-5-[4-(trifluoromethoxy)phenyl]tetrahydrofuran-2-yl}methyl)-3,4-dihydro-2H-pyrido[1,2-a]pyrazine-1,6-dione |
| 47 | 15.7$^c$ | 2-({(2S,5R)-5-[3-fluoro-4-(trifluoromethyl)phenyl]tetrahydrofuran-2-yl}methyl)-7-(4-methyl-1H-imidazol-1-yl)-3,4-dihydro-2H-pyrido[1,2-a]pyrazine-1,6-dione |
| 48 | 63.8 | 2-{[(2S,5R)-5-(4-cyclopropylphenyl)tetrahydrofuran-2-yl]methyl}-7-(4-methyl-1H-imidazol-1-yl)-3,4-dihydro-2H-pyrido[1,2-a]pyrazine-1,6-dione |
| 49 | 21.6 | 2-{[(2S,5R)-5-(4-chloro-2-methoxyphenyl)tetrahydrofuran-2-yl]methyl}-7-(4-methyl-1H-imidazol-1-yl)-3,4-dihydro-2H-pyrido[1,2-a]pyrazine-1,6-dione |
| 50 | 11 | 2-[(1S)-1-{(2S,5R)-5-[2,3-difluoro-4-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 51 | 8.35$^c$ | 2-[(1S)-1-{(2S,5R)-5-[3-fluoro-4-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 52 | 15 | 2-[(1S)-1-{(2S,5R)-5-[2-methoxy-4-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 53 | 29.1 | 2-[(1S)-1-{(2S,5R)-5-[2-chloro-4-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 54 | 11.4 | 2-{(1S)-1-[(2S,5R)-5-(4-chloro-2,5-difluorophenyl)tetrahydrofuran-2-yl]ethyl}-7-(4-methyl-1H-imidazol-1-yl)-3,4-dihydro-2H-pyrido[1,2-a]pyrazine-1,6-dione |
| 55 | 5.48$^c$ | 2-{(1S)-1-[(2S,5R)-5-(4-chloro-3,5-difluorophenyl)tetrahydrofuran-2-yl]ethyl}-7-(4-methyl-1H-imidazol-1-yl)-3,4-dihydro-2H-pyrido[1,2-a]pyrazine-1,6-dione |
| 56 | 81.2 | 7-(4-methyl-1H-imidazol-1-yl)-2-({(2S,5R)-5-[3-(trifluoromethyl)phenyl]tetrahydrofuran-2-yl}methyl)-3,4-dihydro-2H-pyrido[1,2-a]pyrazine-1,6-dione |

TABLE 3-continued

Biological Data for Examples 1-73

| Ex. # | Aβ 42B IC$_{50}$ (nM)[a] | IUPAC Name |
|---|---|---|
| 57 | 11.1 | 2-{(1S)-1-[(2S,5R)-5-(4-chloro-5-fluoro-2-methoxyphenyl)tetrahydrofuran-2-yl]ethyl}-7-(4-methyl-1H-imidazol-1-yl)-3,4-dihydro-2H-pyrido[1,2-a]pyrazine-1,6-dione |
| 58 | 14.5 | 2-[(1S)-1-{(2S,5R)-5-[4-chloro-2-(trifluoromethoxy)phenyl]tetrahydrofuran-2-yl}ethyl]-7-(4-methyl-1H-imidazol-1-yl)-3,4-dihydro-2H-pyrido[1,2-a]pyrazine-1,6-dione |
| 59 | 157 | 7-(4-methyl-1H-imidazol-1-yl)-2-({cis-5-[4-(pentafluoroethyl)phenyl]tetrahydrofuran-2-yl}methyl)-3,4-dihydro-2H-pyrido[1,2-a]pyrazine-1,6-dione, hydrochloride salt |
| 60 | 73.3 | 2-({(2S,5R)-5-[4-(1,1-difluoroethyl)phenyl]tetrahydrofuran-2-yl}methyl)-7-(4-methyl-1H-imidazol-1-yl)-3,4-dihydro-2H-pyrido[1,2-a]pyrazine-1,6-dione |
| 61 | 24.6 | 2-[(1S)-1-{(2S,5R)-5-[4-chloro-2-(difluoromethoxy)phenyl]tetrahydrofuran-2-yl}ethyl]-7-(4-methyl-1H-imidazol-1-yl)-3,4-dihydro-2H-pyrido[1,2-a]pyrazine-1,6-dione |
| 62 | 13.3 | 2-{[(2S,5R)-5-(4-chloro-3,5-difluorophenyl)tetrahydrofuran-2-yl]methyl}-7-(4-methyl-1H-imidazol-1-yl)-3,4-dihydro-2H-pyrido[1,2-a]pyrazine-1,6-dione |
| 63 | 73.3 | 7-(4-methyl-1H-imidazol-1-yl)-2-({(2S,5R)-5-[2-(trifluoromethyl)phenyl]tetrahydrofuran-2-yl}methyl)-3,4-dihydro-2H-pyrido[1,2-a]pyrazine-1,6-dione, trifluoroacetate salt |
| 64 | 73.5 | 7-(4-methyl-1H-imidazol-1-yl)-2-({(2S,4R,5R)-4-methyl-5-[4-(trifluoromethyl)phenyl]tetrahydrofuran-2-yl}methyl)-3,4-dihydro-2H-pyrido[1,2-a]pyrazine-1,6-dione, trifluoroacetate salt |
| 65 | 26.8 | 2-({(2S,5R)-5-[4-chloro-2-(trifluoromethyl)phenyl]tetrahydrofuran-2-yl}methyl)-7-(4-methyl-1H-imidazol-1-yl)-3,4-dihydro-2H-pyrido[1,2-a]pyrazine-1,6-dione, trifluoroacetate salt |
| 66 | 33.5 | 2-[(1S)-1-{(2S,5R)-5-[4,5-difluoro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 67 | 5.78 | 2-{(1S)-1-[(2S,5R)-5-(3,4-dichloro-5-fluorophenyl)tetrahydrofuran-2-yl]ethyl}-7-(4-methyl-1H-imidazol-1-yl)-3,4-dihydro-2H-pyrido[1,2-a]pyrazine-1,6-dione |
| 68 | 24.2 | 2-[(1S)-1-{(2S,5R)-5-[4-fluoro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 69 | 7.84 | 2-[(1S)-1-{(2S,5R)-5-[4-chloro-5-fluoro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 70 | 10 | 2-[(1S)-1-{(2S,5R)-5-[4-chloro-3-fluoro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione |
| 71 | 52.4 | 7-(4-methyl-1H-imidazol-1-yl)-2-[(1S)-1-{(2S,5R)-5-[5-(trifluoromethyl)thiophen-2-yl]tetrahydrofuran-2-yl}ethyl]-3,4-dihydro-2H-pyrido[1,2-a]pyrazine-1,6-dione |
| 72 | 46.4 | (3S)-3-methyl-7-(4-methyl-1H-imidazol-1-yl)-2-({(2S,5R)-5-[4-(trifluoromethyl)phenyl]tetrahydrofuran-2-yl}methyl)-3,4-dihydro-2H-pyrido[1,2-a]pyrazine-1,6-dione |
| 73 | 19.8 | (3R)-3-methyl-7-(4-methyl-1H-imidazol-1-yl)-2-({(2S,5R)-5-[4-(trifluoromethyl)phenyl]tetrahydrofuran-2-yl}methyl)-3,4-dihydro-2H-pyrido[1,2-a]pyrazine-1,6-dione |

[a] Reported IC$_{50}$ values are the geometric mean of 2-4 determinations.
[b] IC$_{50}$ value is from a single determination.
[c] Reported IC$_{50}$ value is the geometric mean of ≥5 determinations.
[d] Not determined

We claim:

1. The compound 2-[(1S)-1-{(2S,5R)-5-[4-chloro-5-fluoro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione.

2. A pharmaceutical composition comprising the compound according to claim 1 in admixture with at least one pharmaceutically acceptable excipient.

3. A method for reducing the production of amyloid beta proteins in a human in need thereof comprising administering a therapeutically effective amount of the compound according to claim 1 to said human.

4. A method for treating Alzheimer's disease in a human in need thereof comprising administering to said human a therapeutically effective amount of the compound according to claim 1.

5. A pharmaceutically acceptable salt of the compound 2-[(1S)-1-{(2S,5R)-5-[4-chloro-5-fluoro-2-(trifluoromethyl)phenyl]tetrahydrofuran-2-yl}ethyl]-7-(4-methyl-1H-imidazol-1-yl)-3,4-dihydro-2H-pyrido[1,2-a]pyrazine-1,6-dione.

6. A pharmaceutical composition comprising the compound according to claim 5 in admixture with at least one pharmaceutically acceptable excipient.

7. A method for reducing the production of amyloid beta proteins in a human in need thereof comprising administering a therapeutically effective amount of the compound according to claim 5 to said human.

8. A method for treating Alzheimer's disease in a human in need thereof comprising administering to said human a therapeutically effective amount of the compound according to claim 5.

* * * * *